(12) United States Patent
Bowen et al.

(10) Patent No.: US 12,156,533 B2
(45) Date of Patent: *Dec. 3, 2024

(54) NICOTINE SALT FORMULATIONS FOR AEROSOL DEVICES AND METHODS THEREOF

(71) Applicant: JUUL Labs, Inc., San Francisco, CA (US)

(72) Inventors: Adam Bowen, San Francisco, CA (US); Chenyue Xing, San Francisco, CA (US)

(73) Assignee: JUUL LABS, INC., San Francisco, CA (US)

( * ) Notice: Subject to any disclaimer, the term of this patent is extended or adjusted under 35 U.S.C. 154(b) by 316 days.

This patent is subject to a terminal disclaimer.

(21) Appl. No.: 17/171,976

(22) Filed: Feb. 9, 2021

(65) Prior Publication Data

US 2021/0186082 A1 Jun. 24, 2021

Related U.S. Application Data

(63) Continuation of application No. 14/925,961, filed on Oct. 28, 2015, now Pat. No. 10,952,468, which is a
(Continued)

(51) Int. Cl.
| | | |
|---|---|---|
| *A24B 15/16* | (2020.01) | |
| *A24B 15/167* | (2020.01) | |
| *A61K 9/00* | (2006.01) | |
| *A61K 9/12* | (2006.01) | |
| *A61K 31/465* | (2006.01) | |
| *A61K 31/60* | (2006.01) | |

(Continued)

(52) U.S. Cl.
CPC ............ *A24B 15/167* (2016.11); *A24B 15/16* (2013.01); *A61K 9/007* (2013.01); *A61K 9/12* (2013.01); *A61K 31/465* (2013.01); *A61K 31/60* (2013.01); *A61K 47/10* (2013.01); *A24F 40/10* (2020.01)

(58) Field of Classification Search
None
See application file for complete search history.

(56) References Cited

U.S. PATENT DOCUMENTS

| 374,584 A | 12/1887 | Cook |
|---|---|---|
| 576,653 A | 2/1897 | Bowlby |

(Continued)

FOREIGN PATENT DOCUMENTS

| CA | 2641869 A1 | 5/2010 |
|---|---|---|
| CN | 85106876 A | 9/1986 |

(Continued)

OTHER PUBLICATIONS

"A Randomised Placebo-Controlled Trial of a Nicotine Inhaler and Nicotine Patches for Smoking cessation," 5 pages, available at http://www.otago.ac.nz/wellington/otago047634.pdf.

(Continued)

*Primary Examiner* — Dionne W. Mayes
(74) *Attorney, Agent, or Firm* — Mintz, Levin, Cohn, Ferris, Glovsky and Popeo, P.C.

(57) ABSTRACT

A nicotine salt liquid formulation for generating an inhalable aerosol in an electronic cigarette comprising nicotine salt that forms about 0.5% to about 20% nicotine is provided.

19 Claims, 8 Drawing Sheets

Related U.S. Application Data continuation of application No. 14/271,071, filed on May 6, 2014, now abandoned.

(60) Provisional application No. 61/912,507, filed on Dec. 5, 2013, provisional application No. 61/820,128, filed on May 6, 2013.

(51) Int. Cl.
*A61K 47/10* (2017.01)
*A24F 40/10* (2020.01)

(56) References Cited

U.S. PATENT DOCUMENTS

| | | |
|---|---|---|
| 595,070 A | 12/1897 | Oldenbusch |
| 720,007 A | 2/1903 | Dexter |
| 799,844 A | 9/1905 | Fuller |
| 968,160 A | 8/1910 | Johnson |
| 969,076 A | 8/1910 | Pender |
| 1,067,531 A | 7/1913 | MacGregor |
| 1,163,183 A | 12/1915 | Stoll |
| 1,299,162 A | 4/1919 | Fisher |
| 1,505,748 A | 8/1924 | Louis |
| 1,552,877 A | 9/1925 | Phillipps et al. |
| 1,632,335 A | 6/1927 | Hiering |
| 1,706,244 A | 3/1929 | Louis |
| 1,845,340 A | 2/1932 | Ritz |
| 1,972,118 A | 9/1934 | McDill |
| 1,998,683 A | 4/1935 | Montgomery |
| 2,031,363 A | 2/1936 | Elof |
| 2,039,559 A | 5/1936 | Segal |
| 2,104,266 A | 1/1938 | McCormick |
| 2,159,698 A | 5/1939 | Harris et al. |
| 2,177,636 A | 10/1939 | Coffelt et al. |
| 2,195,260 A | 3/1940 | Rasener |
| 2,231,909 A | 2/1941 | Hempal |
| 2,327,120 A | 8/1943 | McCoon |
| 2,460,427 A | 2/1949 | Musselman et al. |
| 2,483,304 A | 9/1949 | Rudolf |
| 2,502,561 A | 4/1950 | Ludwig |
| 2,765,949 A | 10/1956 | Swan |
| 2,830,597 A | 4/1958 | Kummli |
| 2,860,638 A | 11/1958 | Bartolomeo |
| 2,897,958 A | 8/1959 | Tarleton et al. |
| 2,935,987 A | 5/1960 | Ackerbauer |
| 3,146,937 A | 9/1964 | Joseph |
| 3,258,015 A | 6/1966 | Ellis et al. |
| 3,271,719 A | 9/1966 | Ovshinsky |
| 3,292,634 A | 12/1966 | Beucler |
| 3,373,915 A | 3/1968 | Anderson et al. |
| 3,420,360 A | 1/1969 | Young |
| 3,443,827 A | 5/1969 | Acker et al. |
| 3,456,645 A | 7/1969 | Brock |
| 3,479,561 A | 11/1969 | Janning |
| 3,567,014 A | 3/1971 | Feigelman |
| 3,675,661 A | 7/1972 | Weaver |
| 3,707,017 A | 12/1972 | Paquette |
| 3,792,704 A | 2/1974 | Parker |
| 3,815,597 A | 6/1974 | Goettelman |
| 3,861,523 A | 1/1975 | Fountain et al. |
| 3,878,850 A | 4/1975 | Gibson et al. |
| 3,941,300 A | 3/1976 | Troth |
| 4,020,853 A | 5/1977 | Nuttall |
| 4,049,005 A | 9/1977 | Hernandez et al. |
| 4,066,088 A | 1/1978 | Ensor |
| 4,207,976 A | 6/1980 | Herman |
| 4,215,708 A | 8/1980 | Bron |
| 4,219,032 A | 8/1980 | Tabatznik et al. |
| 4,303,083 A | 12/1981 | Burruss, Jr. |
| 4,312,367 A | 1/1982 | Seeman |
| 4,506,683 A | 3/1985 | Cantrell et al. |
| 4,519,319 A | 5/1985 | Howlett |
| 4,520,938 A | 6/1985 | Finke |
| 4,579,858 A | 4/1986 | Ferno et al. |
| 4,595,024 A | 6/1986 | Greene et al. |
| 4,597,961 A | 7/1986 | Etscorn |
| 4,648,393 A | 3/1987 | Landis et al. |
| 4,708,151 A | 11/1987 | Shelar |
| 4,735,217 A | 4/1988 | Gerth et al. |
| 4,771,796 A | 9/1988 | Myer |
| 4,793,365 A | 12/1988 | Sensabaugh, Jr. et al. |
| 4,794,323 A | 12/1988 | Zhou et al. |
| 4,798,310 A | 1/1989 | Kasai et al. |
| 4,813,536 A | 3/1989 | Willis |
| 4,819,665 A | 4/1989 | Roberts et al. |
| 4,830,028 A | 5/1989 | Lawson et al. |
| 4,836,224 A | 6/1989 | Lawson et al. |
| 4,846,199 A | 7/1989 | Rose |
| 4,848,374 A | 7/1989 | Chard et al. |
| 4,848,563 A | 7/1989 | Robbins |
| 4,893,639 A | 1/1990 | White |
| 4,907,606 A | 3/1990 | Lilja et al. |
| 4,941,483 A | 7/1990 | Ridings et al. |
| 4,944,317 A | 7/1990 | Thal |
| 4,947,874 A | 8/1990 | Brooks et al. |
| 4,947,875 A | 8/1990 | Brooks et al. |
| 5,005,759 A | 4/1991 | Bouche |
| 5,020,548 A | 6/1991 | Farrier et al. |
| 5,027,836 A | 7/1991 | Shannon et al. |
| 5,031,646 A | 7/1991 | Lippiello et al. |
| 5,042,509 A | 8/1991 | Banerjee et al. |
| 5,050,621 A | 9/1991 | Creighton et al. |
| 5,060,671 A | 10/1991 | Counts et al. |
| 5,065,776 A | 11/1991 | Lawson et al. |
| 5,076,297 A | 12/1991 | Farrier et al. |
| 5,105,831 A | 4/1992 | Banerjee et al. |
| 5,105,838 A | 4/1992 | White et al. |
| 5,123,530 A | 6/1992 | Lee |
| 5,133,368 A | 7/1992 | Neumann et al. |
| 5,141,004 A | 8/1992 | Porenski |
| 5,144,962 A | 9/1992 | Counts et al. |
| 5,152,456 A | 10/1992 | Ross et al. |
| 5,183,062 A | 2/1993 | Clearman et al. |
| 5,224,498 A | 7/1993 | Deevi et al. |
| 5,240,012 A | 8/1993 | Ehrman et al. |
| 5,249,586 A | 10/1993 | Morgan et al. |
| 5,261,424 A | 11/1993 | Sprinkel, Jr. |
| 5,269,237 A | 12/1993 | Baker et al. |
| 5,269,327 A | 12/1993 | Counts et al. |
| 5,303,720 A | 4/1994 | Banerjee et al. |
| 5,322,075 A | 6/1994 | Deevi et al. |
| 5,324,498 A | 6/1994 | Streusand et al. |
| 5,372,148 A | 12/1994 | McCafferty et al. |
| 5,388,574 A | 2/1995 | Ingebrethsen |
| 5,449,078 A | 9/1995 | Akers |
| 5,456,269 A | 10/1995 | Kollasch |
| 5,497,791 A | 3/1996 | Bowen et al. |
| 5,529,078 A | 6/1996 | Rehder et al. |
| 5,579,934 A | 12/1996 | Buono |
| 5,591,368 A | 1/1997 | Fleischhauer et al. |
| 5,605,226 A | 2/1997 | Hernlein |
| 5,626,866 A | 5/1997 | Ebert et al. |
| 5,641,064 A | 6/1997 | Goserud |
| 5,649,552 A | 7/1997 | Cho et al. |
| 5,666,977 A | 9/1997 | Higgins et al. |
| 5,666,978 A | 9/1997 | Counts et al. |
| 5,708,258 A | 1/1998 | Counts et al. |
| 5,730,118 A | 3/1998 | Hermanson |
| 5,730,158 A | 3/1998 | Collins et al. |
| 5,746,587 A | 5/1998 | Racine et al. |
| 5,810,164 A | 9/1998 | Rennecamp |
| 5,819,756 A | 10/1998 | Mielordt |
| 5,845,649 A | 12/1998 | Saito et al. |
| 5,865,185 A | 2/1999 | Collins et al. |
| 5,878,752 A | 3/1999 | Adams et al. |
| 5,881,884 A | 3/1999 | Podosek |
| 5,894,841 A | 4/1999 | Voges |
| 5,931,828 A | 8/1999 | Durkee |
| 5,934,289 A | 8/1999 | Watkins et al. |
| 5,938,018 A | 8/1999 | Keaveney et al. |
| 5,944,025 A | 8/1999 | Cook et al. |
| 5,954,979 A | 9/1999 | Counts et al. |
| 5,967,310 A | 10/1999 | Hill |
| 5,975,415 A | 11/1999 | Zehnal |

(56) References Cited

U.S. PATENT DOCUMENTS

| | | |
|---|---|---|
| 5,979,460 A | 11/1999 | Matsumura |
| 5,994,025 A | 11/1999 | Iwasa et al. |
| 5,996,589 A | 12/1999 | St. Charles |
| 6,053,176 A | 4/2000 | Adams et al. |
| 6,089,857 A | 7/2000 | Matsuura et al. |
| 6,095,153 A | 8/2000 | Kessler et al. |
| 6,102,036 A | 8/2000 | Slutsky et al. |
| 6,125,853 A | 10/2000 | Susa et al. |
| 6,155,268 A | 12/2000 | Takeuchi |
| 6,164,287 A | 12/2000 | White |
| 6,196,232 B1 | 3/2001 | Chkadua |
| 6,211,194 B1 | 4/2001 | Westman et al. |
| 6,234,169 B1 | 5/2001 | Bulbrook et al. |
| 6,269,966 B1 | 8/2001 | Pallo et al. |
| 6,324,261 B1 | 11/2001 | Merte |
| 6,344,222 B1 | 2/2002 | Cherukuri et al. |
| 6,349,728 B1 | 2/2002 | Pham |
| 6,358,060 B2 | 3/2002 | Pinney et al. |
| 6,381,739 B1 | 4/2002 | Breternitz, Jr. et al. |
| 6,386,371 B1 | 5/2002 | Parsons |
| 6,431,363 B1 | 8/2002 | Hacker |
| 6,446,793 B1 | 9/2002 | Layshock |
| 6,510,982 B2 | 1/2003 | White et al. |
| 6,532,965 B1 | 3/2003 | Abhulimen et al. |
| 6,536,442 B2 | 3/2003 | St. Charles et al. |
| 6,557,708 B2 | 5/2003 | Polacco |
| 6,598,607 B2 | 7/2003 | Adiga et al. |
| 6,603,924 B2 | 8/2003 | Brown et al. |
| 6,606,998 B1 | 8/2003 | Gold |
| 6,612,404 B2 | 9/2003 | Sweet et al. |
| 6,615,840 B1 | 9/2003 | Fournier et al. |
| 6,622,867 B2 | 9/2003 | Menceles |
| 6,655,379 B2 | 12/2003 | Clark et al. |
| 6,672,762 B1 | 1/2004 | Faircloth et al. |
| 6,688,313 B2 | 2/2004 | Wrenn et al. |
| 6,726,006 B1 | 4/2004 | Funderburk et al. |
| 6,772,756 B2 | 8/2004 | Shayan |
| 6,799,576 B2 | 10/2004 | Farr |
| 6,803,545 B2 | 10/2004 | Blake et al. |
| 6,805,545 B2 | 10/2004 | Slaboden |
| 6,810,883 B2 | 11/2004 | Felter et al. |
| 6,827,573 B2 | 12/2004 | St. Charles et al. |
| 6,874,507 B2 | 4/2005 | Farr |
| 6,893,654 B2 | 5/2005 | Pinney et al. |
| 6,909,840 B2 | 6/2005 | Harwig et al. |
| 6,954,979 B2 | 10/2005 | Logan |
| 7,000,775 B2 | 2/2006 | Gelardi et al. |
| 7,015,796 B2 | 3/2006 | Snyder |
| 7,025,066 B2 | 4/2006 | Lawson et al. |
| D557,209 S | 12/2007 | Ahlgren et al. |
| 7,374,048 B2 | 5/2008 | Mazurek |
| 7,387,788 B1 | 6/2008 | Carrara et al. |
| 7,428,905 B2 | 9/2008 | Mua |
| 7,488,171 B2 | 2/2009 | St. Charles et al. |
| D590,990 S | 4/2009 | Hon |
| D590,991 S | 4/2009 | Hon |
| 7,546,703 B2 | 6/2009 | Johnske et al. |
| 7,621,403 B2 | 11/2009 | Althoff et al. |
| 7,644,823 B2 | 1/2010 | Gelardi et al. |
| D611,409 S | 3/2010 | Green et al. |
| 7,726,320 B2 | 6/2010 | Robinson et al. |
| 7,766,013 B2 | 8/2010 | Wensley et al. |
| 7,767,698 B2 | 8/2010 | Warchol et al. |
| D624,238 S | 9/2010 | Turner |
| 7,801,573 B2 | 9/2010 | Yazdi et al. |
| 7,815,332 B1 | 10/2010 | Smith |
| 7,832,410 B2 | 11/2010 | Hon |
| 7,886,507 B2 | 2/2011 | McGuinness, Jr. |
| D642,330 S | 7/2011 | Turner |
| D644,375 S | 8/2011 | Zhou |
| 7,988,034 B2 | 8/2011 | Pezzoli |
| 8,003,080 B2 | 8/2011 | Rabinowitz et al. |
| D649,932 S | 12/2011 | Symons |
| 8,079,371 B2 | 12/2011 | Robinson et al. |
| D653,803 S | 2/2012 | Timmermans |
| 8,141,701 B2 | 3/2012 | Hodges |
| 8,156,944 B2 | 4/2012 | Han |
| 8,251,060 B2 | 8/2012 | White et al. |
| 8,308,624 B2 | 11/2012 | Travers et al. |
| 8,314,235 B2 | 11/2012 | Dixit et al. |
| 8,322,350 B2 | 12/2012 | Lipowicz |
| D674,748 S | 1/2013 | Ferber et al. |
| 8,371,310 B2 | 2/2013 | Brenneise |
| 8,375,957 B2 | 2/2013 | Hon |
| 8,381,739 B2 | 2/2013 | Gonda |
| 8,387,612 B2 | 3/2013 | Damani et al. |
| 8,443,534 B2 | 5/2013 | Goodfellow et al. |
| 8,464,867 B2 | 6/2013 | Holloway et al. |
| D686,987 S | 7/2013 | Vanstone et al. |
| 8,479,747 B2 | 7/2013 | O'Connell |
| 8,490,629 B1 | 7/2013 | Shenassa et al. |
| 8,511,318 B2 | 8/2013 | Hon |
| 8,539,959 B1 | 9/2013 | Scatterday |
| 8,541,401 B2 | 9/2013 | Mishra et al. |
| D691,324 S | 10/2013 | Saliman |
| 8,550,069 B2 | 10/2013 | Alelov |
| D695,450 S | 12/2013 | Benassayag et al. |
| 8,596,460 B2 | 12/2013 | Scatterday |
| D700,572 S | 3/2014 | Esses |
| 8,671,952 B2 | 3/2014 | Winterson et al. |
| 8,707,965 B2 | 4/2014 | Newton |
| D704,629 S | 5/2014 | Liu |
| D704,634 S | 5/2014 | Eidelman et al. |
| 8,714,150 B2 | 5/2014 | Alelov |
| D707,389 S | 6/2014 | Liu |
| 8,741,348 B2 | 6/2014 | Hansson et al. |
| 8,794,245 B1 | 8/2014 | Scatterday |
| 8,794,434 B2 | 8/2014 | Scatterday et al. |
| 8,809,261 B2 | 8/2014 | Elsohly et al. |
| 8,820,330 B2 | 9/2014 | Bellinger et al. |
| 8,851,081 B2 | 10/2014 | Fernando et al. |
| 8,851,083 B2 | 10/2014 | Oglesby et al. |
| 8,881,737 B2 | 11/2014 | Collett et al. |
| 8,899,238 B2 | 12/2014 | Robinson et al. |
| 8,905,040 B2 | 12/2014 | Scatterday et al. |
| 8,910,641 B2 | 12/2014 | Hon |
| 8,915,254 B2 | 12/2014 | Monsees et al. |
| 8,919,561 B2 | 12/2014 | Boisseau |
| 8,925,555 B2 | 1/2015 | Monsees et al. |
| 8,931,492 B2 | 1/2015 | Scatterday |
| D725,310 S | 3/2015 | Eksouzian |
| D725,823 S | 3/2015 | Scatterday et al. |
| 8,991,402 B2 | 3/2015 | Bowen et al. |
| 9,004,073 B2 | 4/2015 | Tucker et al. |
| 9,010,335 B1 | 4/2015 | Scatterday |
| 9,072,321 B2 | 7/2015 | Liu |
| 9,089,166 B1 | 7/2015 | Scatterday |
| 9,095,175 B2 | 8/2015 | Terry et al. |
| 9,215,895 B2 * | 12/2015 | Bowen ................. A61K 47/10 |
| 9,220,302 B2 | 12/2015 | DePiano et al. |
| 9,226,526 B2 | 1/2016 | Liu |
| 9,254,002 B2 | 2/2016 | Chong et al. |
| 9,255,277 B2 | 2/2016 | Bakker et al. |
| 9,271,525 B2 | 3/2016 | Liu |
| 9,271,529 B2 | 3/2016 | Alima |
| 9,272,103 B2 | 3/2016 | Storz |
| 9,277,768 B2 | 3/2016 | Xiu |
| 9,277,769 B2 | 3/2016 | Liu |
| 9,282,772 B2 | 3/2016 | Tucker et al. |
| 9,282,773 B2 | 3/2016 | Greim et al. |
| 9,289,014 B2 | 3/2016 | Tucker et al. |
| 9,308,336 B2 | 4/2016 | Newton |
| 9,315,890 B1 | 4/2016 | Frick et al. |
| 9,319,865 B2 | 4/2016 | Van Phan et al. |
| 9,326,547 B2 | 5/2016 | Tucker et al. |
| 9,345,269 B2 | 5/2016 | Liu |
| 9,351,522 B2 | 5/2016 | Safari |
| 9,380,810 B2 | 7/2016 | Rose et al. |
| 9,420,829 B2 | 8/2016 | Thorens et al. |
| 9,427,022 B2 | 8/2016 | Levin et al. |
| 9,456,632 B2 | 10/2016 | Hon |
| 9,462,832 B2 | 10/2016 | Lord |
| 9,497,995 B2 | 11/2016 | Liu |
| 9,510,624 B2 | 12/2016 | Li et al. |

(56) References Cited

U.S. PATENT DOCUMENTS

| | | | |
|---|---|---|---|
| 9,538,781 B2 | 1/2017 | Zheng | |
| 9,554,597 B2 | 1/2017 | Liu | |
| 9,596,881 B2 | 3/2017 | Chiolini et al. | |
| 9,623,592 B2 | 4/2017 | Liu | |
| 9,629,391 B2 | 4/2017 | Dube et al. | |
| 9,635,886 B2 | 5/2017 | Tu | |
| 9,642,397 B2 | 5/2017 | Dai et al. | |
| 9,648,905 B2 | 5/2017 | Levitz et al. | |
| 9,675,108 B2 | 6/2017 | Liu | |
| 9,682,203 B2 | 6/2017 | Dahne et al. | |
| 9,682,204 B2 | 6/2017 | Matsumoto et al. | |
| 9,687,025 B2 | 6/2017 | Cyphert et al. | |
| 9,687,027 B2 | 6/2017 | Poston et al. | |
| 9,693,584 B2 | 7/2017 | Hearn et al. | |
| 9,717,274 B2 | 8/2017 | Daehne et al. | |
| 9,717,279 B2 | 8/2017 | Hon | |
| 10,058,129 B2 | 8/2018 | Monsees et al. | |
| 10,463,069 B2* | 11/2019 | Bowen | A24B 15/16 |
| 10,952,468 B2* | 3/2021 | Bowen | A24B 15/16 |
| 11,478,021 B2 | 10/2022 | Bowen et al. | |
| 11,510,433 B2 | 11/2022 | Bowen et al. | |
| 2001/0015209 A1 | 8/2001 | Zielke | |
| 2001/0032643 A1 | 10/2001 | Hochrainer et al. | |
| 2001/0032795 A1 | 10/2001 | Weinstein et al. | |
| 2001/0052480 A1 | 12/2001 | Kawaguchi et al. | |
| 2002/0043554 A1 | 4/2002 | White et al. | |
| 2002/0059939 A1 | 5/2002 | Fox | |
| 2002/0078951 A1 | 6/2002 | Nichols et al. | |
| 2002/0175164 A1 | 11/2002 | Dees et al. | |
| 2003/0005926 A1 | 1/2003 | Jones et al. | |
| 2003/0089377 A1 | 5/2003 | Hajaligol et al. | |
| 2004/0002520 A1 | 1/2004 | Soderlund et al. | |
| 2004/0031495 A1 | 2/2004 | Steinberg | |
| 2004/0050382 A1 | 3/2004 | Goodchild | |
| 2004/0099266 A1 | 5/2004 | Cross et al. | |
| 2004/0149296 A1 | 8/2004 | Rostami et al. | |
| 2004/0149624 A1 | 8/2004 | Wischusen et al. | |
| 2004/0168950 A1* | 9/2004 | Barker | B65D 75/26 206/528 |
| 2004/0173224 A1 | 9/2004 | Burgard et al. | |
| 2004/0173229 A1 | 9/2004 | Crooks et al. | |
| 2004/0182403 A1 | 9/2004 | Andersson et al. | |
| 2004/0191322 A1 | 9/2004 | Hansson | |
| 2004/0221857 A1 | 11/2004 | Dominguez | |
| 2004/0237974 A1 | 12/2004 | Min | |
| 2005/0016549 A1 | 1/2005 | Banerjee et al. | |
| 2005/0016550 A1 | 1/2005 | Katase | |
| 2005/0034723 A1 | 2/2005 | Bennett et al. | |
| 2005/0053665 A1 | 3/2005 | Ek et al. | |
| 2005/0061759 A1 | 3/2005 | Doucette | |
| 2005/0118545 A1 | 6/2005 | Wong | |
| 2005/0145533 A1 | 7/2005 | Seligson | |
| 2005/0169849 A1 | 8/2005 | Farr | |
| 2005/0172976 A1 | 8/2005 | Newman et al. | |
| 2005/0244521 A1 | 11/2005 | Strickland et al. | |
| 2005/0268911 A1 | 12/2005 | Cross et al. | |
| 2006/0018840 A1 | 1/2006 | Lechuga-Ballesteros et al. | |
| 2006/0054676 A1 | 3/2006 | Wischusen | |
| 2006/0102175 A1 | 5/2006 | Nelson | |
| 2006/0150991 A1 | 7/2006 | Lee | |
| 2006/0157072 A1 | 7/2006 | Albino et al. | |
| 2006/0191546 A1 | 8/2006 | Takano et al. | |
| 2006/0191548 A1 | 8/2006 | Strickland et al. | |
| 2006/0196518 A1 | 9/2006 | Hon | |
| 2006/0243290 A1 | 11/2006 | Reich et al. | |
| 2006/0254948 A1 | 11/2006 | Herbert et al. | |
| 2006/0255105 A1 | 11/2006 | Sweet | |
| 2007/0006889 A1 | 1/2007 | Kobal et al. | |
| 2007/0045288 A1 | 3/2007 | Nelson | |
| 2007/0062548 A1 | 3/2007 | Horstmann et al. | |
| 2007/0074734 A1 | 4/2007 | Braunshteyn et al. | |
| 2007/0098148 A1 | 5/2007 | Sherman | |
| 2007/0102013 A1 | 5/2007 | Adams et al. | |
| 2007/0144514 A1 | 6/2007 | Yeates et al. | |
| 2007/0163610 A1 | 7/2007 | Lindell et al. | |
| 2007/0215164 A1 | 9/2007 | Mehio | |
| 2007/0235046 A1 | 10/2007 | Gedevanishvili | |
| 2007/0267031 A1 | 11/2007 | Hon | |
| 2007/0267033 A1 | 11/2007 | Mishra et al. | |
| 2007/0277816 A1 | 12/2007 | Morrison et al. | |
| 2007/0280652 A1 | 12/2007 | Williams | |
| 2007/0283972 A1 | 12/2007 | Monsees et al. | |
| 2008/0000763 A1 | 1/2008 | Cove | |
| 2008/0023003 A1 | 1/2008 | Rosenthal | |
| 2008/0029095 A1 | 2/2008 | Esser | |
| 2008/0092912 A1 | 4/2008 | Robinson et al. | |
| 2008/0121610 A1 | 5/2008 | Nagata et al. | |
| 2008/0138423 A1 | 6/2008 | Gonda | |
| 2008/0149118 A1 | 6/2008 | Oglesby et al. | |
| 2008/0216828 A1 | 9/2008 | Wensley et al. | |
| 2008/0228214 A1 | 9/2008 | Hoan et al. | |
| 2008/0241255 A1 | 10/2008 | Rose et al. | |
| 2008/0257367 A1 | 10/2008 | Paterno et al. | |
| 2008/0276947 A1 | 11/2008 | Martzel | |
| 2008/0286340 A1 | 11/2008 | Andersson et al. | |
| 2008/0302375 A1 | 12/2008 | Andersson et al. | |
| 2009/0001085 A1 | 1/2009 | Bartz et al. | |
| 2009/0004249 A1 | 1/2009 | Gonda | |
| 2009/0023819 A1 | 1/2009 | Axelsson | |
| 2009/0095287 A1 | 4/2009 | Emarlou | |
| 2009/0095311 A1 | 4/2009 | Han | |
| 2009/0111287 A1 | 4/2009 | Lindberg et al. | |
| 2009/0126745 A1 | 5/2009 | Hon | |
| 2009/0133691 A1 | 5/2009 | Yamada et al. | |
| 2009/0139533 A1 | 6/2009 | Park et al. | |
| 2009/0151717 A1 | 6/2009 | Bowen et al. | |
| 2009/0230117 A1 | 9/2009 | Fernando et al. | |
| 2009/0255534 A1 | 10/2009 | Paterno | |
| 2009/0267252 A1 | 10/2009 | Ikeyama | |
| 2009/0272379 A1 | 11/2009 | Thorens et al. | |
| 2009/0283103 A1 | 11/2009 | Nielsen et al. | |
| 2009/0288668 A1 | 11/2009 | Inagaki | |
| 2009/0288669 A1 | 11/2009 | Hutchens | |
| 2009/0293892 A1 | 12/2009 | Williams et al. | |
| 2009/0293895 A1 | 12/2009 | Axelsson et al. | |
| 2010/0000672 A1 | 1/2010 | Fogle | |
| 2010/0006092 A1 | 1/2010 | Hale et al. | |
| 2010/0024834 A1 | 2/2010 | Oglesby et al. | |
| 2010/0031968 A1 | 2/2010 | Sheikh et al. | |
| 2010/0156193 A1 | 6/2010 | Rhodes et al. | |
| 2010/0163063 A1 | 7/2010 | Fernando et al. | |
| 2010/0186757 A1 | 7/2010 | Crooks et al. | |
| 2010/0200006 A1 | 8/2010 | Robinson et al. | |
| 2010/0200008 A1 | 8/2010 | Taieb | |
| 2010/0236562 A1 | 9/2010 | Hearn et al. | |
| 2010/0242974 A1 | 9/2010 | Pan | |
| 2010/0242976 A1 | 9/2010 | Katayama et al. | |
| 2010/0260688 A1 | 10/2010 | Warchol et al. | |
| 2010/0275938 A1 | 11/2010 | Roth et al. | |
| 2010/0276333 A1 | 11/2010 | Couture | |
| 2010/0307116 A1 | 12/2010 | Fisher | |
| 2011/0005535 A1 | 1/2011 | Xiu | |
| 2011/0030706 A1 | 2/2011 | Gibson et al. | |
| 2011/0036346 A1 | 2/2011 | Cohen et al. | |
| 2011/0041861 A1 | 2/2011 | Sebastian et al. | |
| 2011/0049226 A1 | 3/2011 | Moreau et al. | |
| 2011/0094523 A1 | 4/2011 | Thorens et al. | |
| 2011/0108023 A1 | 5/2011 | McKinney et al. | |
| 2011/0155153 A1 | 6/2011 | Thorens et al. | |
| 2011/0162667 A1 | 7/2011 | Burke et al. | |
| 2011/0168194 A1 | 7/2011 | Hon | |
| 2011/0180433 A1 | 7/2011 | Rennecamp | |
| 2011/0192397 A1 | 8/2011 | Saskar et al. | |
| 2011/0226236 A1 | 9/2011 | Buchberger | |
| 2011/0226266 A1 | 9/2011 | Tao | |
| 2011/0232654 A1 | 9/2011 | Mass | |
| 2011/0236002 A1 | 9/2011 | Oglesby et al. | |
| 2011/0240047 A1 | 10/2011 | Adamic | |
| 2011/0265806 A1 | 11/2011 | Alarcon et al. | |
| 2011/0268809 A1 | 11/2011 | Brinkley et al. | |
| 2011/0274628 A1 | 11/2011 | Borschke | |
| 2011/0277780 A1 | 11/2011 | Terry et al. | |
| 2011/0278189 A1 | 11/2011 | Terry et al. | |
| 2011/0293535 A1 | 12/2011 | Kosik et al. | |

(56) References Cited

U.S. PATENT DOCUMENTS

| | | |
|---|---|---|
| 2011/0315701 A1 | 12/2011 | Everson |
| 2012/0006342 A1 | 1/2012 | Rose et al. |
| 2012/0039981 A1 | 2/2012 | Pedersen et al. |
| 2012/0060853 A1 | 3/2012 | Robinson et al. |
| 2012/0111347 A1 | 5/2012 | Hon |
| 2012/0152265 A1 | 6/2012 | Dube et al. |
| 2012/0192880 A1 | 8/2012 | Dube et al. |
| 2012/0199146 A1 | 8/2012 | Marangos |
| 2012/0204889 A1 | 8/2012 | Xiu |
| 2012/0227753 A1 | 9/2012 | Newton |
| 2012/0255567 A1 | 10/2012 | Rose et al. |
| 2012/0260927 A1 | 10/2012 | Liu |
| 2012/0261286 A1 | 10/2012 | Holloway et al. |
| 2012/0267383 A1 | 10/2012 | Van Rooyen |
| 2012/0273589 A1 | 11/2012 | Hon |
| 2012/0285475 A1 | 11/2012 | Liu |
| 2012/0291791 A1 | 11/2012 | Pradeep |
| 2012/0325227 A1 | 12/2012 | Robinson et al. |
| 2012/0325228 A1 | 12/2012 | Williams |
| 2013/0042865 A1 | 2/2013 | Monsees et al. |
| 2013/0068239 A1 | 3/2013 | Youn |
| 2013/0081642 A1 | 4/2013 | Safari |
| 2013/0098377 A1 | 4/2013 | Borschke et al. |
| 2013/0140200 A1 | 6/2013 | Scatterday |
| 2013/0152922 A1 | 6/2013 | Benassayag et al. |
| 2013/0186416 A1 | 7/2013 | Gao et al. |
| 2013/0192615 A1 | 8/2013 | Tucker et al. |
| 2013/0192617 A1 | 8/2013 | Thompson |
| 2013/0199528 A1 | 8/2013 | Goodman et al. |
| 2013/0213417 A1 | 8/2013 | Chong et al. |
| 2013/0213419 A1 | 8/2013 | Tucker et al. |
| 2013/0228191 A1 | 9/2013 | Newton |
| 2013/0247924 A1 | 9/2013 | Scatterday et al. |
| 2013/0248385 A1 | 9/2013 | Scatterday et al. |
| 2013/0255702 A1 | 10/2013 | Griffith, Jr. et al. |
| 2013/0276802 A1 | 10/2013 | Scatterday |
| 2013/0284190 A1 | 10/2013 | Scatterday et al. |
| 2013/0284191 A1 | 10/2013 | Scatterday et al. |
| 2013/0298905 A1 | 11/2013 | Levin et al. |
| 2013/0312742 A1 | 11/2013 | Monsees et al. |
| 2013/0313139 A1 | 11/2013 | Scatterday et al. |
| 2013/0319435 A1 | 12/2013 | Flick |
| 2013/0319440 A1 | 12/2013 | Capuano |
| 2013/0333700 A1 | 12/2013 | Buchberger |
| 2013/0333712 A1 | 12/2013 | Scatterday |
| 2013/0340775 A1 | 12/2013 | Juster et al. |
| 2014/0000638 A1 | 1/2014 | Sebastian et al. |
| 2014/0007891 A1 | 1/2014 | Liu |
| 2014/0014124 A1 | 1/2014 | Glasberg et al. |
| 2014/0014126 A1 | 1/2014 | Peleg et al. |
| 2014/0041655 A1 | 2/2014 | Barron et al. |
| 2014/0041658 A1 | 2/2014 | Goodman et al. |
| 2014/0053856 A1 | 2/2014 | Liu |
| 2014/0053858 A1 | 2/2014 | Liu |
| 2014/0060552 A1 | 3/2014 | Cohen |
| 2014/0060556 A1 | 3/2014 | Liu |
| 2014/0083442 A1 | 3/2014 | Scatterday |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0116455 A1 | 5/2014 | Youn |
| 2014/0123990 A1 | 5/2014 | Timmermans |
| 2014/0144429 A1 | 5/2014 | Wensley et al. |
| 2014/0150810 A1 | 6/2014 | Hon |
| 2014/0166028 A1 | 6/2014 | Fuisz et al. |
| 2014/0174459 A1 | 6/2014 | Burstyn |
| 2014/0190501 A1 | 7/2014 | Liu |
| 2014/0190503 A1 | 7/2014 | Li et al. |
| 2014/0196731 A1 | 7/2014 | Scatterday |
| 2014/0196735 A1 | 7/2014 | Liu |
| 2014/0202472 A1 | 7/2014 | Levitz et al. |
| 2014/0202474 A1 | 7/2014 | Peleg et al. |
| 2014/0209105 A1 | 7/2014 | Sears et al. |
| 2014/0216450 A1 | 8/2014 | Liu |
| 2014/0217092 A1 | 8/2014 | Kawka et al. |
| 2014/0230835 A1 | 8/2014 | Saliman |
| 2014/0261474 A1 | 9/2014 | Gonda |
| 2014/0261486 A1 | 9/2014 | Potter et al. |
| 2014/0261487 A1 | 9/2014 | Chapman et al. |
| 2014/0261507 A1 | 9/2014 | Balder |
| 2014/0270727 A1 | 9/2014 | Ampolini et al. |
| 2014/0271946 A1 | 9/2014 | Kobal et al. |
| 2014/0299137 A1 | 10/2014 | Kieckbusch et al. |
| 2014/0301721 A1 | 10/2014 | Ruscio et al. |
| 2014/0305450 A1 | 10/2014 | Xiang |
| 2014/0345631 A1 | 11/2014 | Bowen et al. |
| 2014/0345633 A1 | 11/2014 | Talon et al. |
| 2014/0345635 A1 | 11/2014 | Rabinowitz et al. |
| 2014/0355969 A1 | 12/2014 | Stern |
| 2014/0366898 A1 | 12/2014 | Monsees et al. |
| 2014/0378790 A1 | 12/2014 | Cohen |
| 2015/0020823 A1 | 1/2015 | Lipowicz et al. |
| 2015/0020824 A1 | 1/2015 | Bowen et al. |
| 2015/0020825 A1 | 1/2015 | Galloway et al. |
| 2015/0020830 A1 | 1/2015 | Koller |
| 2015/0020831 A1 | 1/2015 | Weigensberg et al. |
| 2015/0027457 A1 | 1/2015 | Janardhan et al. |
| 2015/0027468 A1 | 1/2015 | Li et al. |
| 2015/0027472 A1 | 1/2015 | Amir |
| 2015/0034103 A1 | 2/2015 | Hon |
| 2015/0034104 A1 | 2/2015 | Zhou |
| 2015/0038567 A1 | 2/2015 | Herkenroth et al. |
| 2015/0040929 A1 | 2/2015 | Hon |
| 2015/0042412 A1 | 2/2015 | Imbornone et al. |
| 2015/0101625 A1 | 4/2015 | Newton et al. |
| 2015/0101945 A1 | 4/2015 | Scatterday |
| 2015/0122252 A1 | 5/2015 | Frija |
| 2015/0122274 A1 | 5/2015 | Cohen et al. |
| 2015/0128965 A1 | 5/2015 | Lord |
| 2015/0128966 A1 | 5/2015 | Lord |
| 2015/0128967 A1 | 5/2015 | Robinson et al. |
| 2015/0128976 A1 | 5/2015 | Verleur et al. |
| 2015/0136153 A1 | 5/2015 | Lord |
| 2015/0136158 A1 | 5/2015 | Stevens et al. |
| 2015/0142387 A1 | 5/2015 | Alarcon et al. |
| 2015/0144147 A1 | 5/2015 | Li et al. |
| 2015/0150308 A1 | 6/2015 | Monsees et al. |
| 2015/0157054 A1 | 6/2015 | Liu |
| 2015/0157056 A1 | 6/2015 | Bowen et al. |
| 2015/0157893 A1 | 6/2015 | Canevari |
| 2015/0157901 A1 | 6/2015 | Mace et al. |
| 2015/0164141 A1 | 6/2015 | Newton |
| 2015/0164144 A1 | 6/2015 | Liu |
| 2015/0164147 A1 | 6/2015 | Verleur et al. |
| 2015/0165067 A1 | 6/2015 | Balderes et al. |
| 2015/0181928 A1 | 7/2015 | Liu |
| 2015/0189695 A1 | 7/2015 | Xiang |
| 2015/0196059 A1 | 7/2015 | Liu |
| 2015/0196060 A1 | 7/2015 | Wensley et al. |
| 2015/0208729 A1 | 7/2015 | Monsees et al. |
| 2015/0208731 A1 | 7/2015 | Malamud et al. |
| 2015/0216237 A1 | 8/2015 | Wensley et al. |
| 2015/0223521 A1 | 8/2015 | Menting et al. |
| 2015/0224268 A1 | 8/2015 | Henry et al. |
| 2015/0237917 A1 | 8/2015 | Lord |
| 2015/0237918 A1 | 8/2015 | Liu |
| 2015/0245654 A1 | 9/2015 | Memari et al. |
| 2015/0245660 A1 | 9/2015 | Lord |
| 2015/0257445 A1 | 9/2015 | Henry, Jr. et al. |
| 2015/0258289 A1 | 9/2015 | Henry, Jr. et al. |
| 2015/0272220 A1 | 10/2015 | Spinka et al. |
| 2015/0272222 A1 | 10/2015 | Spinka et al. |
| 2015/0282525 A1 | 10/2015 | Plojoux et al. |
| 2015/0282527 A1 | 10/2015 | Henry, Jr. |
| 2015/0305409 A1 | 10/2015 | Verleur et al. |
| 2015/0313275 A1 | 11/2015 | Anderson et al. |
| 2015/0313285 A1 | 11/2015 | Waller et al. |
| 2015/0320114 A1 | 11/2015 | Wu |
| 2015/0335074 A1 | 11/2015 | Leung |
| 2015/0351456 A1 | 12/2015 | Johnson et al. |
| 2015/0359264 A1 | 12/2015 | Fernando et al. |
| 2015/0366265 A1 | 12/2015 | Lansing |
| 2015/0366266 A1 | 12/2015 | Chen |
| 2016/0021931 A1 | 1/2016 | Hawes et al. |

(56) References Cited

U.S. PATENT DOCUMENTS

| | | |
|---|---|---|
| 2016/0021932 A1 | 1/2016 | Silvestrini et al. |
| 2016/0021933 A1 | 1/2016 | Thorens et al. |
| 2016/0021934 A1 | 1/2016 | Cadieux et al. |
| 2016/0029694 A1 | 2/2016 | Clements et al. |
| 2016/0029697 A1 | 2/2016 | Shafer |
| 2016/0029698 A1 | 2/2016 | Xiang |
| 2016/0044967 A1 | 2/2016 | Bowen et al. |
| 2016/0044968 A1 | 2/2016 | Bowen et al. |
| 2016/0053988 A1 | 2/2016 | Quintana |
| 2016/0057811 A1 | 2/2016 | Alarcon et al. |
| 2016/0058071 A1 | 3/2016 | Hearn |
| 2016/0058072 A1 | 3/2016 | Liu |
| 2016/0073692 A1 | 3/2016 | Alarcon et al. |
| 2016/0081393 A1 | 3/2016 | Black |
| 2016/0081395 A1 | 3/2016 | Thorens et al. |
| 2016/0095355 A1 | 4/2016 | Hearn |
| 2016/0106154 A1 | 4/2016 | Lord |
| 2016/0106155 A1 | 4/2016 | Reevell |
| 2016/0106936 A1 | 4/2016 | Kimmel |
| 2016/0109115 A1 | 4/2016 | Lipowicz |
| 2016/0120218 A1 | 5/2016 | Schennum et al. |
| 2016/0120220 A1 | 5/2016 | Malgat et al. |
| 2016/0120227 A1 | 5/2016 | Levitz et al. |
| 2016/0120228 A1 | 5/2016 | Rostami et al. |
| 2016/0135503 A1 | 5/2016 | Liu |
| 2016/0143359 A1 | 5/2016 | Xiang |
| 2016/0143365 A1 | 5/2016 | Liu |
| 2016/0157524 A1 | 6/2016 | Bowen et al. |
| 2016/0166564 A1 | 6/2016 | Myers et al. |
| 2016/0174603 A1 | 6/2016 | Abayarathna et al. |
| 2016/0174611 A1 | 6/2016 | Monsees et al. |
| 2016/0200463 A1 | 7/2016 | Hodges et al. |
| 2016/0227839 A1 | 8/2016 | Zuber et al. |
| 2016/0227840 A1 | 8/2016 | Xiang |
| 2016/0242466 A1 | 8/2016 | Lord et al. |
| 2016/0249680 A1 | 9/2016 | Liu |
| 2016/0250201 A1 | 9/2016 | Rose et al. |
| 2016/0270451 A1 | 9/2016 | Hon |
| 2016/0278435 A1 | 9/2016 | Choukroun et al. |
| 2016/0295924 A1 | 10/2016 | Liu |
| 2016/0295926 A1 | 10/2016 | Zuber |
| 2016/0302471 A1 | 10/2016 | Bowen et al. |
| 2016/0302483 A1 | 10/2016 | Liu |
| 2016/0302484 A1 | 10/2016 | Gupta et al. |
| 2016/0302486 A1 | 10/2016 | Eroch |
| 2016/0309784 A1 | 10/2016 | Silvestrini et al. |
| 2016/0324215 A1 | 11/2016 | Mironov et al. |
| 2016/0331033 A1 | 11/2016 | Hopps et al. |
| 2016/0331038 A1 | 11/2016 | Farine et al. |
| 2016/0331040 A1 | 11/2016 | Nakano et al. |
| 2016/0338402 A1 | 11/2016 | Buehler et al. |
| 2016/0338410 A1 | 11/2016 | Batista et al. |
| 2016/0338411 A1 | 11/2016 | Liu |
| 2016/0345627 A1 | 12/2016 | Liu |
| 2016/0345630 A1 | 12/2016 | Mironov et al. |
| 2016/0366939 A1 | 12/2016 | Alarcon et al. |
| 2016/0368670 A1 | 12/2016 | Beardsall |
| 2016/0371464 A1 | 12/2016 | Bricker |
| 2016/0374390 A1 | 12/2016 | Liu |
| 2016/0374398 A1 | 12/2016 | Amir |
| 2017/0019951 A1 | 1/2017 | Louveau et al. |
| 2017/0049155 A1 | 2/2017 | Liu |
| 2017/0064999 A1 | 3/2017 | Perez et al. |
| 2017/0071257 A1 | 3/2017 | Lin |
| 2017/0079329 A1 | 3/2017 | Zitzke |
| 2017/0079331 A1 | 3/2017 | James et al. |

FOREIGN PATENT DOCUMENTS

| | | | |
|---|---|---|---|
| CN | 1122213 A | | 5/1996 |
| CN | 1298294 A | | 6/2001 |
| CN | 1541577 A | | 11/2004 |
| CN | 1607950 A | | 4/2005 |
| CN | 1887126 A | | 1/2007 |
| CN | 101742985 A | | 6/2010 |
| CN | 101756352 A | | 6/2010 |
| CN | 101869356 A | | 10/2010 |
| CN | 102014995 A | | 4/2011 |
| CN | 102316850 A | | 1/2012 |
| CN | 102355914 A | | 2/2012 |
| CN | 102612361 A | | 7/2012 |
| CN | 102754924 A | | 10/2012 |
| CN | 102892413 A | | 1/2013 |
| CN | 102933199 A | | 2/2013 |
| CN | 105263345 A | | 1/2016 |
| DE | 4200639 A1 | | 7/1992 |
| DE | 19854005 A1 | | 5/2000 |
| DE | 19854012 A1 | | 5/2000 |
| EP | 0148749 A2 | | 7/1985 |
| EP | 0283672 A2 | | 9/1988 |
| EP | 0354661 A2 | | 2/1990 |
| EP | 0532194 A1 | | 3/1993 |
| EP | 0535695 A2 | | 4/1993 |
| EP | 0283672 B1 | | 9/1993 |
| EP | 1458388 A1 | | 9/2004 |
| EP | 1618803 A1 | | 1/2006 |
| EP | 1618803 B1 | | 12/2008 |
| EP | 2022349 A1 | | 2/2009 |
| EP | 2022350 A1 | | 2/2009 |
| EP | 2110033 A1 | | 10/2009 |
| EP | 2152313 A1 | | 2/2010 |
| EP | 2186507 A2 | | 5/2010 |
| EP | 2319934 A2 | | 5/2011 |
| EP | 2325093 A1 | | 5/2011 |
| EP | 2609821 A1 | | 7/2013 |
| EP | 2856893 A1 | | 4/2015 |
| EP | 2908675 A1 | | 8/2015 |
| EP | 3024343 A2 | | 6/2016 |
| EP | 3062646 A1 | | 9/2016 |
| EP | 3065581 A2 | | 9/2016 |
| EP | 3068244 A1 | | 9/2016 |
| EP | 3214957 B1 | | 9/2017 |
| EP | 2915443 B1 | | 8/2019 |
| ES | 2118034 A1 | | 9/1998 |
| GB | 1025630 A | | 4/1966 |
| GB | 1065678 A | | 4/1967 |
| IE | S20050051 | | 2/2005 |
| IE | S20050563 | | 8/2005 |
| IE | 20050615 | | 9/2005 |
| JP | S61254170 A | | 11/1986 |
| JP | 62278975 | | 12/1987 |
| JP | 6437276 | | 2/1989 |
| JP | 02-145179 | | 6/1990 |
| JP | H02145179 A | | 6/1990 |
| JP | A-03-049671 | | 3/1991 |
| JP | 03049671 | | 4/1991 |
| JP | 03180166 | | 6/1991 |
| JP | 09-075058 | | 3/1997 |
| JP | 10-501999 | | 2/1998 |
| JP | 11178563 | | 6/1999 |
| JP | 2000203639 A | | 7/2000 |
| JP | 2000236865 A | | 9/2000 |
| JP | 2001165437 A | | 6/2001 |
| JP | 2005034021 A | | 2/2005 |
| JP | 2006504430 A | | 2/2006 |
| JP | 2006-524494 A | | 11/2006 |
| JP | 2009108082 A | | 5/2009 |
| JP | 2010531188 A | | 9/2010 |
| JP | 2010532672 A | | 10/2010 |
| JP | 2012506263 A | | 3/2012 |
| JP | 2013505240 A | | 2/2013 |
| JP | 2016513030 A | | 5/2016 |
| JP | 6877141 B2 | | 12/2016 |
| KR | 10-0193885 B1 | | 6/1999 |
| KR | 0193885 | | 6/1999 |
| KR | 100694546 B1 | | 3/2007 |
| KR | 20100034029 A | | 3/2010 |
| KR | 10-2010-0088626 B1 | | 8/2010 |
| KR | 10-2011-0094118 B1 | | 8/2011 |
| KR | 101074619 B1 | | 10/2011 |
| MX | 2015015175 A | | 1/2016 |
| RU | 94815 U1 | | 6/2010 |
| UA | 67598 U | | 2/2012 |
| WO | WO-9501137 A1 | | 1/1995 |

(56) References Cited

FOREIGN PATENT DOCUMENTS

| | | |
|---|---|---|
| WO | WO-9712639 A1 | 4/1997 |
| WO | WO-0028842 A1 | 5/2000 |
| WO | WO-03055486 A1 | 7/2003 |
| WO | WO-03056948 A1 | 7/2003 |
| WO | WO-03082031 A1 | 10/2003 |
| WO | WO-03094900 A1 | 11/2003 |
| WO | WO-2003103387 A2 | 12/2003 |
| WO | WO-2004002446 A1 | 1/2004 |
| WO | WO-2004064548 A1 | 8/2004 |
| WO | WO-2004076289 A2 | 9/2004 |
| WO | WO-2004080216 A1 | 9/2004 |
| WO | WO-2005020726 A1 | 3/2005 |
| WO | WO-2006004646 A1 | 1/2006 |
| WO | WO-2006015070 A1 | 2/2006 |
| WO | WO-2006053082 A2 | 5/2006 |
| WO | WO-2006082571 A1 | 8/2006 |
| WO | WO-2007026131 A1 | 3/2007 |
| WO | WO-2007078273 A1 | 7/2007 |
| WO | WO-2008077271 A1 | 7/2008 |
| WO | WO-2008121610 A1 | 10/2008 |
| WO | WO-2009001085 A2 | 12/2008 |
| WO | WO-2009069519 A1 | 6/2009 |
| WO | WO-2009079641 A2 | 6/2009 |
| WO | WO-2010023561 A1 | 3/2010 |
| WO | WO-2010045671 A1 | 4/2010 |
| WO | WO-2011033396 A2 | 3/2011 |
| WO | WO-2011034723 A1 | 3/2011 |
| WO | WO-2011038104 A2 | 3/2011 |
| WO | WO-2011/117580 A2 | 9/2011 |
| WO | WO-2011109849 A1 | 9/2011 |
| WO | WO-2011139684 A2 | 11/2011 |
| WO | WO-2012021972 A1 | 2/2012 |
| WO | WO-2012027350 A2 | 3/2012 |
| WO | WO-2012/085207 A1 | 6/2012 |
| WO | WO-2012120487 A2 | 9/2012 |
| WO | WO-2012134380 A1 | 10/2012 |
| WO | WO-2013013808 A1 | 1/2013 |
| WO | WO-2013044537 A1 | 4/2013 |
| WO | WO-2013050934 A1 | 4/2013 |
| WO | WO-2013083631 A1 | 6/2013 |
| WO | WO-2013083635 A1 | 6/2013 |
| WO | WO-2013088230 A1 | 6/2013 |
| WO | WO-2013089551 A1 | 6/2013 |
| WO | WO-2013/098398 A2 | 7/2013 |
| WO | WO-2013116558 A1 | 8/2013 |
| WO | WO-2013116561 A1 | 8/2013 |
| WO | WO-2013141906 A1 | 9/2013 |
| WO | WO-2013141907 A1 | 9/2013 |
| WO | WO-2013141994 A1 | 9/2013 |
| WO | WO-2013141998 A2 | 9/2013 |
| WO | WO-2013142671 A1 | 9/2013 |
| WO | WO-2013142678 A1 | 9/2013 |
| WO | WO-2014004648 A1 | 1/2014 |
| WO | WO-2014040915 A1 | 3/2014 |
| WO | WO-2014093127 A2 | 6/2014 |
| WO | WO-2014101734 A1 | 7/2014 |
| WO | WO-2014113592 A1 | 7/2014 |
| WO | WO-2014118286 A2 | 8/2014 |
| WO | WO-2014139611 A1 | 9/2014 |
| WO | WO-2014140087 A1 | 9/2014 |
| WO | WO-2014150245 A1 | 9/2014 |
| WO | WO-2014150704 A2 | 9/2014 |
| WO | WO-2014151434 A2 | 9/2014 |
| WO | WO-2014159250 A1 | 10/2014 |
| WO | WO-2014159982 A1 | 10/2014 |
| WO | WO-2014177859 A1 | 11/2014 |
| WO | WO-2014182736 A1 | 11/2014 |
| WO | WO-2014187763 A1 | 11/2014 |
| WO | WO-2014187770 A2 | 11/2014 |
| WO | WO-2014190079 A2 | 11/2014 |
| WO | WO-2014205263 A1 | 12/2014 |
| WO | WO-2015/006652 A1 | 1/2015 |
| WO | WO-2015/009862 A2 | 1/2015 |
| WO | WO-2015028815 A1 | 3/2015 |
| WO | WO-2015040180 A2 | 3/2015 |
| WO | WO-2015042412 A1 | 3/2015 |
| WO | WO-2015058387 A1 | 4/2015 |
| WO | WO-2015/063126 A1 | 5/2015 |
| WO | WO-2015066136 A1 | 5/2015 |
| WO | WO-2015073975 A1 | 5/2015 |
| WO | WO-2015/082652 A1 | 6/2015 |
| WO | WO-2015084544 A1 | 6/2015 |
| WO | WO-2015089711 A1 | 6/2015 |
| WO | WO-2015091258 A1 | 6/2015 |
| WO | WO-2015100361 A1 | 7/2015 |
| WO | WO-2015101651 A1 | 7/2015 |
| WO | WO-2015109616 A1 | 7/2015 |
| WO | WO-2015/124878 A1 | 8/2015 |
| WO | WO-2015/148547 A1 | 10/2015 |
| WO | WO-2015/149647 A1 | 10/2015 |
| WO | WO-2015148649 A2 | 10/2015 |
| WO | WO-2015157893 A1 | 10/2015 |
| WO | WO-2015157901 A1 | 10/2015 |
| WO | WO-2015165067 A1 | 11/2015 |
| WO | WO-2015167629 A1 | 11/2015 |
| WO | WO-2015168828 A1 | 11/2015 |
| WO | WO-2015169127 A1 | 11/2015 |
| WO | WO-2015175979 A1 | 11/2015 |
| WO | WO-2015179292 A1 | 11/2015 |
| WO | WO-2015179641 A1 | 11/2015 |
| WO | WO-2015193456 A1 | 12/2015 |
| WO | WO-2016012769 A1 | 1/2016 |
| WO | WO-2016014652 A1 | 1/2016 |
| WO | WO-2016020675 A1 | 2/2016 |
| WO | WO-2016030661 A1 | 3/2016 |
| WO | WO-2016040575 A1 | 3/2016 |
| WO | WO-2016041114 A1 | 3/2016 |
| WO | WO-2016041140 A1 | 3/2016 |
| WO | WO-2016/062777 A1 | 4/2016 |
| WO | WO-2016050247 A1 | 4/2016 |
| WO | WO-2016054580 A1 | 4/2016 |
| WO | WO-2016058189 A1 | 4/2016 |
| WO | WO-2016063775 A1 | 4/2016 |
| WO | WO-2016065606 A1 | 5/2016 |
| WO | WO-2016071705 A1 | 5/2016 |
| WO | WO-2016071706 A1 | 5/2016 |

OTHER PUBLICATIONS

"How Tobacco Smoke Causes Disease: The Biology and Behavioral Basis for Smoking-Attibutable Disease," U.S. Department of Health and Human Services, 2010.

"Substantially" entry from dictionary.com, printed from internet on Dec. 21, 2020.

Goniewicz, et al., "Nicotine levels in electronic cigarettes," Nicotine Tobacco Research, 15(1), pp. 158-166, Jan. 2013.

(https://www.e-cigarette-forum.com/forum/threads/any-interest-in-determining-nicotine-by-dvap.35922/); blog posts dated: 2009; 8 pgs.; print/retrieval date: Jul. 31, 2014.

3: In vitro toxicity of whole smoke; Food and Chemical Toxicology; 36(3); pp. 191-197; Mar. 1998.

Adam, Thomas, Stefan Mitschke, and Richard R. Baker. "Investigation of tobacco pyrolysis gases and puff-by-puff resolved cigarette smoke by single photon ionisation (SPI)-time-of-flight mass spectrometry (TOFMS)." Beitrage zur Tabakforschung International/Contributions to Tobacco Research 23.4 (2009): 203-226.

Baker et al.; The pyrolysis of tobacco ingredients; J. Anal. Appl. Pyrolysis; 71(1); pp. 223-311; Mar. 2004.

Baker, R., et al., "An overview of the effects of tobacco ingredients on smoke chemistry and toxicity," Food and Chemical Toxicology, 42S, 2004.

Baker, R., et al., "The effect of tobacco ingredients on smoke chemisty. Part II: Casing ingredients," Food and Chemical Toxicology, 42S, 2004.

Bao, M., et al., "An improved headspace solid-phase microextraction method for the analysis of free-base nicotine in particulate phase of mainstream cigarette smoke," Analytica Chimic Acta, 49-54, 2010.

Bastin, R., et al., "Salt Selection and Optimisation Procedures for Pharmaceutical New Checmical Entities," Organic Process Research & Development, 4, 427-435 (2000).

(56) References Cited

OTHER PUBLICATIONS

Bates, "Tobacco Additives: Cigarette Engineering and Nicotine Addiction," ASH UK Report, 1999.
Bertholon, J. F., et al. "Comparison of the aerosol produced by electronic cigarettes with conventional cigarettes and the shisha." Revue des maladies respiratoires 30.9 (2013): 752-757.
Bertholon, J. F., et al. "Electronic cigarettes: a short review." Respiration 86.5 (2013): 433-438.
Bombick et al.; Chemcal and biological studies of a new cigarette that primarily heats tobacco; Part.
Bombick et al.; Chemical and biological studies of a new cigarette that primarily heats tobacco; Part 2: In vitro toxicology of mainstream smoke condesnsate; Food and Chemical Toxicology; 36(3); pp. 183-190; Mar. 1998.
Borgerding et al.; Chemcal and biological studies of a new cigarette that primarily heats tobacco; Part 1: Chemical composition of mainstream smoke; Food and Chemical Toxicology; 36(3); pp. 169-182; Mar. 1998.
Bowen et al.; U.S. Appl. No. 15/101,303 entitled "Nicotine liquid formulations for aerosol devices and methods thereof," filed Jun. 2, 2016.
Bowen et al.; U.S. Appl. No. 14/960,259 entitled "Calibrated Dose Control", filed Dec. 4, 2015.
Bradley et al.; Electronic cigarette aerosol particle size distribution measurements; Inhal. Toxicol.; 24(14); pp. 976-984; Dec. 2012.
Brown, Christopher J., et al., "Electronic cigarettes: product characterisation and design considerations." Tobacco control 23.suppl 2 (2014): ii4-ii10.
Brown, Christopher, et al.,"Caffeine and Cigarette Smoking: Behavioral, Cardiovascular, and Metabolic Interactions," Pharmacology Biochemistry and Behavior, vol. 34, pp. 565-570, 1989.
Bullen et al.; Effect of an electronic nicotine delivery device (e cigarette) on desire to smoke and withdrawal, user preferences and nicotine delivery: randomised cross-over trial; Tobacco Control; 19(2); pp. 98-103; Apr. 2010.
Bullen, Chris, et al. "Study protocol for a randomised controlled trial of electronic cigarettes versus nicotine patch for smoking cessation." BMC public health 13.1 (2013): 210.
Bullen, Christopher, et al. "Effect of an electronic nicotine delivery device (e cigarette) on desire to smoke and withdrawal, user preferences and nicotine delivery: randomised cross-over trial." Tobacco control 19.2 (2010): 98-103.
Burch et al.; Effect of pH on nicotine absorption and side effects produced by aerosolized nicotine; Journal of Aerosol Medicine: Deposition, Clearance, and Effects in the Lung; 6(1); pp. 45-52; 1993.
Burch, et al., "Effect of pH on nicotine absorption and side effects produced by areosolized nicotine," Journal of Aerosol Medicine: Deposition, Clearance, and Effects in the Lung, 6(1), pp. 45-52. 1993.
Burn et al., "Action of Nicotine on the Heart", Excretion of Piperazine Salts, British Medical Journal, Jan. 18, 1958, pp. 137-139.
Cahn, Zachary, et al., "Electronic cigarettes as a harm reduction strategy for tobacco control: a step forward or a repeat of past mistakes?." Journal of public health policy 32.1 (2011): 16-31.
Caldwell, B., et al., "A Systematic Review of Nicotine by Inhalation: Is There a Role for the Inhaled Route?," Nicotine & Tobacco Research, pp. 1-13 (2012).
Callicutt, C.H., "The role of ammonia in the transfer of nicotine from tobacco to mainstream smoke," Regulatory Toxicology and Pharmacology, 46, 2006.
Caponnetto, Pasquale, et al. "EffiCiency and Safety of an eLectronic cigAreTte (ECLAT) as tobacco cigarettes substitute: a prospective 12-month randomized control design study." PloS one 8.6 (2013): e66317.
Caponnetto, Pasquale, et al. "The emerging phenomenon of electronic cigarettes." Expert review of respiratory medicine 6.1 (2012): 63-74.
Capponnetto et al.; Successful smoking cessation with cigarettes in smokers with a documented history of recurring relapses: a case series; Journal of Medical Case Reports; 5(1); 6 pages; (year of pub. sufficiently earlier than effective US filing date and any foreign priority date); 2011.
Cheng, Tianrong. "Chemical evaluation of electronic cigarettes." Tobacco control 23.suppl 2 (2014): ii11-ii17.
Cig Buyer.com 2013 Inside E-Cigarette Liquids and Vapor.
Cisternino, S., et al., "Coexistence of Passive and Proton Anitporter-Mediated Processes in Nicotine Transport at the Mouse Blood-Brain Barrier," The AAPS Journal, vol. 15, No. 2, Apr. 2013.
Clayton, et al., "Spectroscopic investigations into the acid-base properties of nicotine at different temperatures", Analytical Methods, 2013, pp. 81-88, vol. 5.
Dawkins, Lynne, et al. "The electronic-cigarette: effects on desire to smoke, withdrawal symptoms and cognition." Addictive behaviors 37.8 (2012): 970-973.
Dawkins, Lynne, et al., "Acute electronic cigarette use: nicotine delivery and subjective effects in regular users," Psychopharmacology, 2013.
Dawkins, Lynne, John Turner, and Eadaoin Crowe. "Nicotine derived from the electronic cigarette improves time-based prospective memory in abstinent smokers." Psychopharmacology 227.3 (2013): 377-384.
Definition of "aerosol", Merriam-Webster Dictionary, [online], no date, retrieved from the Internet, [retrieved Jun. 8, 2017], <URL: https://www.merriam-webster.com/dictionary/aerosol>.
Dezelic, M., et al., "Determination of structure of some salts of nicotine, pyridine and N-methylpyrrolidine on the basis of their infra-red spectra," Spectrochimica Acta, vol. 23A, 1967.
Dixon, M., "On the Transfer of Nicotine from Tobacco to the Smoker. A Brief Review of Ammonia and "pH" Factors," Contributions to Tobacco Research, vol. 19, No. 2, Jul. 2000.
Dong, J.Z., et al., "A Simple Technique for Determining the pH of Whole Cigarette Smoke," Contributions to Tobacco Research, vol. 19, No. 1, Apr. 2000.
Drummond, M. Bradley, et al., "Electronic cigarettes. Potential harms and benefits." Annals of the American Thoracic Society 11.2 (2014): 236-242.
E-Cigarette Forum; pg-gv-peg (discussion/posting); retrieved from the internet: <https://e-cigarette-forum.com/forum/threads/pg-vg-peg.177551;> 7 pgs.; Apr. 8, 2011.
ECF; Any interest in determining nicotine—by DVAP.
Effros, R., et al., "The In Vivo pH of the Extravascular Space of the Lung," The Journal of Clinical Investigation, vol. 48, 1969.
Eissenberg, Thomas. "Electronic nicotine delivery devices: ineffective nicotine delivery and craving suppression after acute administration." Tobacco control 19.1 (2010): 87-88.
Etter, Jean-Francois, et al., "Analysis of refill liquids for electronic cigarettes." Addiction 108.9 (2013): 1671-1679.
Etter, Jean-Francois. "Levels of saliva cotinine in electronic cigarette users." Addiction 109.5 (2014): 825-829.
Farsalinos et al.; Electronic cigarettes do not damage the heart; European Society of Cardiology; 4 pages; retrieved from the internet (http://www.escardio.org/The-ESC/Press-Office/Press-releases/Electronic-cigarettes-do-not-damage-the-heart); Aug. 25, 2012.
Farsalinos, Konstantinos E., et al. "Characteristics, perceived side effects and benefits of electronic cigarette use: a worldwide survey of more than 19,000 consumers." International journal of environmental research and public health 11.4 (2014): 4356-4373.
Farsalinos, Konstantinos E., et al. "Evaluating nicotine levels selection and patterns of electronic cigarette use in a group of "vapers" who had achieved complete substitution of smoking." Substance abuse: research and treatment 7 (2013): SART-512756.
Farsalinos, Konstantinos E., et al. "Impact of flavour variability on electronic cigarette use experience: an internet survey." International journal of environmental research and public health 10.12 (2013): 7272-7282.
Farsalinos, Konstantinos E., et al. "Nicotine absorption from electronic cigarette use: comparison between first and new-generation devices." Scientific reports 4 (2014): 4133.

(56) References Cited

OTHER PUBLICATIONS

Farsalinos, Konstantinos E., et al., "Safety evaluation and risk assessment of electronic cigarettes as tobacco cigarette substitutes: a systematic review." Therapeutic advances in drug safety 5.2 (2014): 67-86.

Flouris et al.; Acute impact of active and passive electronic cigarette smoking on serum cotinine and lung function; Inhal. Toxicol.; 25(2); pp. 91-101; Feb. 2013.

Food & Drug Administration; Warning letter to the Compounding Pharmacy; retrieved Oct. 10, 2014 from http://www.fda.gov/ICECI/EnfocementActions/WarningLetters/2002/ucm144843.htm; 3 pgs.; Apr. 9, 2002.

Fournier, J., "Thermal Pathways for the Transfer of Amines, Including Nicotine, to the Gas Phase and Aerosols," Heterocycles, vol. 55, No. 1, 2001.

Gonda, I., et al. "Smoking cessation approach via deep lung delivery of 'clean'nicotine." RDD Europe (2009): 57-61.

Goniewicz, Maciej L., et al., "Nicotine content of electronic cigarettes, its release in vapour and its consistency across batches: regulatory implications." Addiction 109.3 (2014): 500-507.

Grotenhermen, et al., Developing science-based per se limits for driving under the influence of cannabis (DUIC): findings and recommendations by an expert panel; retreived Feb. 9, 2017 from (http://www.canorml.org/healthfacts/DUICreport.2005.pdf); Sep. 2005.

Harris, Mark. "Warning cigarettes may be about to become fashionable again." Engineering & Technology 6.1 (2011): 38-31.

Harvest Vapor; American Blend Tobacco (product info.); retrieved from the internet (http://harvestvapor.com/); 2 pgs.; print/retrieval date: Oct. 10, 2014.

Henningfield, et al., "Tobacco Control", 1995, pp. 57-61, vol. 4.

Heyder, J., "Alveolar deposition of inhaled particles in humans," American Industrial Hygiene Association Journal, 43:11, 864-866, 2010.

https://www.industrydocumentslibrary.ucsf.edu/tobacco/docs/ytyg0100.

Hurt et al.; Treating tobacco dependence in a medical setting; CA: A Cancer Journal for Clinicians; 59(5); pp. 314-326; Sep. 2009.

Hurt, R., et al., "Prying Open the Door to the Tobacco Industry's Secrets About Nicotine," The Journal of the American Medical Association, vol. 280, 1998.

Inchem; Benzoic Acid; JECFA Evaluation Summary; retrieved Oct. 10, 2014 from http://www.inchem.org/documents/jecfa/feceval/jec_184.htm; 2 pgs . . . ; May 28, 2005.

Inchem; Levulinic Acid; JECFA Evaluation Summary; retrieved Oct. 10, 2014 from http://www.inchem.org/documents/jecfa/feceval/jec_1266.htm; 1 pg.; Mar. 10, 2003.

Inchem; Pyruvic Acid; JECFA Evaluation Summary; retrieved Oct. 10, 2014 from http://www.inchem.org/documents/jecfa/feceval/jec_2072.htm; 1 pg.; Jan. 29, 2003.

Inchem; Sorbic Acid; JECFA Evaluation Summary; retrieved Oct. 10, 2014 from http://www.inchem.org/documents/jecfa/feceval/jec_2181.htm; 1 pg.; May 29, 2005.

Ingebrethsen et al.; Electronic cigarette aerosol particle size distribution measurements; Inhalation Toxicology; 24(14); pp. 976-984; Dec. 2012.

Keithly, Lois., et al., "Industry research on the use and effects of levulinic acid: A case study in cigarette additives," Nicotine & Tobacco Research vol. 7, No. 5, 761-771, 2005.

Kosmider, L., et al. "Electronic cigarette—a safe substitute for tobacco cigarette or a new threat?." Przeglad lekarski 69.10 (2012): 1084-1089. [including English language translation thereof].

Kuo et al.; Appendix D: Particle size—U.S. sieve size and tyler screen mesh equivalents; Applications of Turbulent and Multiphase Combustion; John Wiley & Sons, Inc.; pp. 541-543; May 1, 2012.

Lauterbach, J.H, "Comparison of Mainstream Cigarette Smoke pH With Mainstream E-Cigarette Aerosol pH" Tob. Sci. Res. Conf., 2013, 67, abstr. 78. 2013.

Lauterbach, J.H., "A Critical Assessment of Recent Work on the Application of Gas/Particle Partitioning Theories to Cigarette Smoke," Contributions to Tobacco Research, vol. 19, No. 2, Jul. 2000.

Lauterbach, J.H., "Comment on Gas/Particle Partitioning of Two Acid-Base Active Compounds in Mainstream Tobacco Smoke: Nicotine and Ammonia," J. Agric. Food Chem., vol. 58, No. 16, 2010.

Lauterbach, J.H., "Free-base nicotine in tobacoo products. Part 1. Determination of free-base nicotine in the particulate phase of mainstream cigarette smoke and the relevance of these findings to product design parameters," Regulatory Toxicology and Pharmacology, 2010.

Lauterback (2013) "GC-MS analysis of e-liquids taken from e-cigarettes and e-liquids (e-juice) before use in e-cigarettes" Presentation Slides Coresta.

Lee, L.-Y., et al., "Airway irritation and cough evoked by inhaled cigarette smoke: Role of neuronal nicotinic acetylcholine receptors," Pulmonary Pharmacology & Therapeutics, vol. 20, 2007.

Leffingwell, et al., "Basic chemical constituents of tobacco: production, chemistry and Technology", Blackwell Science, 1999.

Leffingwell, J., et al., "Tobacco Flavoring for Smoking Products," R.J. Reynolds Tobacco Company, 1972.

Lim, Heung Bin, et al., "Inhallation of e-cigarette cartridge solution aggravates allergen-induced airway inflammation and hyperresponsiveness in mice." Toxicological research 30.1 (2014): 13.

Lippiello, P., et al., "Enhancement of Nicotine Binding to Nicotinic Receptors by Nicotine Levulinate and Levulinic Acid," 1989.

Lux, J.E., et al., "Subjective Responses to Inhaled and Intravenous Injected Nicotine," American Society for Clinical Pharmacology and Therapeutics, 1988.

Lux, J.E., et al., :Generation of a submicrometre nicotine aerosol for inhalation, Med. & Biol. Eng. & Comput. 26, 232-234, 1988.

Monseeset al.; U.S. Appl. No. 15/257,760 entitled "Vaporizer apparatus," filed Sep. 6, 2016.

MacDougall, James., et al., "Selective Cardiovascular Effects of Stress and Cigarette Smoking," Journal of Human Stress, 9:3. 13-21, 1983.

Maier, et al., "Polypropylene: the defintive user's guide and databook", 1998.

McCann et al.; Detection of carcinogens as mutagens in the salmonella/microsome test: Assay of 300 chemicals: Discussion; Proc. Nat. Acad. Sci.; 73(3); pp. 950-954; Mar. 1976.

McQueen, Amy, et al., "Interviews with "vapers": implications for future research with electronic cigarettes." Nicotine & Tobacco Research 13.9 (2011): 860-867.

McRobbie, Hayden, et al. "Electronic cigarettes for smoking cessation and reduction." Cochrane Database Syst. Rev 12 (2012).

Mirriam-Webster Online Dictionary; Lighter; retrieved Jan. 4, 2013 from the internet: (http://www.merriam-webster.com/dictionary/lighter?show=0&t=1357320593); 2 pgs.; print date: Jan. 4, 2013.

Monsees et al.; U.S. Appl. No. 15/257,748 entitled "Cartridge for use with a vaporizer device," filed Sep. 6, 2016.

Monsees et al.; U.S. Appl. No. 15/165,954 entitled "Devices for vaporization of a substance," filed May 26, 2016.

Monsees et al.; U.S. Appl. No. 15/165,972 entitled "Portable devices for generating an inhalable vapor," filed May 26, 2016.

Monsees et al.; U.S. Appl. No. 15/166,001 entitled "Electronic vaporization device," filed May 26, 2016.

Monsees et al.; U.S. Appl. No. 15/257,768 entitled "Vaporizer apparatus," filed Sep. 6, 2016.

Monsees et al.; U.S. Appl. No. 15/261,823 entitled "Low temperature electronic vaporization device and methods," filed Sep. 9, 2016.

Monsees, J.; U.S. Appl. No. 12/115,400 entitled "Method and System for Vaporization of a Substance", filed May 5, 2008.

Nicoli et al.; Mammalian tumor xenografts induce neovascularization in Zebrafish embryos; Cancer Research; 67(7); pp. 2927-2931; Apr. 1, 2007.

Nicotine Salts. RJ Reynolds Records. Nov. 9, 1990.

Oldendorf, W., et al., "Blood-brain barrier penetration abolished by N-methyl quaternization of nicotine," Proc. Natl. Acad. Sci, vol. 90, pp. 307-311, 1993.

Oldendorf, W., et al., "pH Dependence of Blood-Brain Barrier Permeability to Lactate and Nicotine," Stroke, vol. 10, No. 5, 1979.

Omole, Olufemi Babatunde, et al., "Review of alternative practices to cigarette smoking and nicotine replacement therapy: how safe are they?. " South African Family Practice 53.2 (2011): 154-160.

(56) References Cited

OTHER PUBLICATIONS

Pachke, T., et al., "Effects of Ingredients on Cigarette Smoke Composition and Biological Activity: A Literature Overview," Contributions to Tobacco Research, vol. 20, No. 2, Aug. 2002.
Pankow, et al., "Conversion of Nicotine in Tobacco Smoke to Its Volatile and Available Free-Base form Through the Action of Gaseous Ammonia," Eniron. Sci. Technol. 31 (8), 1997.
Pankow, James F. "A consideration of the role of gas/particle partitioning in the deposition of nicotine and other tobacco smoke compounds in the respiratory tract." Chemical research in toxicology 14.11 (2001): 1465-1481.
Perfetti, "Structural study of nicotine salts," Beitrage Zur Tabakforschung International, Contributions to Tobacco Research, 12(2), pp. 43-54. Jun. 1983.
Perfetti, T., "Investigation of Nicotine Transfer to Mainstream Smoke I. Synthesis of Nicotine Salts," 1978.
Perfetti, Transfer of Nicotine salts to mainstream smoke (2000) https://www.industrydocumentslibrary.ucstedu/tobacco/docs/#id=rzwp0187.
Polosa, Riccardo, et al. "A fresh look at tobacco harm reduction: the case for the electronic cigarette." Harm reduction journal 10.1 (2013): 19.
Polosa, Riccardo, et al. "Effect of smoking abstinence and reduction in asthmatic smokers switching to electronic cigarettes: evidence for harm reversal." International journal of environmental research and public health 11.5 (2014): 4965-4977.
Polosa, Riccardo, et al. "Effectiveness and tolerability of electronic cigarette in real-life: a 24-month prospective observational study." Internal and emergency medicine 9.5 (2014): 537-546.
Polosa, Riccardo, et al., "Effect of an electronic nicotine delivery device (e-Cigarette) on smoking reduction and cessation: a prospective 6-month pilot study." BMC public health 11.1 (2011): 786.
Prignot, J., "Electronic Nicotine Delivery Systems (Electronic Cigarettes, Cigars, Pipes)," Louvain Medical, V. 132, No. 10, Dec. 2013. [including English language translation thereof].
U.S. Appl. No. 61/826,318, filed May 22, 2013.
U.S. Appl. No. 61/856,286, filed Jul. 19, 2013.
U.S. Appl. No. 61/856,374, filed Jul. 19, 2013.
U.S. Appl. No. 61/891,626, filed Oct. 16, 2013.
U.S. Appl. No. 61/969,650, filed Mar. 24, 2014.
U.S. Appl. No. 61/971,340, filed Mar. 27, 2014.
Riggs, et al., "The Thermal Stability of Nicotine Salts," R.J. Reynolds Tobacco Company, 2000.
Robertson, C., et al., "In their own words: an epoch of deceit and deception," Chapter 5 (find out from which book).
Rose, J., "Nicotine and nonnicotine factors in cigarette addiction," Psychopharmacology, 184:274-285, 2006.
Rose, J., "Pulmonary Delivery of Nicotine Pyruvate: Sensory and Pharmacokinetic Characteristics," Experimental and Clinical Psychopharmacology, vol. 18, No. 5, 2010.
Sahu, S.K., et al., "Particle Size Distribution of Mainstream and Exhaled Cigarette Smoke and Predictive Deposition in Human Repiratory Tract," Aerosol and Air Quality Research, 13: 324-332, 2013.
Scenihr, "Addictiveness and Attractiveness of Tobacco Additives," Scientific Committee on Emerging and Newly Identified Health Risks, Nov. 12, 2010.
Schripp, Tobias, et al. "Does e-cigarette consumption cause passive vaping?." Indoor air 23.1 (2013): 25-31.
Schroeder, Megan J., et al., "Electronic cigarettes and nicotine clinical pharmacology." Tobacco control 23.suppl 2 (2014): ii30-ii35.
Seeman et al.; The form of nicotine in tobacco. Thermal transfer of nicotine and nicotine acid salts to nicotine in the gas phase; J Aric Food Chem.; 47(12); pp. 5133-5145; Dec. 1999.
Seeman, J., "Possible Role of Ammonia on the Deposition, Retention, and Absorption of Nicotine in Humans while Smoking," Chemical Research in Toxicology, 20, 2007.

Seeman, J., "Using 'Basic Principles' to Understand Complex Science: Nicotine Smoke Chemistry and Literature Analogies," Journal of Chemical Education, vol. 82, No. 10, 2005.
Seeman, J., et al., "On the Deposition of Volatiles and Semivolatiles from Cigarette Smoke Aerosols: Relative Rates of Transfer of Nicotine and Ammonia from Particles to the Gas Phase," Chemical Research in Toxicology, 17, 2004.
Seeman, J., et al., "The possible role of ammonia toxicity on the exposure, deposition, retention, and the bioavailability of nicotine during smoking," Food and Chemical Toxicology, 46, 2008.
Sensabaugh, A.J., et al., "A New Technique for Determining the pH of Whole Tobacco Smoke," Tobacco Science.
Shahab, L., et al., "Novel Delivery Systems for Nicotine Replacement Therapy as an Aid to Smoking Cessation and for Harm Reduction: Rationale, and Evidence for Advantages over Existing Systems," CNS Drugs, 27: 1007-1019, 2013.
Snowdon, Christopher. "Harm reduction and tobacco: a new opportunity or a step too far?." Drugs and Alcohol Today 13.2 (2013): 86-91.
Stepanov, et al., "Bringing attention to e-cigarette pH as an important element for research and regulation", Tob. Control, May 14, 2014, vol. 24, No. 4.
Stevenson, T., et al., "The Secret and Soul of Marlboro," Public Health Then and Now, American Journal of Public Health, vol. 98, No. 7, 2008.
Teague, "Implications and Activites Arising from Correlation of Smoke pH with Nicotine Impact, Other Smoke Qualities and Cigarette Sales," 1983.
Tomar, S., et al., "Review of the evidence that pH is a determinant of nicotine dosage from oral use of smokeless tobacco," Tobacco Control, 6:219-225, 1997.
Torikai et al.; Effects of temperature, atmosphere and pH on the generation of smoke compounds duriung tobacco pyrolysis; Food and Chemical Toxicology; 42(9); pp. 1409-1417; Sep. 2004.
Torrie, B., "Nicotine inhaler gives instant 'hit'," 2 pages (2013), available at http://www.stuff.co.nz/national/health/8822875/Nicotine-inhaler-gives-instant-hit.
Travell, J., "The Influence of the Hydrogen Ion Concentration on the Absorption of Alkaloids from the Stomach," The Journal of Pharmacology, Jan. 1940.
Trehy, Michael L., et al. "Analysis of electronic cigarette cartridges, refill solutions, and smoke for nicotine and nicotine related impurities." Journal of Liquid Chromatography & Related Technologies 34.14 (2011): 1442-1458.
Uchiyama, Shigehisa, et al. "Determination of carbonyl compounds generated from the E-cigarette using coupled silica cartridges impregnated with hydroquinone and 2, 4-dinitrophenylhydrazine, followed by high-performance liquid chromatography." Analytical sciences 29.12 (2013): 1219-1222.
Vansickel et al.; A clinical laboratory model for evaluating the acute effects of electronic cigarettes: Nicotine delivery profile and cardiovascular and subjective effects; Cancer Epidemiology Biomarkers Prevention; 19(8); pp. 1945-1953; (online) Jul. 20, 2010.
Vansickel, Andrea R., et al. "A clinical laboratory model for evaluating the acute effects of electronic "cigarettes": nicotine delivery profile and cardiovascular and subjective effects." Cancer Epidemiology and Prevention Biomarkers 19.8 (2010): 1945-1953.
Vansickel, Andrea Rae, et al., "Electronic cigarettes: effective nicotine delivery after acute administration." Nicotine & Tobacco Research 15.1 (2012): 267-270.
Vansickel, et al., "Electronic cigarettes: effective nicotine delivery after acute administration," Nicotine & Tobacco Research, 15(1), pp. 267-270. Jan. 2013.
Ward; Green leaf threshing and redrying tobacco; Section 10B; in Tobacco Production, Chemistry and Technology; Davis and Nielsen (Eds.); Blackwell Science Ltd.; pp. 330-333; Jul. 15, 1999.
Wayne, G., et al., "Brand differences of free-base nicotine delivery in cigarette smoke: the view of the tobacco industry documents," Tobacco Control, 15:189-198, 2006.
Weiss, G., "The Effect of pH on Nicotine-Induced Contracture and Ca45 Movements in Frog Sartorius Muscle," The Journal of Pharmacology and Experimental Therapeutics, vol. 154, No. 3, 1966.

(56) References Cited

OTHER PUBLICATIONS

Wells; Glycerin as a constituent of cosmetics and toilet preparations; Journal of the Society of Cosmetic Chemists; 9(1); pp. 19-25; Jan. 1958.
World Health Organization, :Health Effects of Interations Between Tobacco Use and Exposure to Other Agents, Environmental Health Criteria 211, 83 pages (1999), available at http://www.inchem.org/documents/ehc/ehc/ehc211.htm.
Wynn III, William P., et al. "The pharmacist "toolbox" for smoking cessation: a review of methods, medicines, and novel means to help patients along the path of smoking reduction to smoking cessation." Journal of pharmacy practice 25.6 (2012): 591-599.
YouTube; Firefly Vaporizor Review w/ Usage Tips by the Vape Critic; retrieved from the internet (http://www.youtube.com/watch?v=1J38NOAV7wl); 1 pg.; published Dec. 10, 2013; download/print date: Feb. 18, 2015.
Zenzen, Volker, et al. "Reduced exposure evaluation of an Electrically Heated Cigarette Smoking System. Part 2: Smoke chemistry and in vitro toxicological evaluation using smoking regimens reflecting human puffing behavior." Regulatory Toxicology and Pharmacology 64.2 (2012): S11-S34.
Zhang et al.; In vitro particle size distributions in electronic and conventional cigarette aerosols suggest comparable deposition patterns; Nicotine Tobacco Research; 15(2); pp. 501-508; Feb. 2013.
Zhang, Yaping, et al., "In vitro particle size distributions in electronic and conventional cigarette aerosols suggest comparable deposition patterns." Nicotine & Tobacco Research 15.2 (2012): 501-508.
Burn and Rand, Action of Nicotine on the Heart, British Medical Journal, pp. 137-139 (Jan. 18, 1958).
E-Cigarette Forum: pg-gv-peg (discussion/posting); retrived from the internet: https://e-cigarette-forum.com/forum/threads/pg-vg-peg. 177551, 7 pages (Apr. 8, 2011).
Notice of Opposition to European Patent No. 2 993 999 B1 by JT International S.A., 38 pages (Oct. 26, 2021).
Notice of Opposition to European Patent No. 2 993 999 B1 by Nicoventures Trading Limited, 26 pages (Oct. 26, 2021).
Notice of Opposition to European Patent No. 2 993 999 B1 by Philip Morris Products S.A., 22 pages (Oct. 27, 2021).
Preliminary Opinion of the Opposition Division to the Oppositions in European Patent No. 2 993 999 B1, 17 pages (Aug. 30, 2022).
Interlocutory Decision in Opposition Proceedings received for European Application No. 14794206.4 mailed on May 19, 2023, 25 pages.
Duell, Nicotine in Tobacco Product Aerosols: 'it's Déjà Vu All Over Again', Tobacco Control, 7 pages. 2020.
Electronic Cigarette,Merriam-Webster,1 page.
Influence of pH on Absorption of Nicotine from Urinary Bladder and Subcutaneous Tissues.
Inventor Bowen to Ploom—61-820,128, Assignment of Jun. 3, 2013,2 pages.
Inventors Bowen, Xing to Ploom—61-912,507, Assignment of May 1, 2014,4 pages.
IUPAC Compendium of Chemical Terminology, 2nd ed. (the "Gold Book").
Pax to JUUL, Recorded Change of Name of Aug. 14, 2017,11 pages.
Pax to JUUL, Recorded Corrective Assignment of Aug. 6, 2018,15 pages.
Ploom to Pax, Recorded Assignment of Mar. 3, 2015,8 pages.
(2014) The Art of Medicine: Electronic Cigarettes and History.
(2016) The Efficacy and Short-Term Effects of Electronic Cigarettes as a Method for Smoking Cessation: A Systematic Review and a Meta-Analysis.
(2015) Web record in respect of U.S. Appl. No. 14/271,071, 2 pages.
Hatton et al.; U.S. Appl. No. 15/396,584 entitled "Leak-resistant vaporizer cartridges for use with cannabinoids," filed Dec. 31, 2016.
Clayton, P. et al., "Use of chiroptical spectroscopy to determine the ionisation status of (S)- nicotine in e-cigarette formulations", Presentation Coresta Gongress, (Oct. 16, 2014), 2 pages.
Chen, et al., (Aug. 2011), "Organic Chemistry," Beijing Institute of Technology Press, 251-252.
Declaration by Dr. Bradley James Ingebrethsen, on Sep. 4, 2015, 64 pages.
Goldenson, et al., (2020) "Nicotine Uptake Following the Use of E-liquids with Different Organic Acid Salts and Nicotine Concentrations among Adult Smokers", Juul Labs, Inc. and Pinney Associates, Inc., 1 page.
Shao, et al., (Dec. 13, 2012) "Nicotine Delivery to Rats via Lung Alveolar Region-Targeted Aerosol Technology Produces Blood Pharmacokinetics Resembling Human Smoking", Nicotine Tob Res., vol. 15, No. 7, pp. 1248-1258.

\* cited by examiner

NICOTINE SALT FORMULATIONS FOR AEROSOL DEVICES AND METHODS THEREOF

CROSS REFERENCE

This application is a continuation of U.S. application Ser. No. 14/925,961 filed Oct. 28, 2015, issued as U.S. Pat. No. 10,952,468, which is a continuation of U.S. application Ser. No. 14/271,071 filed May 6, 2014, which claims the benefit of priority to U.S. Application No. 61/912,507 filed Dec. 5, 2013, and U.S. Application No. 61/820,128 filed May 6, 2013, which are incorporated herein by reference in their entireties. This application is related to U.S. application Ser. No. 14/512,311, issued as U.S. Pat. No. 9,215,895, and to U.S. application Ser. No. 14/925,968.

SUMMARY OF THE INVENTION

Provided herein is a method of delivering nicotine to a user comprising operating an electronic cigarette to a user wherein the electronic cigarette comprises a nicotine salt formulation comprising a nicotine salt in a biologically acceptable liquid carrier wherein an acid used to form said nicotine salt is characterized by vapor pressure >20 mmHg at 200° C., and inhaling an aerosol generated from the nicotine salt formulation heated by the electronic cigarette.

Provided herein is a method of delivering nicotine to a user comprising operating an electronic cigarette to a user wherein the electronic cigarette comprises a nicotine salt formulation comprising a nicotine salt in a biologically acceptable liquid carrier wherein an acid used to form said nicotine salt is characterized by vapor pressure of about 20 to 200 mmHg at 200° C., and inhaling an aerosol generated from the nicotine salt formulation heated by the electronic cigarette.

Provided herein is a method of delivering nicotine to a user comprising operating an electronic cigarette wherein the electronic cigarette comprises a nicotine salt formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point, and inhaling an aerosol generated from the nicotine salt formulation heated by the electronic cigarette.

Provided herein is a method of delivering nicotine to a user comprising providing an electronic cigarette to a user wherein the electronic cigarette comprises a nicotine salt formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point, and inhaling an aerosol generated from the nicotine salt formulation heated by the electronic cigarette.

Provided herein is a method of delivering nicotine to the blood of a user, said method comprising providing an aerosol that is inhaled by the user from an electronic cigarette that comprises a nicotine salt formulation wherein providing the aerosol comprises the electronic cigarette heating the formulation thereby generating the aerosol, wherein the aerosol is effective in delivering a level of nicotine in the blood of the user that is at least 5 ng/mL at about 1.5 minutes after a first puff of ten puffs of the aerosol, each puff taken at 30 second intervals.

Provided herein is a nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is characterized by vapor pressure >20 mmHg at 200° C.

Provided herein is a nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is characterized by vapor pressure of about 20 to 200 mmHg at 200° C.

Provided herein is a nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

Provided herein is a nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

Provided herein is a nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is characterized by vapor pressure >20 mmHg at 200° C.

Provided herein is a nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is characterized by vapor pressure of about 20 to 200 mmHg at 200° C.

Provided herein is a nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

Provided herein is a nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

Provided herein is a nicotine salt liquid formulation for use in an electronic cigarette the nicotine salt liquid formulation comprising a nicotine salt in a biologically acceptable liquid carrier wherein an acid used to form said nicotine salt is characterized by vapor pressure >20 mmHg at 200° C.

Provided herein is a nicotine salt liquid formulation for use in an electronic cigarette the nicotine salt liquid formulation comprising a nicotine salt in a biologically acceptable liquid carrier wherein an acid used to form said nicotine salt is characterized by vapor pressure of about 20 to 200 mmHg at 200° C.

Provided herein is a nicotine salt liquid formulation for use in an electronic cigarette the nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

Provided herein is a nicotine salt liquid formulation for use in an electronic cigarette the nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

Provided herein is a use of a nicotine salt formulation for delivery of nicotine to a user from an electronic cigarette wherein the nicotine salt formulation comprises a nicotine salt in a biologically acceptable liquid carrier wherein an acid used to form said nicotine salt is characterized by vapor pressure >20 mmHg at 200° C., and the nicotine salt formulation is heated by the electronic cigarette to generate an aerosol inhalable by the user.

Provided herein is a use of a nicotine salt formulation for delivery of nicotine to a user from an electronic cigarette wherein the nicotine salt formulation comprises a nicotine salt in a biologically acceptable liquid carrier wherein an acid used to form said nicotine salt is characterized by vapor pressure of about 20 to 200 mmHg at 200° C., and the nicotine salt formulation is heated by the electronic cigarette to generate an aerosol inhalable by the user.

Provided herein is a use of a nicotine salt formulation for delivery of nicotine to a user from an electronic cigarette wherein the nicotine salt formulation comprises a nicotine salt in a biologically acceptable liquid carrier wherein an acid used to form said nicotine salt is further characterized by a melting point <160° C., a boiling point >160° C., and at least a 50-degree difference between the melting point and the boiling point, and the nicotine salt formulation is heated by the electronic cigarette to generate an aerosol inhalable by the user.

Provided herein is a use of a nicotine salt formulation for delivery of nicotine to the blood of a user from an electronic cigarette, wherein the nicotine salt formulation in the electronic cigarette is heated to form an aerosol which delivers a level of nicotine in the blood of the user that is at least 5 ng/mL at about 1.5 minutes after a first puff of ten puffs of the aerosol, each puff taken at 30 second intervals.

Provided herein is a use of a nicotine salt formulation for delivery of nicotine to a user from an electronic cigarette wherein the nicotine salt formulation comprises a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point, and the nicotine salt formulation is heated by the electronic cigarette to generate an aerosol inhalable by the user.

Provided herein is a cartomizer for an electronic cigarette comprising:
  a nicotine salt liquid formulation comprising a nicotine salt in a biologically acceptable liquid carrier wherein an acid used to form said nicotine salt is characterized by vapor pressure >20 mmHg at 200° C.;
  an atomizer comprising a heating element in fluid communication with the nicotine salt liquid formulation; and
  a fluid storage compartment that stores the nicotine salt liquid formulation.

Provided herein is a cartomizer for an electronic cigarette comprising:
  a nicotine salt liquid formulation comprising a nicotine salt in a biologically acceptable liquid carrier wherein an acid used to form said nicotine salt is characterized by vapor pressure of about 20 to 200 mmHg at 200° C.;
  an atomizer comprising a heating element in fluid communication with the nicotine salt liquid formulation; and
  a fluid storage compartment that stores the nicotine salt liquid formulation.

Provided herein is a cartomizer for an electronic cigarette comprising:
  a nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point;
  an atomizer comprising a heating element in fluid communication with the nicotine salt liquid formulation; and
  a fluid storage compartment that stores the nicotine salt liquid formulation.

Provided herein is a cartomizer for an electronic cigarette comprising:
  a nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point;
  an atomizer comprising a heating element in fluid communication with the nicotine salt liquid formulation; and
  a fluid storage compartment that stores the nicotine salt liquid formulation.

Provided herein is an electronic cigarette for generating an inhalable aerosol comprising:
  a fluid storage compartment;
  a heater; and
  a nicotine salt liquid formulation in the fluid storage compartment, the liquid formulation comprising a nicotine salt in a biologically acceptable liquid carrier wherein an acid used to form said nicotine salt is characterized by vapor pressure >20 mmHg at 200° C.;

a battery; and a mouthpiece.

Provided herein is an electronic cigarette for generating an inhalable aerosol comprising:

a fluid storage compartment;

a heater; and a nicotine salt liquid formulation in the fluid storage compartment, the liquid formulation comprising a nicotine salt in a biologically acceptable liquid carrier wherein an acid used to form said nicotine salt is characterized by vapor pressure of about 20 to 200 mmHg at 200° C.;

a battery; and a mouthpiece.

Provided herein is an electronic cigarette for generating an inhalable aerosol comprising:

a fluid storage compartment;

a heater; and a nicotine salt liquid formulation in the fluid storage compartment, the liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point;

a battery; and a mouthpiece.

Provided herein is an electronic cigarette for generating an inhalable aerosol comprising:

a fluid storage compartment;

a heater; and a nicotine salt liquid formulation in the fluid storage compartment, the liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point;

a battery; and a mouthpiece.

Provided herein is a cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure >20 mmHg at 200° C.

Provided herein is a cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure of about 20 to 200 mmHg at 200° C.

Provided herein is a cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

Provided herein is a cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

Provided herein is a kit comprising:

(a) an electronic cigarette for generating an inhalable aerosol comprising
  i. a device body comprising a cartridge receptacle;
  ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure >20 mmHg at 200° C.;
  iii. a heater;
  iv. a battery; and
  v. a mouthpiece; and (b) instructions for using the electronic cigarette to generate an inhalable aerosol.

Provided herein is a kit comprising:

(a) an electronic cigarette for generating an inhalable aerosol comprising
  i. a device body comprising a cartridge receptacle;
  ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure of about 20 to 200 mmHg at 200° C.;
  iii. a heater;
  iv. a battery; and
  v. a mouthpiece; and (b) instructions for using the electronic cigarette to generate an inhalable aerosol.

Provided herein is a kit comprising:

(a) an electronic cigarette for generating an inhalable aerosol comprising
  i. a device body comprising a cartridge receptacle;
  ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point;
  iii. a heater;
  iv. a battery; and
  v. a mouthpiece; and (b) instructions for using the electronic cigarette to generate an inhalable aerosol.

Provided herein is a kit comprising:

(a) an electronic cigarette for generating an inhalable aerosol comprising
  i. a device body comprising a cartridge receptacle;
  ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point;
    iii. a heater;
    iv. a battery; and
    v. a mouthpiece; and
(b) instructions for using the electronic cigarette to generate an inhalable aerosol.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are used, and the accompanying drawings of which.

DETAILED DESCRIPTION OF THE INVENTION

Figure 1:
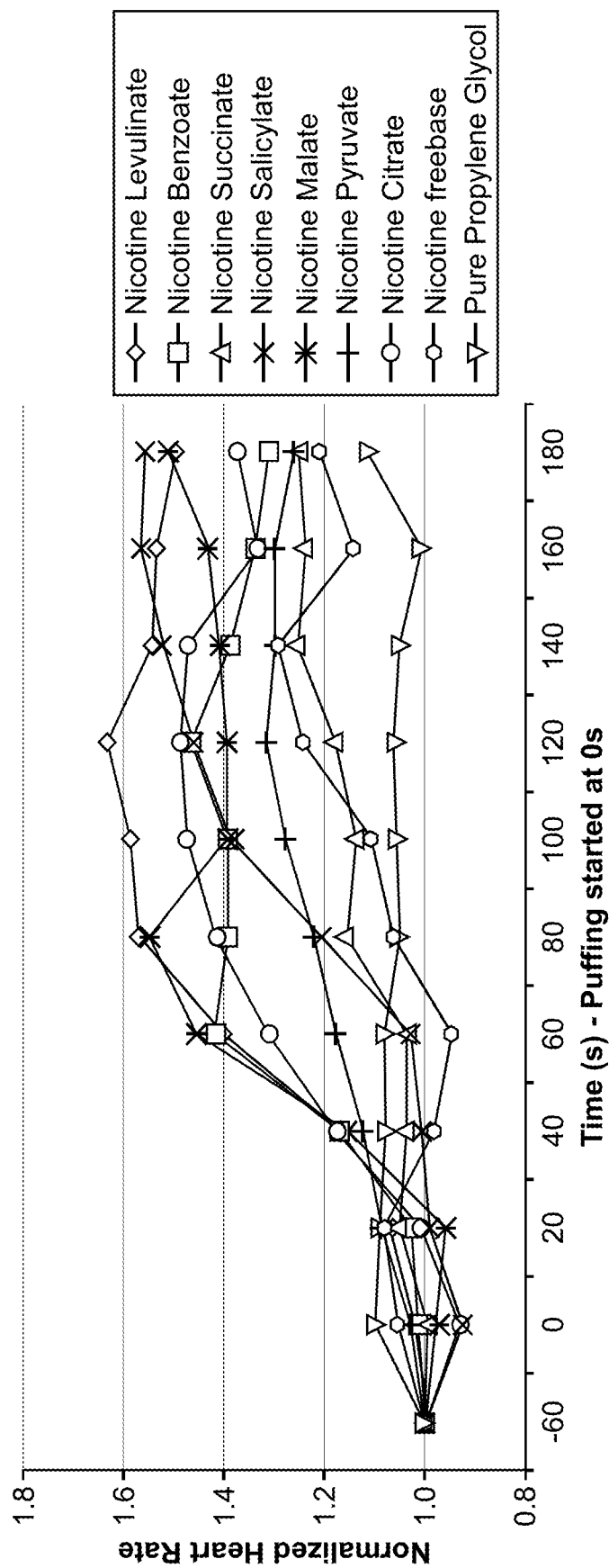
FIG. 1 illustrates results of heart rate data measured for six minutes from start of puffing. Y-axis is heart rate (bpm) and X-axis represent duration of the test (−60 to 180 seconds)

Nicotine is a chemical stimulant and increases heart rate and blood pressure when provided to an individual or animal. Nicotine transfer to an individual is associated with a feeling of physical and/or emotional satisfaction. Conflicting reports have been published regarding the transfer efficiency of free base nicotine in comparison to mono- or di-protonated nicotine salts. Studies on the transfer efficiency of free base nicotine and nicotine salts are complex and have yielded unpredictable results. Further, such transfer efficiency studies have been performed under extremely high temperature conditions, comparable to smoking; therefore, they offer scant guidance on the transfer efficiency of free base nicotine and nicotine salts under low-temperature vaporization conditions. Some reports have posited that nicotine free base should give rise to a greater satisfaction in a user than any corresponding nicotine salt.

It has been unexpectedly discovered herein that certain nicotine salt formulations provide satisfaction in an individual superior to that of free base nicotine, and more comparable to the satisfaction in an individual smoking a traditional cigarette. The satisfaction effect is consistent with an efficient transfer of nicotine to the lungs of an individual and a rapid rise of nicotine absorption in the plasma as shown, for non-limiting example, in Example 8, at least. It has also been unexpectedly discovered herein that certain nicotine salt formulations provide greater satisfaction than other nicotine salt formulations, and such effect has been shown in blood plasma levels of example nicotine salt formulations herein, for non-limiting example, in Example 8, at least. These results show a difference in rate of nicotine uptake in the blood that is higher for some nicotine salt formulations aerosolized by an electronic cigarette than for other nicotine salt formulations, and likewise higher than nicotine freebase formulations, while the peak concentration of the nicotine in the blood and total amount of nicotine delivered appears comparable to a traditional cigarette, and do not appear to vary significantly between the various nicotine formulations. Therefore, described herein are nicotine salt formulations for use in an electronic cigarette, or the like, that provide a general satisfaction effect consistent with an efficient transfer of nicotine to the lungs of an individual and a rapid rise of nicotine absorption in the plasma. Provided herein, therefore, are devices, formulation of nicotine salts, systems, cartomizers, kits and methods that are used to inhale an aerosol generated from a nicotine salt liquid formulation through the mouth or nose as described herein or as would be obvious to one of skill in the art upon reading the disclosure herein.

Consistent with these satisfaction effects, it has unexpectedly been found herein that there is a difference between the $C_{max}$ (maximum concentration) and $T_{max}$ (time at which the maximum concentration is measured) when measuring blood plasma nicotine levels of freebase nicotine formulations inhaled using a low temperature vaporization device, i.e. electronic cigarette, as compared to the $C_{max}$ and $T_{max}$ (similarly measuring blood plasma nicotine levels) of a traditional cigarette. Also consistent with these satisfaction effects, it has unexpectedly been found herein that there is a difference between the $C_{max}$ (maximum concentration) and $T_{max}$ (time at which the maximum concentration is measured) when measuring blood plasma nicotine levels of freebase nicotine formulations inhaled using a low temperature vaporization device, i.e. electronic cigarette, as compared to the $C_{max}$ and $T_{max}$ (similarly measuring blood plasma nicotine levels) of nicotine salt formulations inhaled using a low temperature vaporization device, i.e. electronic cigarette. Additionally, it has unexpectedly been found that there is a difference between the rate of nicotine uptake in the plasma of users inhaling freebase nicotine formulations using a low temperature vaporization device, i.e. electronic cigarette, as compared to the rate of nicotine uptake in the plasma of users inhaling smoke of a traditional cigarette. Furthermore, it has unexpectedly been found that there is a difference between the rate of nicotine uptake in the plasma of users inhaling freebase nicotine formulations using a low temperature vaporization device, i.e. electronic cigarette, as compared to the rate of nicotine uptake in the plasma of users inhaling nicotine salt formulations using a low temperature vaporization device, i.e. electronic cigarette.

Thus, looking at freebase nicotine as a source of nicotine in compositions used in e-cigarettes, freebase nicotine compositions' delivery of nicotine to blood when inhaled using is not necessarily comparable in blood plasma levels ($C_{max}$ and $T_{max}$) to a traditional cigarette's nicotine delivery to blood when inhaled. Freebase nicotine compositions' delivery of nicotine to blood when inhaled using is not necessarily comparable in blood plasma levels ($C_{max}$ and $T_{max}$) to nicotine salt formulations' nicotine delivery to blood when inhaled. Freebase nicotine compositions' delivery of nicotine to blood when inhaled using is not necessarily comparable in blood plasma levels when measuring the rate of nicotine uptake in the blood within the first 0-5 minutes to a traditional cigarette's nicotine delivery to blood when inhaled. Freebase nicotine compositions' delivery of nicotine to blood when inhaled using necessarily is not comparable in blood plasma levels when measuring the rate of nicotine uptake in the blood within the first 0-5 minutes to nicotine salt formulations' nicotine delivery to blood when inhaled.

Also consistent with these satisfaction effects, it has unexpectedly been found herein that while there appears to be comparable $C_{max}$ and $T_{max}$ values (measuring blood plasma nicotine levels) of nicotine salt formulations inhaled using a low temperature vaporization device, i.e. electronic cigarette, as compared to the $C_{max}$ and $T_{max}$ (similarly measuring blood plasma nicotine levels) of a traditional cigarette, there is a demonstrable difference between the rate of nicotine uptake in the plasma of users inhaling certain nicotine salt formulations using a low temperature vaporization device, i.e. electronic cigarette, as compared to the rate of nicotine uptake in the plasma of users inhaling other nicotine salt formulations using a low temperature vaporization device, i.e. electronic cigarette. It is also unexpected that while the $C_{max}$ and $T_{max}$ values are comparable to those of a traditional cigarette, (or are approaching that of a traditional cigarette), the rate of nicotine uptake in the plasma of blood of users is higher in certain nicotine salt formulations than that of the traditional cigarette. The nicotine salt formulations which demonstrate the quickest rate of nicotine uptake in the plasma were more preferred in satisfaction evaluations, and were rated more equivalent to cigarette satisfaction than the nicotine salt formulations showing the slowest rates of rise of nicotine in the subjects' blood plasma. In addition, doubling the concentration of the nicotine salt in the formulation may not necessarily impact the rate of absorption of nicotine in the blood (see, for non-limiting example Example 8, nicotine benzoate tested in 4% and 2% concentrations).

Thus, looking at nicotine salt formulations used in e-cigarettes, nicotine salt formulations delivered using an e-cigarette appear comparable in $C_{max}$ and $T_{max}$ values (measuring blood plasma nicotine levels), however, not all nicotine salts perform similarly to each other or to a traditional cigarette with respect to the rate of nicotine uptake in the blood at early time periods (0-1.5 minutes). These results are unexpected. Nicotine salt formulations made using acids having a Vapor Pressure between 20-300 mmHg @ 200° C., or Vapor Pressure >20 mmHg @ 200° C., or a Vapor Pressure from 20 to 300 mmHg @ 200° C., or a Vapor Pressure from 20 to 200 mmHg @ 200° C., a Vapor Pressure between 20 and 300 mmHg @ 200° C. appear to have a higher rate of nicotine uptake in the blood at early time periods (0-1.5 minutes, 0-3 minutes, 0-2 minutes, 0-4 minutes for non-limiting example) than other nicotine salt formulations, however, they also provide satisfaction comparable to a traditional cigarette or closer to a traditional cigarette (as compared to other nicotine salt formulations or as compared to nicotine freebase formulations). For non-limiting example, acids that meet one or more criteria of the prior sentence include salicylic acid, sorbic acid, benzoic acid, lauric acid, and levulinic acid. Nicotine salt formulations made using acids that have a difference between boiling point and melting point of at least 50° C., and a boiling point greater than 160° C., and a melting point less than 160° C. appear to have a higher rate of nicotine uptake in the blood at early time periods (0-1.5 minutes, 0-3 minutes, 0-2 minutes, 0-4 minutes for non-limiting example) than other nicotine salt formulations, however, they also provide satisfaction comparable to a traditional cigarette or closer to a traditional cigarette (as compared to other nicotine salt formulations or as compared to nicotine freebase formulations). For non-limiting example, acids that meet the criteria of the prior sentence include salicylic acid, sorbic acid, benzoic acid, pyruvic acid, lauric acid, and levulinic acid. Nicotine salt formulations made using acids that have a difference between boiling point and melting point of at least 50° C., and a boiling point at most 40° C. less than operating temperature, and a melting point at least 40° C. lower than operating temperature appear to have a higher rate of nicotine uptake in the blood at early time periods (0-1.5 minutes, 0-3 minutes, 0-2 minutes, 0-4 minutes for non-limiting example) than other nicotine salt formulations, however, they also provide satisfaction comparable to a traditional cigarette or closer to a traditional cigarette (as compared to other nicotine salt formulations or as compared to nicotine freebase formulations). Operating temperature can be 100° C. to 300° C., or about 200° C., about 150° C. to about 250° C., 180 C to 220° C., about 180° C. to about 220° C., 185° C. to 215° C., about 185° C. to about 215° C., about 190° C. to about 210° C., 190° C. to 210° C., 195° C. to 205° C., or about 195° C. to about 205° C. For non-limiting example, acids that meet the criteria of the prior sentence include salicylic acid, sorbic acid, benzoic acid, pyruvic acid, lauric acid, and levulinic acid. Combinations of these criteria for preference of certain nicotine salt formulations are contemplated herein.

Other reasons for excluding certain acids from formulations may be unrelated to the rate of nicotine uptake, however. For example, an acid may be inappropriate for use with the device materials (corrosive or otherwise incompatible). Sulfuric acid is an example of this, which may be inappropriate for the e-cigarette device. An acid may be inappropriate for use in inhalation or for toxicity reasons—thus not be compatible for human consumption, ingestion, or inhalation. Sulfuric acid again is an example of this, which may be inappropriate for a user of an e-cigarette device, depending on the embodiment of the composition. An acid that is bitter or otherwise bad-tasting may also provide a reason for exclusion, such as acetic acid in some embodiments. Acids that oxidize at room temperature or at operating temperature may be inappropriate for certain embodiments, for example, sorbic acid, as this indicates a decomposition or reaction or instability that may be undesirable in the formulation. Decomposition of acids at room or operating temperatures may also indicate that the acid is inappropriate for use in the embodiment formulations. For example, citric acid decomposes at 175° C., and malic acid decomposes at 140° C., thus for a device operating at 200° C., these acids may not be appropriate. Acids that have poor solubility in the composition constituents may be inappropriate for use in certain embodiments of the compositions herein. For example, nicotine bitartrate with a composition of nicotine and tartaric acid as 1:2 molar ratio will not produce a solution at a concentration of 0.5% (w/w) nicotine or higher and 0.9% (w/w) tartaric acid or higher in propylene glycol (PG) or vegetable glycerin (VG) or any mixture of PG and VG at ambient conditions. As used herein, weight percentage (w/w) refers to the weight of the individual component over the weight of the total formulation.

As used in this specification and the claims, the singular forms "a," "an," and "the" include plural referents unless the context clearly dictates otherwise.

The term "organic acid" as used herein, refers to an organic compound with acidic properties (e.g., by Brønsted-Lowry definition, or Lewis definition). A common organic acid is the carboxylic acids, whose acidity is associated with their carboxyl group —COOH. A dicarboxylic acid possesses two carboxylic acid groups. The relative acidity of an organic is measured by its $pK_a$ value and one of skill in the art knows how to determine the acidity of an organic acid based on its given pKa value. The term "keto acid" as used herein, refers to organic compounds that contain a carboxylic acid group and a ketone group. Common types of keto acids include alpha-keto acids, or 2-oxoacids, such as pyruvic acid or oxaloacetic acid, having the keto group adjacent to the carboxylic acid; beta-keto acids, or 3-oxoacids, such as acetoacetic acid, having the ketone group at the second carbon from the carboxylic acid; gamma-keto acids, or 4-oxoacids, such as levulinic acid, having the ketone group at the third carbon from the carboxylic acid.

The term "electronic cigarette" or "e-cigarette" or "low temperature vaporization device" as used herein, refers to an electronic inhaler that vaporizes a liquid solution into an aerosol mist, simulating the act of tobacco smoking. The liquid solution comprises a formulation comprising nicotine. There are many electronic cigarettes which do not resemble conventional cigarettes at all. The amount of nicotine contained can be chosen by the user via the inhalation. In general, an electronic cigarette contains three essential components: a plastic cartridge that serves as a mouthpiece and a reservoir for liquid, an "atomizer" that vaporizes the liquid, and a battery. Other embodiment electronic cigarettes include a combined atomizer and reservoir, called a "cartomizer" that may or may not be disposable, a mouthpiece that may be integrated with the cartomizer or not, and a battery.

As used in this specification and the claims, unless otherwise stated, the term "about" refers to variations of 1%, 2%, 3%, 4%, 5%, 10%, 15%, or 25%, depending on the embodiment.

Suitable carriers (e.g., a liquid solvent) for the nicotine salts described herein include a medium in which a nicotine salt is soluble at ambient conditions, such that the nicotine salt does not form a solid precipitate. Examples include, but are not limited to, glycerol, propylene glycol, trimethylene glycol, water, ethanol and the like, as well as combinations thereof. In some embodiments, the liquid carrier comprises 0% to 100% of propylene glycol and 100% to 0% of vegetable glycerin. In some embodiments, the liquid carrier comprises 10% to 70% of propylene glycol and 90% to 30% of vegetable glycerin. In some embodiments, the liquid carrier comprises 20% to 50% of propylene glycol and 80% to 50% of vegetable glycerin. In some embodiments, the liquid carrier comprises 30% propylene glycol and 70% vegetable glycerin.

The formulations described herein vary in concentration. In some formulations, a dilute concentration of the nicotine salt in the carrier is utilized. In some formulations, a less dilute concentration of the nicotine salt in the carrier is utilized. In some formulations the concentration of nicotine in the nicotine salt formulation is about 1% (w/w) to about 25% (w/w). In some formulations the concentration of nicotine in the nicotine salt formulation is about 1% (w/w) to about 20% (w/w). In some formulations the concentration of nicotine in the nicotine salt formulation is about 1% (w/w) to about 18% (w/w). In some embodiments the concentration of nicotine in the nicotine salt formulation is about 1% (w/w) to about 15% (w/w). In some formulations the concentration of nicotine in the nicotine salt formulation is about 4% (w/w) to about 12% (w/w). In some formulations the concentration of nicotine in the nicotine salt formulation is about 4% (w/w). In some embodiments the concentration of nicotine in the nicotine salt formulation is about 2% (w/w). In some formulations the concentration of nicotine in the nicotine salt formulation is 1% (w/w) to 25% (w/w). In some formulations the concentration of nicotine in the nicotine salt formulation is 1% (w/w) to 20% (w/w). In some formulations the concentration of nicotine in the nicotine salt formulation is 1% (w/w) to 18% (w/w). In some formulations the concentration of nicotine in the nicotine salt formulation is 1% (w/w) to 15% (w/w). In some formulations the concentration of nicotine in the nicotine salt formulation is 4% (w/w) to 12% (w/w). In some formulations the concentration of nicotine in the nicotine salt formulation is 4% (w/w). In some formulations the concentration of nicotine in the nicotine salt formulation is 2% (w/w). In some formulations, a less dilute concentration of one nicotine salt is used in conjunction with a more dilute concentration of a second nicotine salt. In some formulations, the concentration of nicotine in the first nicotine salt formulation is about 1% to about 20%, and is combined with a second nicotine salt formulation having a concentration of nicotine therein from about 1% to about 20% or any range or concentration therein. In some formulations, the concentration of nicotine in the first nicotine salt formulation is 1% to 20%, and is combined with a second nicotine salt formulation having a concentration of nicotine therein from 1% to 20% or any range or concentration therein. As used with respect to concentrations of nicotine in the nicotine salt formulations, the term "about" refers to ranges of 0.05% (i.e. if the concentration is about 2%, the range is 1.95%-2.05%), 0.1 (i.e. if the concentration is about 2%, the range is 1.9%-2.1%), 0.25 (i.e. if the concentration is about 2%, the range is 1.75%-2.25%), 0.5 (i.e. if the concentration is about 2%, the range is 1.5%-2.5%), or 1 (i.e. if the concentration is about 4%, the range is 3%-5%), depending on the embodiment.

Nicotine salts are formed by the addition of a suitable acid, including organic or inorganic acids. In some formulations provided herein, suitable organic acids are carboxylic acids. Examples of organic carboxylic acids disclosed herein are monocarboxylic acids, dicarboxylic acids (organic acid containing two carboxylic acid groups), carboxylic acids containing an aromatic group such as benzoic acids, hydroxycarboxylic acids, heterocyclic carboxylic acids, terpenoid acids, sugar acids; such as the pectic acids, amino acids, cycloaliphatic acids, aliphatic carboxylic acids, keto carboxylic acids, and the like. In some formulations provided herein, the organic acids used herein are monocarboxylic acids. Nicotine salts are formed from the addition of a suitable acid to nicotine. In some formulations provided herein, the stoichiometric ratios of the nicotine to acid (nicotine:acid) are 1:1, 1:2, 1:3, 1:4, 2:3, 2:5, 2:7, 3:4, 3:5, 3:7, 3:8, 3:10, 3:11, 4:5, 4:7, 4:9, 4:10, 4:11, 4:13, 4:14, 4:15, 5:6, 5:7, 5:8, 5:9, 5:11, 5:12, 5:13, 5:14, 5:16, 5:17, 5:18, or 5:19. In some formulations provided herein, the stoichiometric ratios of the nicotine to acid are 1:1, 1:2, 1:3, or 1:4 (nicotine:acid).

Nicotine is an alkaloid molecule that comprises two basic nitrogens. It may occur in different states of protonation. For example, if no protonation exists, nicotine is referred to as the "free base." If one nitrogen is protonated, then the nicotine would be "mono-protonated."

Nicotine salt formulations may be formed by adding a suitable acid to nicotine, stirring the neat mixture at ambient temperature or at elevated temperature, and then diluting the neat mixture with a carrier mixture, such as a mixture of propylene glycol and glycerin. In some embodiments, the suitable acid is completely dissolved by the nicotine prior to dilution. The suitable acid may not completely dissolved by the nicotine prior to dilution. The addition of the suitable acid to the nicotine to form a neat mixture may cause an exothermic reaction. The addition of the suitable acid to the nicotine to form a neat mixture may be conducted at 55° C. The addition of the suitable acid to the nicotine to form a neat mixture may be conducted at 90° C. The neat mixture may be cooled to ambient temperature prior to dilution. The dilution may be carried out at elevated temperature.

Nicotine salt formulations may be prepared by combining nicotine and a suitable acid in a carrier mixture, such as a mixture of propylene glycol and glycerin. The mixture of nicotine and a first carrier mixture is combined with a mixture of a suitable acid in a second carrier mixture. In some embodiments, the first and second carrier mixtures are identical in composition. In some embodiments, the first and second carrier mixtures are not identical in composition. In some embodiments, heating of nicotine/acid/carrier mixture is required to facilitate complete dissolution.

In some embodiments, nicotine salt formulations may be prepared and added to a solution of 3:7 ratio by weight of propylene glycol (PG)/vegetable glycerin (VG), and mixed thoroughly. While described herein as producing 10 g of each of the formulations, all procedures noted infra are scalable. Other manners of formulation may also be employed form the formulations noted infra, without departing from the disclosure herein, and as would be known to one of skill in the art upon reading the disclosure herein.

Figure 3:
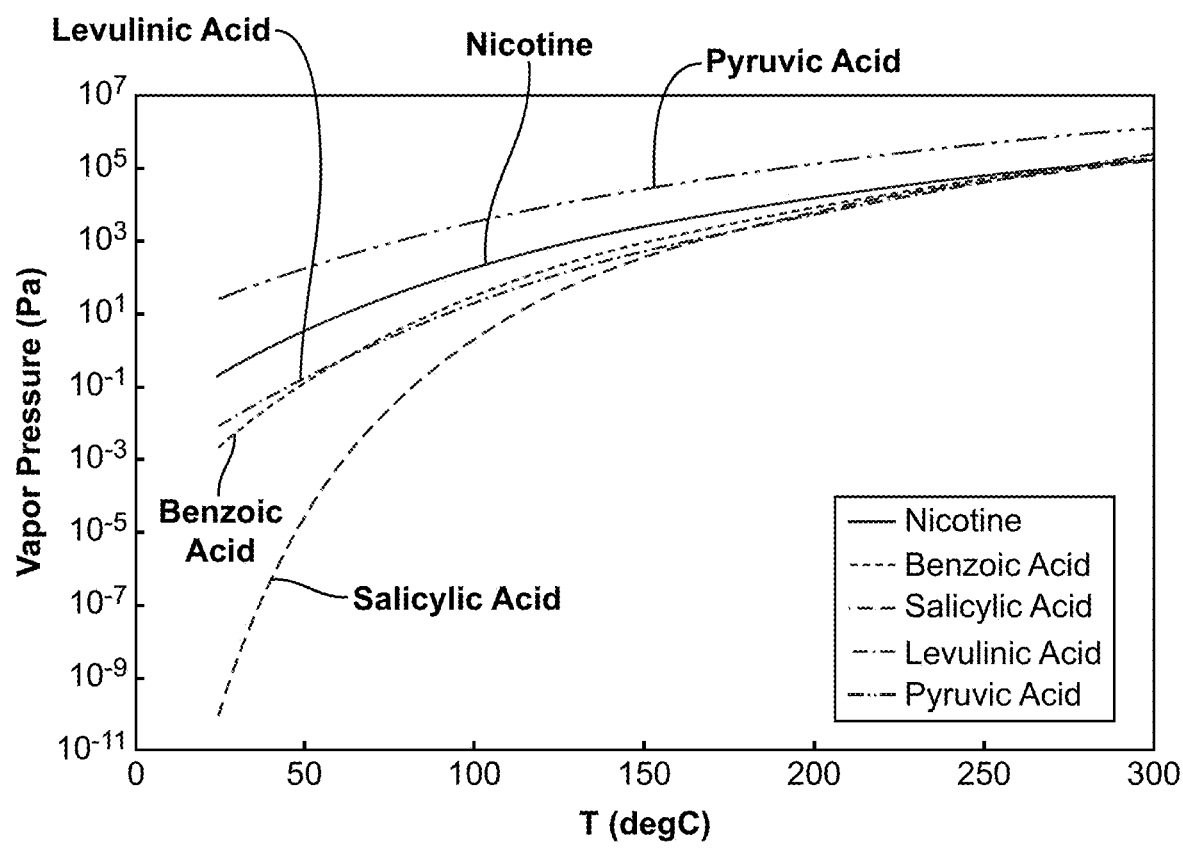
FIG. 3 illustrates the calculated vapor pressures of various acids relative to nicotine.

The optimal nicotine salt formulation may be determined by the vapor pressure of the constituent acid. In some embodiments, the nicotine salt formulations comprise an acid with a vapor pressure that is similar to the vapor pressure of free base nicotine. In some embodiments, the nicotine salt formulations are formed from an acid with a vapor pressure that is similar to the vapor pressure of free base nicotine at the heating temperature of the device. FIG. 3 illustrates this trend. Nicotine salts formed from nicotine and benzoic acid; nicotine and salicylic acid; or nicotine and levulinic acid are salts that produce a satisfaction in an individual user consistent with efficient transfer of nicotine and a rapid rise in nicotine plasma levels. This pattern may be due to the mechanism of action during heating of the nicotine salt formulation. The nicotine salt may disassociate at, or just below, the heating temperature of the device, resulting in a mixture of free base nicotine and the individual acid. At that point, if both the nicotine and acid have similar vapor pressures, they may aerosolize at the same time, giving rise to a transfer of both free base nicotine and the constituent acid to the user.

The nicotine salt liquid formulation for generating an inhalable aerosol upon heating in an electronic cigarette may comprise a nicotine salt in a biologically acceptable liquid carrier; wherein the acid used to form said nicotine salt is characterized by a vapor pressure between 20-4000 mmHg at 200° C. In some embodiments, the acid used to form the nicotine salt is characterized by vapor pressure between 20-2000 mmHg at 200° C. In some embodiments, the acid used to form the nicotine salt is characterized by vapor pressure between 100-300 mmHg at 200° C.

Unexpectedly, different nicotine salt formulations produced varying degrees of satisfaction in an individual. In some embodiments, the extent of protonation of the nicotine salt affected satisfaction, such that more protonation was less satisfying as compared to less protonation. The nicotine salt formed may be monoprotonated. The nicotine salt formed may be diprotonated. The nicotine salt may exist in more than one protonation state, e.g., an equilibrium of mono-protonated and di-protonated nicotine salts. The extent of protonation of the nicotine molecule may be dependent upon the stoichiometric ratio of nicotine:acid used in the salt formation reaction. The extent of protonation of the nicotine molecule may be dependent upon the solvent. The extent of protonation of the nicotine molecule may be unknown. In some embodiments, monoprotonated nicotine salts produced a high degree of satisfaction in the user. For example, nicotine benzoate and nicotine salicylate are mono-protonated nicotine salts and all produce a high degree of satisfaction in the user. The reason for this trend may be explained by a mechanism of action wherein the nicotine is first deprotonated prior to transfer to the vapor with the constituent acid and then retained and stabilized after re-protonated by the acid going down stream to the lungs of the user. It may be easier to remove one proton versus two protons, thus resulting in better transfer efficiency. In addition, the lack of satisfaction of free base nicotine indicates that a second factor may be important. A nicotine salt may be best performing when it is at its optimal extent of protonation, depending on the salt. For example, nicotine pyruvate is a nicotine salt with 1:2 nicotine:acid ratio. The formulation containing nicotine pyruvate (1:2) may deliver more satisfaction to the user than the one containing same amount of nicotine but only half amount of pyruvic acid, i.e. nicotine pyruvate (1:1). This may be explained as 1 mole of nicotine produces a salt with 2 moles of pyruvic acid. When there is not enough pyruvic acid to associate with all nicotine molecules, the free base nicotine left unprotonated in the formulation may reduce the satisfaction the formulation provides.

The flavor of the constituent acid used in the salt formation may be a consideration in choosing the acid. A suitable acid may have minimal or no toxicity to humans in the concentrations used. A suitable acid may be compatible with the electronic cigarette components it contacts or could contact at the concentrations used. That is, such acid does not degrade or otherwise react with the electronic cigarette components it contacts or could contact. The odor of the constituent acid used in the salt formation may be a consideration in choosing a suitable acid. The concentration of the nicotine salt in the carrier may affect the satisfaction in the individual user. In some embodiments, the flavor of the formulation is adjusted by changing the acid. In some embodiments, the flavor of the formulation is adjusted by adding exogenous flavorants. In some embodiments, an unpleasant tasting or smelling acid is used in minimal quantities to mitigate such characteristics. In some embodiments, exogenous pleasant smelling or tasting acid is added to the formulation. Examples of salts which can provide flavor and aroma to the mainstream aerosol at certain levels include nicotine acetate, nicotine oxalate, nicotine malate, nicotine isovalerate, nicotine lactate, nicotine citrate, nicotine phenylacetate and nicotine myristate.

Nicotine salt formulations may generate an inhalable aerosol upon heating in an electronic cigarette. The amount of nicotine or nicotine salt aerosol inhaled may be user-determined. The user may, for example, modify the amount of nicotine or nicotine salt inhaled by adjusting his inhalation strength.

Formulations are described herein comprising two or more nicotine salts. In some embodiments, wherein a formulation comprises two or more nicotine salts, each individual nicotine salt is formed as described herein.

Nicotine salt formulations, as used herein, refer to a single or mixture of nicotine salts with other suitable chemical components used for e-cigarette, such as carriers, stabilizers, diluents, dispersing agents, suspending agents, thickening agents, and/or excipients. In certain embodiments, the nicotine salt formulation is stirred at ambient conditions for 20 minutes. In certain embodiments, the nicotine salt formulation is heated and stirred at 55 C for 20 minutes. In certain embodiments, the nicotine salt formulation is heated and stirred at 90 C for 60 minutes. In certain embodiments, the formulation facilitates administration of nicotine to an organism (e.g., lung).

The nicotine of nicotine salt formulations provided herein is either naturally occurring nicotine (e.g., from extract of nicotineous species such as tobacco), or synthetic nicotine. In some embodiments, the nicotine is (−)-nicotine, (+)-nicotine, or a mixture thereof. In some embodiments, the nicotine is employed in relatively pure form (e.g., greater than about 80% pure, 85% pure, 90% pure, 95% pure, or 99% pure). In some embodiments, the nicotine for nicotine salt formulation provided herein is "water clear" in appearance in order to avoid or minimize the formation of tarry residues during the subsequent salt formation steps.

Nicotine salt formulations used for e-cigarettes described herein, in some embodiments, have a nicotine concentration of about 0.5% (w/w) to about 20% (w/w), wherein the concentration is of nicotine weight to total solution weight, i.e. (w/w). In certain embodiments, nicotine salt formulations provided herein have a nicotine concentration of about 1% (w/w) to about 20% (w/w). In certain embodiments, nicotine salt formulations provided herein have a nicotine concentration of about 1% (w/w) to about 18% (w/w). In certain embodiments, nicotine salt formulations provided herein have a nicotine concentration of about 1% (w/w) to about 15% (w/w). In certain embodiments, nicotine salt formulations provided herein have a nicotine concentration of about 4% (w/w) to about 12% (w/w). In certain embodiments, nicotine salt formulations provided herein have a nicotine concentration of about 1% (w/w) to about 18% (w/w), about 3% (w/w) to about 15% (w/w), or about 4% (w/w) to about 12% (w/w). In certain embodiments, nicotine salt formulations provided herein have a nicotine concentration of about 0.5% (w/w) to about 10% (w/w). In certain embodiments, nicotine salt formulations provided herein have a nicotine concentration of about 0.5% (w/w) to about 5% (w/w). In certain embodiments, nicotine salt formulations provided herein have a nicotine concentration of about 0.5% (w/w) to about 4% (w/w). In certain embodiments, nicotine salt formulations provided herein have a nicotine concentration of about 0.5% (w/w) to about 3% (w/w). In certain embodiments, nicotine salt formulations provided herein have a nicotine concentration of about 0.5% (w/w) to about 2% (w/w). In certain embodiments, nicotine salt formulations provided herein have a nicotine concentration of about 0.5% (w/w) to about 1% (w/w). In certain embodiments, nicotine salt formulations provided herein have a nicotine concentration of about 1% (w/w) to about 10% (w/w). In certain embodiments, nicotine salt formulations provided herein have a nicotine concentration of about 1% (w/w) to about 5% (w/w). In certain embodiments, nicotine salt formulations provided herein have a nicotine concentration of about 1% (w/w) to about 4% (w/w). In certain embodiments, nicotine salt formulations provided herein have a nicotine concentration of about 1% (w/w) to about 3% (w/w). In certain embodiments, nicotine salt formulations provided herein have a nicotine concentration of about 1% (w/w) to about 2% (w/w). In certain embodiments, nicotine salt formulations provided herein have a nicotine concentration of about 2% (w/w) to about 10% (w/w). In certain embodiments, nicotine salt formulations provided herein have a nicotine concentration of about 2% (w/w) to about 5% (w/w). In certain embodiments, nicotine salt formulations provided herein have a nicotine concentration of about 2% (w/w) to about 4% (w/w). Certain embodiments provide a nicotine salt formulation having a nicotine concentration of about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.5%, 5.0%, 5.5%, 6.0%, 6.5%, 7.0%, 7.5%, 8.0%, 8.5%, 9.0%, 9.5%, 10%, 11%, 12%, 13%, 14%, 15%, 16%, 17%, 18%, 19%, or 20% (w/w), or more, including any increments therein. Certain embodiments provide a nicotine salt formulation having a nicotine concentration of about 5% (w/w). Certain embodiments provide a nicotine salt formulation having a nicotine concentration of about 4% (w/w). Certain embodiments provide a nicotine salt formulation having a nicotine concentration of about 3% (w/w). Certain embodiments provide a nicotine salt formulation having a nicotine concentration of about 2% (w/w). Certain embodiments provide a nicotine salt formulation having a nicotine concentration of about 1% (w/w). Certain embodiments provide a nicotine salt formulation having a nicotine concentration of about 0.5% (w/w).

The formulation further may comprise one or more flavorants.

Thee suitable acid for the nicotine salt formulation may have a vapor pressure >20 mmHg at 200° C. and is non-corrosive to the electronic cigarette or is non-toxic to humans. In some embodiments, the suitable acid for nicotine salt formation is selected from the group consisting of salicylic acid, formic acid, sorbic acid, acetic acid, benzoic acid, pyruvic acid, lauric acid, and levulinic acid.

Thee suitable acid for the nicotine salt formulation may have a vapor pressure of about 20 to 200 mmHg at 200° C. and is non-corrosive to the electronic cigarette or is non-toxic to humans. In some embodiments, the suitable acid for nicotine salt formation is selected from the group consisting of salicylic acid, benzoic acid, lauric acid, and levulinic acid.

Thee suitable acid for the nicotine salt formulation may have a melting point <160° C., a boiling point >160° C., at least a 50-degree difference between the melting point and the boiling point, and is non-corrosive to the electronic cigarette or is non-toxic to humans. In some embodiments, the suitable acid for nicotine salt formation has a melting point at least 40 degrees lower than the operating temperature of the electronic cigarette, a boiling point no more than 40 degrees lower than the operating temperature of the electronic cigarette, at least a 50-degree difference between the melting point and the boiling point, and is non-corrosive to the electronic cigarette or is non-toxic to humans; wherein the operating temperature is 200° C. In some embodiments, the suitable acid for nicotine salt formation is selected from the group consisting of salicylic acid, sorbic acid, benzoic acid, pyruvic acid, lauric acid, and levulinic acid.

Thee suitable acid for the nicotine salt formulation does not decompose at the operating temperature of the electronic cigarette. In some embodiments, the suitable acid for nicotine salt formation does not oxidize at the operating temperature of the electronic cigarette. In some embodiments, the suitable acid for nicotine salt formation does not oxidize at room temperature. In some embodiments, the suitable acid for nicotine salt formation does not provide an unpleasant taste. In some embodiments, the suitable acid for nicotine salt formation has good solubility in a liquid formulation for use in an electronic cigarette.

Figure 7:
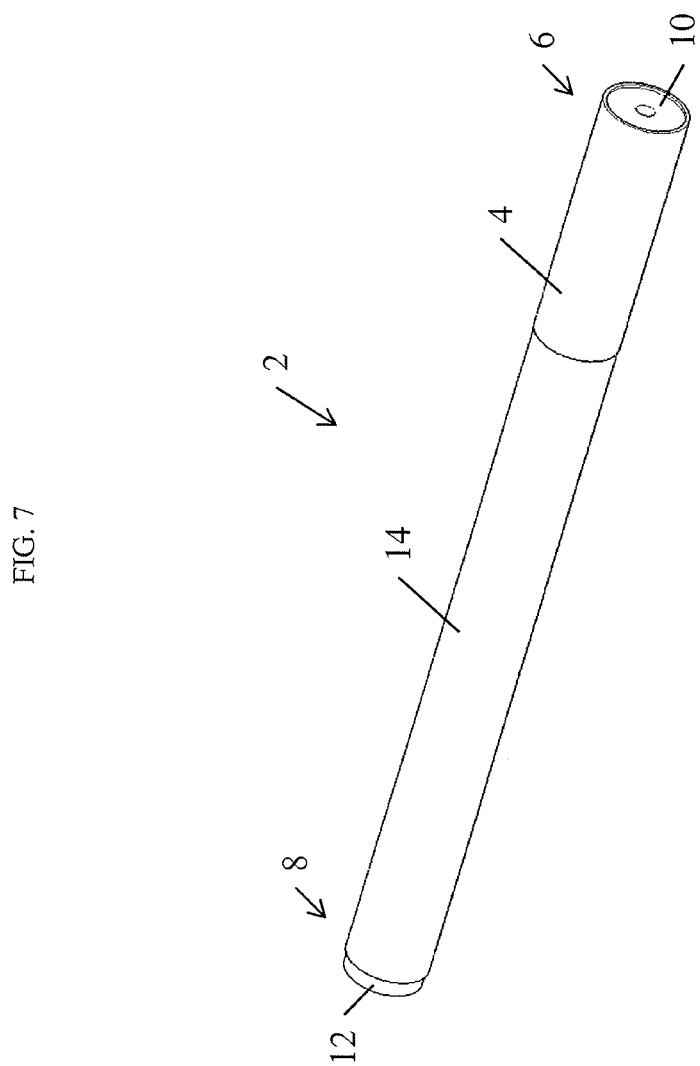
FIG. 7 depicts an example embodiment of an electronic cigarette having a fluid storage compartment comprising an embodiment nicotine salt formulation described herein.

Provided herein is an electronic cigarette 2 having a fluid storage compartment 4 comprising an embodiment nicotine salt formulation of any embodiment described herein within the fluid storage compartment described herein. An embodiment is shown in FIG. 7. The electronic cigarette 2 of FIG. 7 includes a mouth end 6, and a charging end 8. The mouth-end 6 includes a mouthpiece 10. The charging end 8 may connect to a battery or a charger or both, wherein the battery is within a body of the electronic cigarette, and the charger is separate from the battery and couples to the body or the battery to charge the battery. In some embodiments the electronic cigarette comprises a rechargeable battery within a body 14 of the electronic cigarette and the charge end 8 comprises a connection 12 for charging the rechargeable battery. In some embodiments, the electronic cigarette comprises a cartomizer that comprises the fluid storage compartment and an atomizer. In some embodiments, the atomizer comprises a heater. In some embodiments the fluid storage compartment 4 is separable from an atomizer. In some embodiments the fluid storage compartment 4 is replaceable as part of a replaceable cartridge. In some embodiments the fluid storage compartment 4 is refillable. In some embodiments, the mouthpiece 10 is replaceable.

Figure 8:
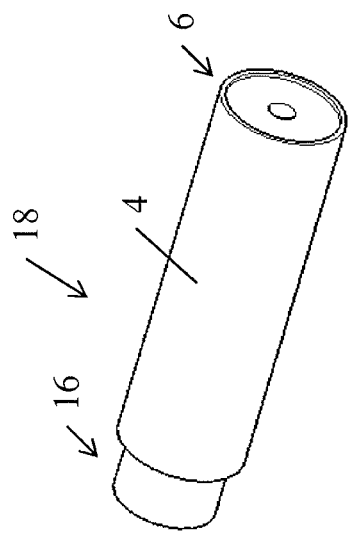
FIG. 8 depicts an example embodiment of an electronic cigarette cartomizer having a fluid storage compartment, a heater, and comprising an embodiment nicotine salt formulation described herein.

Provided herein is a cartomizer 18 for an electronic cigarette 2 having a fluid storage compartment 4 comprising an embodiment nicotine salt formulation of any embodiment described herein within the fluid storage compartment described herein. The cartomizer 18 embodiment of FIG. 8 includes a mouth end 6, and a connection end 16. The connection end 16 in the embodiment of FIG. 8 couples the cartomizer 14 to a body of an electronic cigarette, or to a battery of the electronic cigarette, or both. The mouth end 6 includes a mouthpiece 10. In some embodiments, the cartomizer does not include a mouthpiece, and in such embodiments, the cartomizer can be coupled to a mouthpiece of an electronic cigarette, or the cartomizer can be coupled to a battery or body of an electronic cigarette, while the mouthpiece is also coupled to the battery or the body of the electronic cigarette. In some embodiments, the mouthpiece is integral with the body of the electronic cigarette. In some embodiments, including the embodiment of FIG. 8, the cartomizer 18 comprises the fluid storage compartment 4 and an atomizer (not shown). In some embodiments, the atomizer comprises a heater (not shown)

EXAMPLES

Example 1: Preparation of Nicotine Salt Formulations

Various nicotine formulations were prepared and added to a solution of 3:7 ratio by weight of propylene glycol (PG)/vegetable glycerin (VG), and mixed thoroughly. The examples shown below were used to make 10 g of each of the formulations. All procedures are scalable.

For example, in order to make nicotine formulations with a final nicotine free base equivalent concentration of 2% (w/w), the following procedures were applied to each individual formulation.

Nicotine benzoate salt formulation: 0.15 g benzoic acid was added to a beaker followed by adding 0.2 g nicotine to the same beaker. The mixture was stirred at 55° C. for 20 minutes until benzoic acid was completely dissolved and an orange oily mixture was formed. The mixture was cooled down to ambient conditions. 9.65 g PG/VG (3:7) solution was added to the orange nicotine benzoate salt and the mixture was stirred until a visually homogenous formulation solution was achieved.

Nicotine benzoate salt formulation can also be made by adding 0.15 g benzoic acid to a beaker followed by adding 0.2 g nicotine and 9.65 g PG/VG (3:7) solution to the same beaker. The mixture was then stirred at 55° C. for 20 minutes until a visually homogenous formulation solution was achieved with no undissolved chemicals.

Nicotine citrate salt formulation was made by adding 0.47 g citric acid to a beaker followed by adding 0.2 g nicotine and 9.33 g PG/VG (3:7) solution to the same beaker. The mixture was then stirred at 90° C. for 60 minutes until a visually homogenous formulation solution was achieved with no undissolved chemicals.

Nicotine malate salt formulation was made by adding 0.33 g L-malic acid to a beaker followed by adding 0.2 g nicotine and 9.47 g PG/VG (3:7) solution to the same beaker. The mixture was then stirred at 90° C. for 60 minutes until a visually homogenous formulation solution was achieved with no undissolved chemicals.

Nicotine succinate salt formulation was made by adding 0.29 g succinic acid to a beaker followed by adding 0.2 g nicotine and 9.51 g PG/VG (3:7) solution to the same beaker. The mixture was then stirred at 90° C. for 60 minutes until a visually homogenous formulation solution was achieved with no undissolved chemicals.

Nicotine salicylate salt formulation was made by adding 0.17 g salicylic acid to a beaker followed by adding 0.2 g nicotine and 9.63 g PG/VG (3:7) solution to the same beaker. The mixture was then stirred at 90° C. for 60 minutes until a visually homogenous formulation solution was achieved with no undissolved chemicals.

Nicotine salicylate salt formulation can also be made by adding 0.17 g salicylic acid to a beaker followed by adding 0.2 g nicotine to the same beaker. The mixture was stirred at 90° C. for 60 minutes until salicylic acid was completely dissolved and an orange oily mixture was formed. The mixture was either cooled to ambient conditions or kept at 90° C. when 9.63 g PG/VG (3:7) solution was added. The mixture was then stirred at 90° C. until a visually homogenous formulation solution was achieved with no undissolved chemicals.

Nicotine free base formulation was made by adding 0.2 g nicotine to a beaker followed by adding 9.8 g PG/VG (3:7) solution to the same beaker. The mixture was then stirred at ambient conditions for 10 minutes until a visually homogenous formulation solution was achieved.

For example, in order to make nicotine salt formulations with a final nicotine free base equivalent concentration of 3% (w/w), the following procedures were applied to each individual formulation.

Nicotine benzoate salt formulation: 0.23 g benzoic acid was added to a beaker followed by adding 0.3 g nicotine to the same beaker. The mixture was stirred at 55° C. for 20 minutes until benzoic acid was completely dissolved and an orange oily mixture was formed. The mixture was cooled down to ambient conditions. 9.47 g PG/VG (3:7) solution was added to the orange nicotine benzoate salt and the blend was stirred until a visually homogenous formulation solution was achieved.

Nicotine benzoate salt formulation can also be made by adding 0.23 g benzoic acid to a beaker followed by adding 0.3 g nicotine and 9.47 g PG/VG (3:7) solution to the same beaker. The mixture was then stirred at 55° C. for 20 minutes until a visually homogenous formulation solution was achieved with no undissolved chemicals.

Nicotine citrate salt formulation was made by adding 0.71 g citric acid to a beaker followed by adding 0.3 g nicotine and 8.99 g PG/VG (3:7) solution to the same beaker. The mixture was then stirred at 90° C. for 60 minutes until a visually homogenous formulation solution was achieved with no undissolved chemicals.

Nicotine malate salt formulation was made by adding 0.5 g L-malic acid to a beaker followed by adding 0.3 g nicotine and 9.2 g PG/VG (3:7) solution to the same beaker. The mixture was then stirred at 90° C. for 60 minutes until a visually homogenous formulation solution was achieved with no undissolved chemicals.

Nicotine levulinate salt formulation was made by adding melted 0.64 g levulinic acid to a beaker followed by adding 0.3 g nicotine to the same beaker. The mixture was stirred at ambient conditions for 10 minutes. Exothermic reaction took place and oily product was produced. The mixture was allowed to cool down to ambient temperature and 9.06 g PG/VG (3:7) solution was added to the same beaker. The mixture was then stirred at ambient conditions for 20 minutes until a visually homogenous formulation solution was achieved.

Nicotine pyruvate salt formulation was made by adding 0.33 g pyruvic acid to a beaker followed by adding 0.3 g nicotine to the same beaker. The mixture was stirred at ambient conditions for 10 minutes. Exothermic reaction took place and oily product was produced. The mixture was allowed to cool down to ambient temperature and 9.37 g PG/VG (3:7) solution was added to the same beaker. The mixture was then stirred at ambient conditions for 20 minutes until a visually homogenous formulation solution was achieved.

Nicotine succinate salt formulation was made by adding 0.44 g succinic acid to a beaker followed by adding 0.3 g nicotine and 9.26 g PG/VG (3:7) solution to the same beaker. The mixture was then stirred at 90° C. for 60 minutes until a visually homogenous formulation solution was achieved with no undissolved chemicals.

Nicotine salicylate salt formulation was made by adding 0.26 g salicylic acid to a beaker followed by adding 0.3 g nicotine and 9.44 g PG/VG (3:7) solution to the same beaker. The mixture was then stirred at 90° C. for 60 minutes until a visually homogenous formulation solution was achieved with no undissolved chemicals.

Nicotine salicylate salt formulation can also be made by adding 0.26 g salicylic acid to a beaker followed by adding 0.3 g nicotine to the same beaker. The mixture was stirred at 90° C. for 60 minutes until salicylic acid was completely dissolved and an orange oily mixture was formed. The mixture was either cooled to ambient conditions or kept at 90° C. when 9.44 g PG/VG (3:7) solution was added. The blend was then stirred at 90 C until a visually homogenous formulation solution was achieved with no undissolved chemicals.

Nicotine free base formulation was made by adding 0.3 g nicotine to a beaker followed by adding 9.7 g PG/VG (3:7) solution to the same beaker. The mixture was then stirred at ambient conditions for 10 minutes until a visually homogenous formulation solution was achieved.

For example, in order to make nicotine salt formulations with a final nicotine free base equivalent concentration of 4% (w/w), the following procedures were applied to each individual formulation.

Nicotine benzoate salt formulation: 0.3 g benzoic acid was added to a beaker followed by adding 0.4 g nicotine to the same beaker. The mixture was stirred at 55° C. for 20 minutes until benzoic acid was completely dissolved and an orange oily mixture was formed. The mixture was cooled down to ambient conditions. 9.7 g PG/VG (3:7) solution was added to the orange nicotine benzoate salt and the blend was stirred until a visually homogenous formulation solution was achieved.

Nicotine benzoate salt formulation can also be made by adding 0.3 g benzoic acid to a beaker followed by adding 0.4 g nicotine and 9.7 g PG/VG (3:7) solution to the same beaker. The mixture was then stirred at 55° C. for 20 minutes until a visually homogenous formulation solution was achieved with no undissolved chemicals.

For example, in order to make nicotine salt formulations with a final nicotine free base equivalent concentration of 5% (w/w), the following procedures were applied to each individual formulation.

Nicotine benzoate salt formulation: 0.38 g benzoic acid was added to a beaker followed by adding 0.5 g nicotine to the same beaker. The mixture was stirred at 55° C. for 20 minutes until benzoic acid was completely dissolved and an orange oily mixture was formed. The mixture was cooled down to ambient conditions. 9.12 g PG/VG (3:7) solution was added to the orange nicotine benzoate salt and the blend was stirred until a visually homogenous formulation solution was achieved.

Nicotine benzoate salt formulation can also be made by adding 0.38 g benzoic acid to a beaker followed by adding 0.5 g nicotine and 9.12 g PG/VG (3:7) solution to the same beaker. The mixture was then stirred at 55° C. for 20 minutes until a visually homogenous formulation solution was achieved with no undissolved chemicals.

Nicotine malate salt formulation was made by adding 0.83 g L-malic acid to a beaker followed by adding 0.5 g nicotine and 8.67 g PG/VG (3:7) solution to the same beaker. The mixture was then stirred at 90° C. for 60 minutes until a visually homogenous formulation solution was achieved with no undissolved chemicals.

Nicotine levulinate salt formulation was made by adding melted 1.07 g levulinic acid to a beaker followed by adding 0.5 g nicotine to the same beaker. The mixture was stirred at ambient conditions for 10 minutes. Exothermic reaction took place and oily product was produced. The mixture was allowed to cool down to ambient temperature and 8.43 g PG/VG (3:7) solution was added to the same beaker. The mixture was then stirred at ambient conditions for 20 minutes until a visually homogenous formulation solution was achieved.

Nicotine pyruvate salt formulation was made by adding 0.54 g pyruvic acid to a beaker followed by adding 0.5 g nicotine to the same beaker. The mixture was stirred at ambient conditions for 10 minutes. Exothermic reaction took place and oily product was produced. The mixture was allowed to cool down to ambient temperature and 8.96 g PG/VG (3:7) solution was added to the same beaker. The mixture was then stirred at ambient conditions for 20 minutes until a visually homogenous formulation solution was achieved.

Nicotine succinate salt formulation was made by adding 0.73 g succinic acid to a beaker followed by adding 0.5 g nicotine and 8.77 g PG/VG (3:7) solution to the same beaker. The mixture was then stirred at 90° C. for 60 minutes until a visually homogenous formulation solution was achieved with no undissolved chemicals.

Nicotine salicylate salt formulation was made by adding 0.43 g salicylic acid to a beaker followed by adding 0.5 g nicotine and 9.07 g PG/VG (3:7) solution to the same beaker. The mixture was then stirred at 90° C. for 60 minutes until a visually homogenous formulation solution was achieved with no undissolved chemicals.

Nicotine salicylate salt formulation can also be made by adding 0.43 g salicylic acid to a beaker followed by adding 0.5 g nicotine to the same beaker. The mixture was stirred at 90° C. for 60 minutes until salicylic acid was completely dissolved and an orange oily mixture was formed. The mixture was either cooled to ambient conditions or kept at 90 C when 9.07 g PG/VG (3:7) solution was added. The blend was then stirred at 90° C. until a visually homogenous formulation solution was achieved with no undissolved chemicals.

Nicotine free base formulation was made by adding 0.5 g nicotine to a beaker followed by adding 9.5 g PG/VG (3:7) solution to the same beaker. The mixture was then stirred at ambient conditions for 10 minutes until a visually homogenous formulation solution was achieved.

Various formulations comprising different nicotine salts can be prepared similarly, or different concentrations of the above-noted nicotine formulations or other nicotine salt formulations can be prepared as one of skill in the art would know to do upon reading the disclosure herein.

Various formulations comprising two or more nicotine salts can be prepared similarly in a solution of 3:7 ratio of propylene glycol (PG)/vegetable glycerin (VG). For example, 0.43 g (2.5% w/w nicotine) of nicotine levulinate salt and 0.34 g (2.5% w/w nicotine) of nicotine acetate salt are added to 9.23 g of PG/VG solution, to achieve a 5% w/w nicotine formulation.

Also provided is another exemplary formulation. For example, 0.23 g (1.33% w/w nicotine) of nicotine benzoate salt (molar ratio 1:1 nicotine/benzoic acid), 0.25 g (1.33% w/w nicotine) of nicotine salicylate salt (molar ratio 1:1 nicotine/salicylic acid) and 0.28 g (1.34% w/w nicotine) of nicotine pyruvate salt (molar ratio 1:2 nicotine/pyruvic acid) are added to 9.25 g of PG/VG solution, to achieve a 5% w/w nicotine formulation.

Example 2: Heart Rate Study of Nicotine Solutions Via e-Cigarette

Exemplary formulations of nicotine levulinate, nicotine benzoate, nicotine succinate, nicotine salicylate, nicotine malate, nicotine pyruvate, nicotine citrate, nicotine freebase, and a control of propylene glycol were prepared as noted in Example 1 in 3% w/w solutions and were administered in the same fashion by an electronic cigarette to the same human subject. About 0.5 mL of each solution was loaded into an "eRoll" cartridge atomizer (joyetech.com) to be used in the study. The atomizer was then attached to an "eRoll" e-cigarette (same manufacturer). The operating temperature was from about 150° C. to about 250° C., or from about 180° C. to about 220° C.

Heart rate measurements were taken for 6 minutes; from 1 minute before start of puffing, for 3 minutes during puffing, and continuing until 2 minutes after end of puffing. The test participant took 10 puffs over 3 minutes in each case. The base heart rate was the average heart rate over the first 1 minute before start of puffing. Heart rate after puffing started was averaged over 20-second intervals. Puffing (inhalation) occurred every 20 seconds for a total of 3 minutes. Normalized heart rate was defined as the ratio between individual heart rate data point and the base heart rate. Final results were presented as normalized heart rate, shown for the first 4 minutes in FIG. 1.

FIG. 1 summarizes results from heart rate measurements taken for a variety of nicotine salt formulations. For ease of reference in reviewing FIG. 1, at the 180-second timepoint, from top to bottom (highest normalized heart rate to lowest normalized heart rate), the nicotine formulations are as follows: nicotine salicylate formulation, nicotine malate formulation, nicotine levulinate formulation (nearly identical to nicotine malate formulation at 180 seconds, thus, as a second reference point: the nicotine malate formulation curve is lower than the nicotine levulinate formulation curve at the 160-second time point), nicotine pyruvate formulation, nicotine benzoate formulation, nicotine citrate formulation, nicotine succinate formulation, and nicotine free base formulation. The bottom curve (lowest normalized heart rate) at the 180-second timepoint is associated with the placebo (100% propylene glycol). The test formulations comprising a nicotine salt cause a faster and more significant rise in heart rate than the placebo. The test formulations comprising a nicotine salt also cause faster and more significant rise when compared with a nicotine freebase formulation with the same amount of nicotine by weight. In addition, the nicotine salts (e.g., nicotine benzoate and nicotine pyruvate) prepared from the acids having calculated vapor pressures between 20-200 mmHg at 200° C. (benzoic acid (171.66 mmHg), with the exception of pyruvic acid (having a boiling point of 165 C), respectively) cause a faster rise in heart rate than the rest. The nicotine salts (e.g., nicotine levulinate, nicotine benzoate, and nicotine salicylate) prepared from the acids (benzoic acid, levulinic acid and salicylic acid, respectively) also cause a more significant heart rate increase. Thus, other suitable nicotine salts formed by the acids with the similar vapor pressure and/or similar boiling point may be used in accordance with the practice of the present invention. This experience of increased heart rate theoretically approaching or theoretically comparable to that of a traditional burned cigarette has not been demonstrated or identified in other electronic cigarette devices. Nor has it been demonstrated or identified in low temperature tobacco vaporization devices (electronic cigarettes) that do not burn the tobacco, even when a nicotine salt was used (a solution of 20% (w/w) or more of nicotine salt) as an additive to the tobacco. Thus the results from this experiment are surprising and unexpected.

Example 3: Satisfaction Study of Nicotine Salt Solution Via e-Cigarette

In addition to the heart rate study shown in Example 2, nicotine formulations (using 3% w/w nicotine formulations as described in Example 1) were used to conduct a satisfaction study in a single test participant. The test participant, an e-cigarette and/or traditional cigarette user, was required to have no nicotine intake for at least 12 hours before the test. The participant took 10 puffs using an e-cigarette (same as used in Example 2) over 3 minutes in each case, and then was asked to rate the level of physical and emotional satisfaction he or she felt on a scale of 0-10, with 0 being no physical or emotional satisfaction. The results indicated that the least satisfying compound was the nicotine free base. Nicotine benzoate, nicotine salicylate, and nicotine succinate all performed well, followed by nicotine pyruvate, nicotine citrate, and nicotine pyruvate.

Based on the Satisfaction Study, the nicotine salts formulations with acids having vapor pressure ranges between >20 mmHg @ 200° C., or 20-200 mmHg @ 200° C., or 100-300 mmHg @ 200° C. provide more satisfaction than the rest (except the pyruvic acid which has boiling point of 165° C.). For reference, it has been determined that salicylic acid has a vapor pressure of about 135.7 mmHg @ 200° C., benzoic acid has a vapor pressure of about 171.7 mmHg @ 200° C., lauric acid has a vapor pressure of about 38 mmHg @ 200° C., and levulinic acid has a vapor pressure of about 149 mmHg @ 200° C.

Example 4: Test Formulation 1 (TF1)

A solution of nicotine levulinate in glycerol comprising nicotine salt used: 1.26 g (12.6% w/w) of 1:3 nicotine levulinate 8.74 g (87.4% w/w) of glycerol—Total weight 10.0 g.

Neat nicotine levulinate was added to the glycerol, and mixed thoroughly. L-Nicotine has a molar mass of 162.2 g, and levulinic acid molar mass is 116.1 g. In a 1:3 molar ratio, the percentage of nicotine in nicotine levulinate by weight is given by: 162.2 g/(162.2 g+(3×116.1 g))=31.8% (w/w).

Example 5: Test Formulation 2 (TF2)

A solution of free base nicotine in glycerol comprising 0.40 g (4.00% w/w) of L-nicotine was dissolved in 9.60 g (96.0% w/w) of glycerol and mixed thoroughly.

Example 6: Heart Rate Study of Nicotine Solutions Via e-Cigarette

Both formulations (TF1 and TF2) were administered in the same fashion by an electronic cigarette to the same human subject: about 0.6 mL of each solution was loaded into "eGo-C" cartridge atomizer (joyetech.com). The atomizer was then attached to an "eVic" e-cigarette (same manufacturer). This model of e-cigarette allows for adjustable voltage, and therefore wattage, through the atomizer. The operating temperature of the e-cigarette is from about 150° C. to about 250° C., or from about 180° C. to about 220° C. The atomizer in both cases has resistance 2.4 ohms, and the e-cigarette was set to 4.24V, resulting in 7.49 W of power. ($P=V^2/R$)

Heart rate was measured in a 30-second interval for ten minutes from start of puffing. Test participants took 10 puffs over 3 minutes in each case (solid line ($2^{nd}$ highest peak): cigarette, dark dotted line (highest peak): test formulation 1 (TF1-nicotine salt formulation), light dotted line: test formulation 2 (TF2—nicotine formulation). Comparison between cigarette, TF1, and TF2 is shown in FIG. 2.

Figure 2:
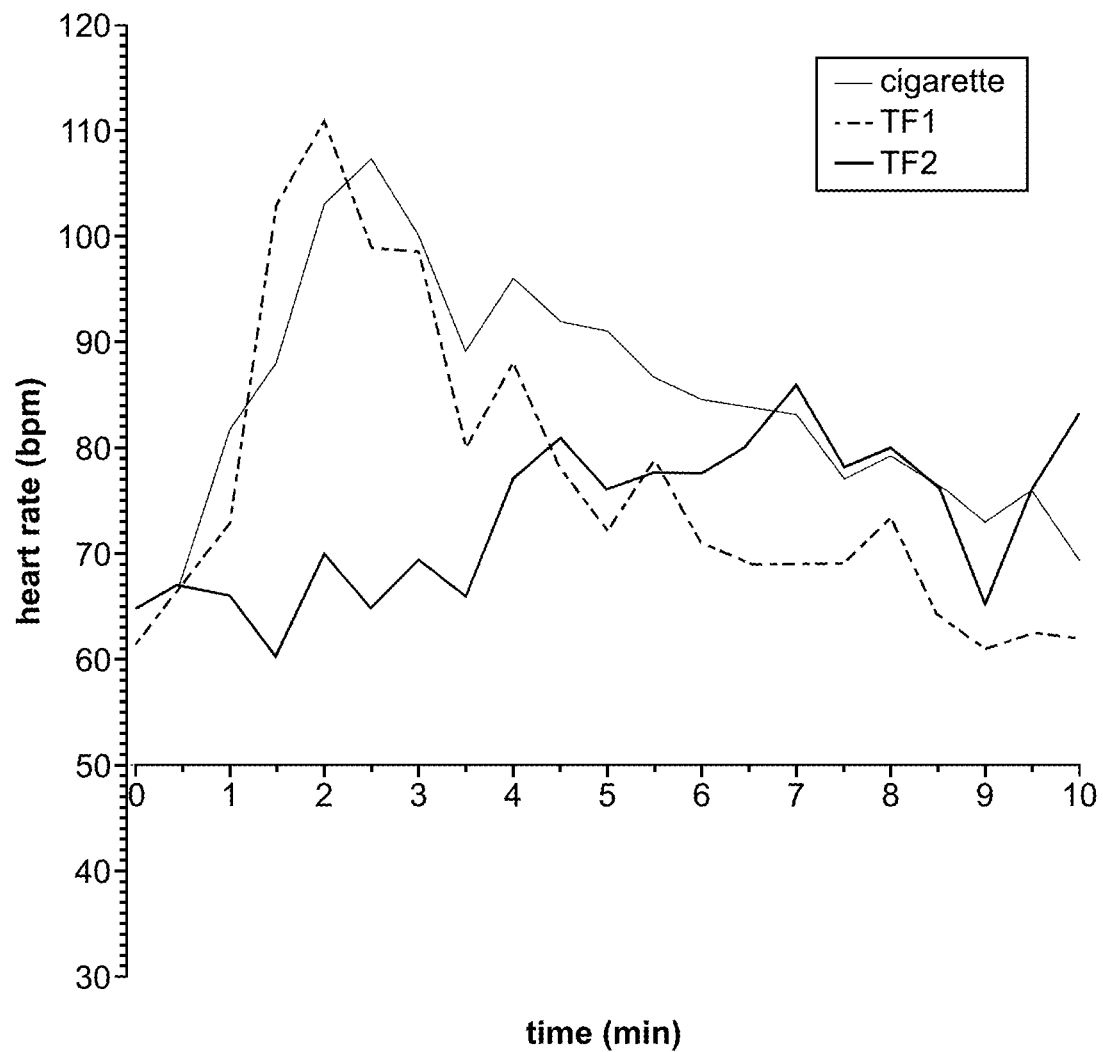
FIG. 2 illustrates results of heart rate data measured for ten minutes from start of puffing. Y-axis is heart rate (bpm) and X-axis represents duration of the test (0 to 10 minutes)

It is clearly shown in FIG. 2 that the test formulation with nicotine levulinate (TF1) causes a faster rise in heart rate than just nicotine (TF2). Also, TF1 more closely resembles the rate of increase for a cigarette. Other salts were tried and also found to increase heart rate relative to a pure nicotine solution. Thus, other suitable nicotine salts that cause the similar effect may be used in accordance with the practice of the present invention. For example, other keto acids (alpha-keto acids, beta-keto acids, gamma-keto acids, and the like) such as pyruvic acid, oxaloacetic acid, acetoacetic acid, and the like. This experience of increased heart rate comparable to that of a traditional burned cigarette has not been demonstrated or identified in other electronic cigarette devices, nor has it been demonstrated or identified in low temperature tobacco vaporization devices that do not burn the tobacco, even when a nicotine salt was used (a solution of 20% (W/W) or more of nicotine salt) as an additive to the tobacco. Thus the results from this experiment are surprising and unexpected.

In addition, the data appears to correlate well with the previous findings shown in FIG. 2.

As previously noted in the Satisfaction Study, the nicotine salts formulations with acids having vapor pressures between 20-300 mmHg @ 200° C. provide more satisfaction than the rest, with the exception of the nicotine salt formulation made with pyruvic acid, which has a boiling point of 165° C., as noted in FIG. 3. Based on the findings herein, it was anticipated that these nicotine salt formulations having either:

- a Vapor Pressure between 20-300 mmHg @ 200° C.,
- a Vapor Pressure >20 mmHg @ 200° C.,
- a difference between boiling point and melting point of at least 50° C., and a boiling point greater than 160° C., and a melting point less than 160° C.,
- a difference between boiling point and melting point of at least 50° C., and a boiling point greater than 160° C., and a melting point less than 160° C.,
- a difference between boiling point and melting point of at least 50° C., and a boiling point at most 40° C. less than operating temperature, and a melting point at least 40° C. lower than operating temperature, or
- a combination thereof produce one or more of the following effects:

$T_{max}$—Time to maximum blood concentration: Based on the results established herein, a user of an e-cigarette comprising the nicotine salt formulation will experience a comparable rate of physical and emotional satisfaction from using a formulation comprising a mixture of nicotine salts prepared with an appropriate acid at least 1.2× to 3× faster than using a formulation comprising a freebase nicotine. As illustrated in FIG. 1: Nicotine from a nicotine salts formulation appears to generate a heartbeat that is nearly 1.2 times that of a normal heart rate for an individual approximately 40 seconds after the commencement of puffing; whereas the nicotine from a nicotine freebase formulation appears to generate a heartbeat that is nearly 1.2 times that of a normal heart rate for an individual approximately 110 seconds after the commencement of puffing; a 2.75× difference in time to achieve a comparable initial satisfaction level.

Again this would not be inconsistent with the data from FIG. 2, where the data illustrated that at approximately 120 seconds (2 minutes), the heart rate of test participants reached a maximum of 105-110 bpm with either a regular cigarette or a nicotine salt formulation (TF1); whereas those same participants heart rates only reached a maximum of approximately 86 bpm at approximately 7 minutes with a nicotine freebase formulation (TF2); also a difference in effect of 1.2 times greater with nicotine salts (and regular cigarettes) versus freebase nicotine.

Further, when considering peak satisfaction levels (achieved at approximately 120 seconds from the initiation of puffing (time=0) and looking at the slope of the line for a normalized heart rate, the approximate slope of those nicotine salt formulations that exceeded the freebase nicotine formulation range between 0.0054 $hr_n$/sec and 0.0025 $hr_n$/sec. By comparison, the slope of the line for the freebase nicotine formulation is about 0.002. This would suggest that the concentration of available nicotine will be delivered to the user at a rate that is between 1.25 and 2.7 times faster than a freebase formulation.

In another measure of performance; $C_{max}$—Maximum blood nicotine concentration; it is anticipated that similar rates of increase will be measured in blood nicotine concentration, as those illustrated above. That is, it was anticipated based on the findings herein, and unexpected based on the art known to date, that there would be comparable $C_{max}$ between the common cigarette and certain nicotine salt formulations, but with a lower $C_{max}$ in a freebase nicotine solution.

Similarly, anticipated based on the findings herein, and unexpected based on the art known to date, that certain nicotine salt formulations would have higher rate of nicotine uptake levels in the blood at early time periods. Indeed, Example 8 presents data for multiple salt formulations consistent with these predictions which were made based on the findings and tests noted herein, and unexpected compared to the art available to date.

Example 7: Heart Rate Study of Nicotine Solutions Via e-Cigarette

Exemplary formulations of nicotine levulinate, nicotine benzoate, nicotine succinate, nicotine salicylate, nicotine malate, nicotine pyruvate, nicotine citrate, nicotine sorbate, nicotine laurate, nicotine freebase, and a control of propylene glycol are prepared as noted in Example 1 and are administered in the same fashion by an electronic cigarette to the same human subject. About 0.5 mL of each solution is loaded into an "eRoll" cartridge atomizer (joyetech.com) to be used in the study. The atomizer is then attached to an "eRoll" e-cigarette (same manufacturer). The operating temperature of the e-cigarette is from about 150° C. to about 250° C., or from about 180° C. to about 220° C.

Heart rate measurements are taken for 6 minutes; from 1 minute before start of puffing, for 3 minutes during puffing, and continuing until 2 minutes after end of puffing. The test participant takes 10 puffs over 3 minutes in each case. The base heart rate is the average heart rate over the first 1 minute before start of puffing. Heart rate after puffing started is averaged over 20-second intervals. Normalized heart rate is defined as the ratio between individual heart rate data point and the base heart rate. Final results are presented as normalized heart rate.

Example 8: Blood Plasma Testing

Blood plasma testing was conducted on three subjects (n=3). Eight test articles were used in this study: one reference cigarette and seven blends used in an e-cigarette device having an operating temperature of the e-cigarette from about 150° C. to about 250° C., or from about 180° C. to about 220° C. The reference cigarette was Pall Mall (New Zealand). Seven blends were tested in the e-cigarette: 2% free base, 2% benzoate, 4% benzoate, 2% citrate, 2% malate, 2% salicylate, and 2% succinate. Except for 2% succinate (n=1), all other blends have n=3. The seven blends were liquid formulations prepared as described in Example 1.

The concentration of nicotine in each of the formulations was confirmed using UV spectrophotometer (Cary 60, manufactured by Agilent). The sample solutions for UV analysis were made by dissolving 20 mg of each of the formulations in 20 mL 0.3% HCl in water. The sample solutions were then scanned in UV spectrophotometer and the characteristic nicotine peak at 259 nm was used to quantify nicotine in the sample against a standard solution of 19.8 μg/mL nicotine in the same diluent. The standard solution was prepared by first dissolving 19.8 mg nicotine in 10 mL 0.3% HCl in water followed by a 1:100 dilution with 0.3% HCl in water. Nicotine concentrations reported for all formulations were within the range of 95%-105% of the claimed concentrations All subjects were able to consume 30-55 mg of the liquid formulation of each tested blend using the e-cigarette.

Literature results: C. Bullen et al, Tobacco Control 2010, 19:98-103 Cigarette (5 min adlib, n=9): $T_{max}$=14.3 (8.8-19.9), $C_{max}$=13.4 (6.5-20.3) 1.4% E-cig (5 min adlib, n=8): $T_{max}$=19.6 (4.9-34.2), $C_{max}$=1.3 (0.0-2.6) Nicorette Inhalator (20 mg/20 min, n=10): $T_{max}$=32.0 (18.7-45.3), $C_{max}$=2.1 (1.0-3.1)

Figure 4:
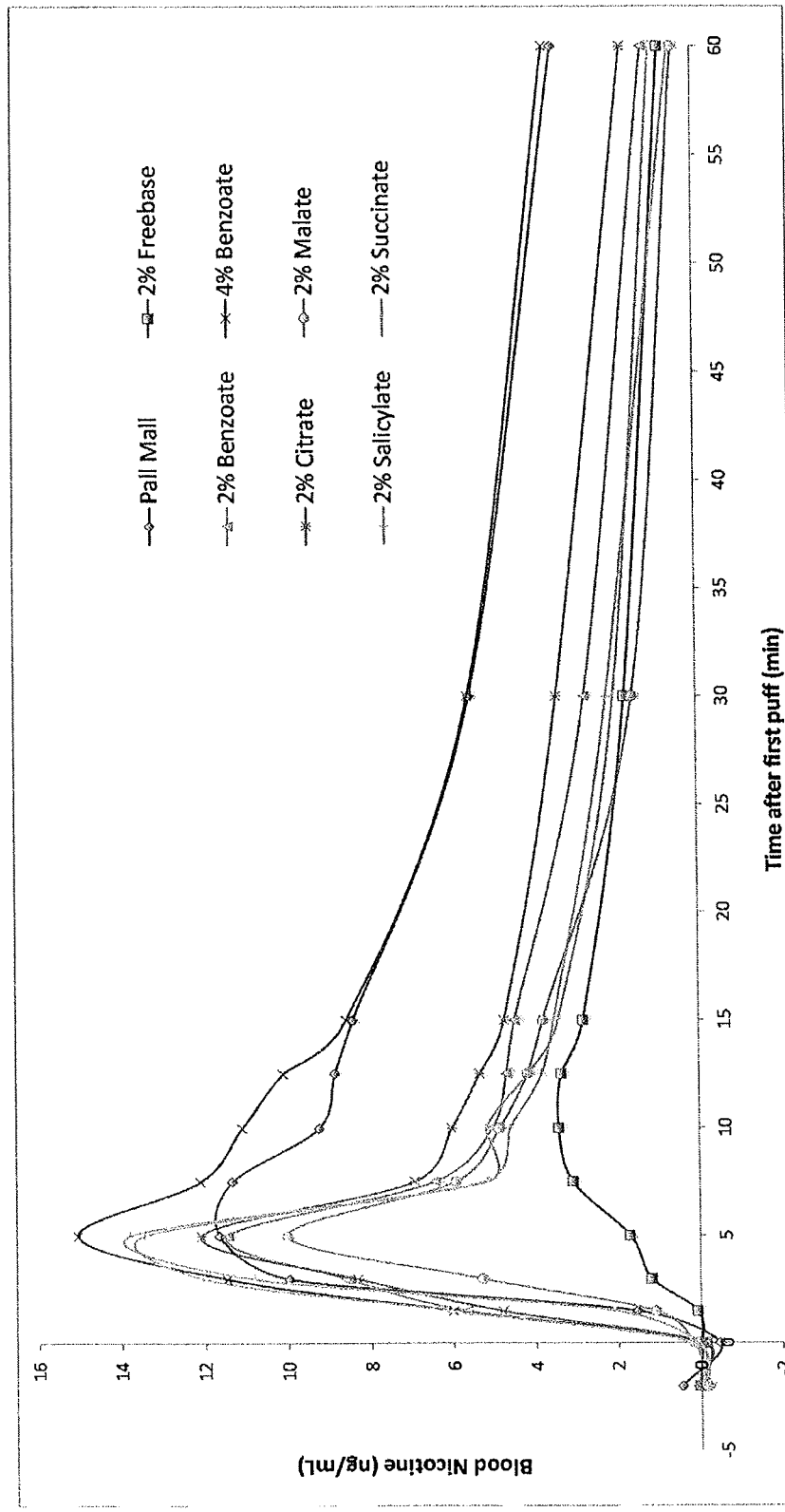
FIG. 4 illustrates the pharmacokinetic profiles for eight test articles in a blood plasma study.

Estimated $C_{max}$ of 2% nicotine blends:

$C_{max}$=Mass consumed*Strength*Bioavailability/(Vol of Distribution*Body Weight)=40 mg*2%*80%/ (2.6 L/kg*75 kg)=3.3 ng/mL Estimated $C_{max}$ of 4% nicotine blends:

$C_{max}$=Mass consumed*Strength*Bioavailability/(Vol of Distribution*Body Weight)=40 mg*4%*80%/ (2.6 L/kg*75 kg)=6.6 ng/mL Pharmacokinetic profiles of the blood plasma testing are shown in FIG. 4; showing blood nicotine concentrations (ng/mL) over time after the first puff (inhalation) of the aerosol from the e-cigarette or the smoke of the Pall Mall. Ten puffs were taken at 30 sec intervals starting at time=0 and continuing for 4.5 minutes. For ease of reference and review of FIG. 4, at the 5-minute timepoint, the curves on the graph show from top to bottom (highest average blood nicotine concentration to lowest average blood nicotine concentration) are 4% benzoate, 2% succinate, 2% salicylate, 2% citrate, Pall Mall cigarette, 2% benzoate, 2% malate, and 2% free base blend. Although noted as highest to lowest at this time point, this is not to say that there is a statistically significant difference between any of the salt formulations, or between any of the salt formulations and the Pall Mall cigarette. However, it is possible there may be a statistically significant difference between the $C_{max}$ of particular salt formulations, and it is also likely based on the data shown in FIG. 4 and in other studies herein that the freebase formulation is statistically different from salt formulations and/or the Pall Mall with respect to $C_{max}$, since it appears lower than others tested at several time points. One of skill in the art, upon review of the disclosure herein could properly power a test to determine actual statistically-based differences between one or more formulations and the cigarette, or between the formulations themselves in an e-cigarette. For ease of reference Tables 1 & 2 present the amount of nicotine detected (as an average of all users) for each formulation and the Pall Mall, presented in ng/mL, along with $C_{max}$ and $T_{max}$ and AUC. Data from these tables, along with the raw data therefore, was used to generate FIGS. 4, 5, and 6.

TABLE 1

| Time | Pall Mall | 2% Freebase | 2% Benzoate | 4% Benzoate |
|---|---|---|---|---|
| −2 | 0.46 | 0.03 | 0.09 | 0.05 |
| 0 | −0.46 | −0.03 | −0.09 | −0.05 |
| 1.5 | 1.54 | 0.08 | 5.67 | 6.02 |
| 3 | 9.98 | 1.19 | 8.60 | 11.47 |
| 5 | 11.65 | 1.70 | 11.44 | 15.06 |
| 7.5 | 11.34 | 3.09 | 6.43 | 12.12 |
| 10 | 9.24 | 3.42 | 5.03 | 11.08 |
| 12.5 | 8.85 | 3.35 | 4.68 | 10.10 |
| 15 | 8.40 | 2.81 | 4.47 | 8.57 |
| 30 | 5.51 | 1.74 | 2.72 | 5.56 |
| 60 | 3.39 | 0.79 | 1.19 | 3.60 |
| $T_{max}$ (min) | 5.17 | 10.00 | 6.67 | 5.83 |
| $C_{max}$ (ng/mL) | 11.65 | 3.42 | 11.44 | 15.06 |
| AUC (ng*min/mL) | 367.5 | 106.2 | 207.8 | 400.2 |

TABLE 2

| Time | 2% Citrate | 2% Malate | 2% Salicylate | 2% Succinate |
|---|---|---|---|---|
| −2 | 0.06 | −0.17 | −0.19 | −0.06 |
| 0 | −0.06 | 0.17 | 0.19 | 0.06 |
| 1.5 | 4.80 | 1.09 | 6.14 | 2.10 |
| 3 | 8.33 | 5.30 | 12.04 | 10.81 |
| 5 | 12.09 | 10.02 | 13.46 | 13.81 |
| 7.5 | 6.93 | 5.93 | 5.21 | 5.15 |
| 10 | 6.01 | 4.85 | 4.60 | 5.18 |
| 12.5 | 5.34 | 4.17 | 3.83 | 4.17 |
| 15 | 4.72 | 3.79 | 3.52 | 3.41 |
| 30 | 3.40 | 1.56 | 2.19 | 2.01 |
| 60 | 1.70 | 0.46 | 0.55 | 1.00 |
| $T_{max}$ (min) | 5.83 | 5.00 | 4.33 | 5.00 |
| $C_{max}$ (ng/mL) | 12.09 | 10.02 | 13.46 | 13.81 |
| AUC (ng*min/mL) | 238.0 | 146.1 | 182.9 | 179.5 |

Figure 5:
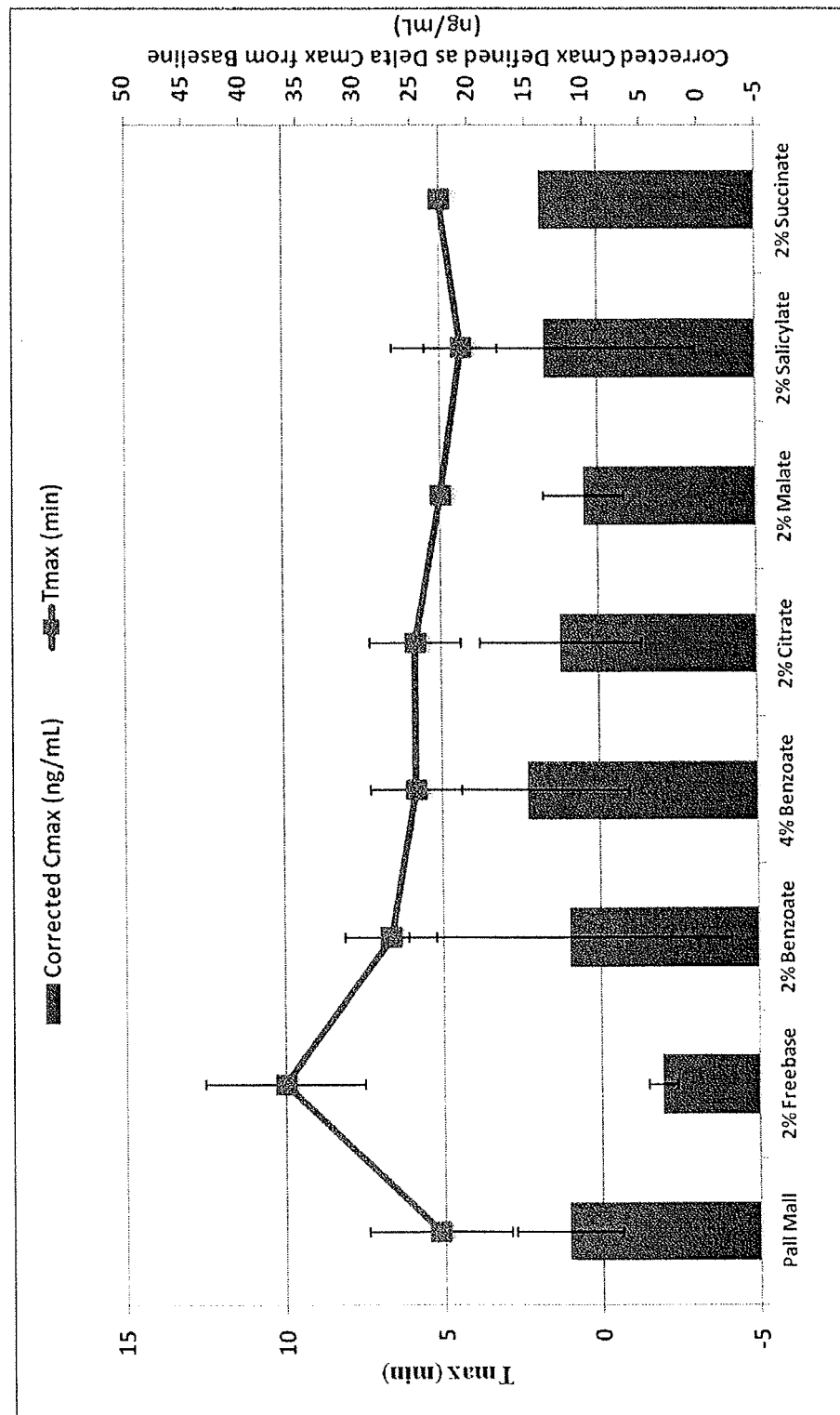
FIG. 5 illustrates the comparison of $C_{max}$ and $T_{max}$ for eight test articles in a blood plasma study.
Figure 6:
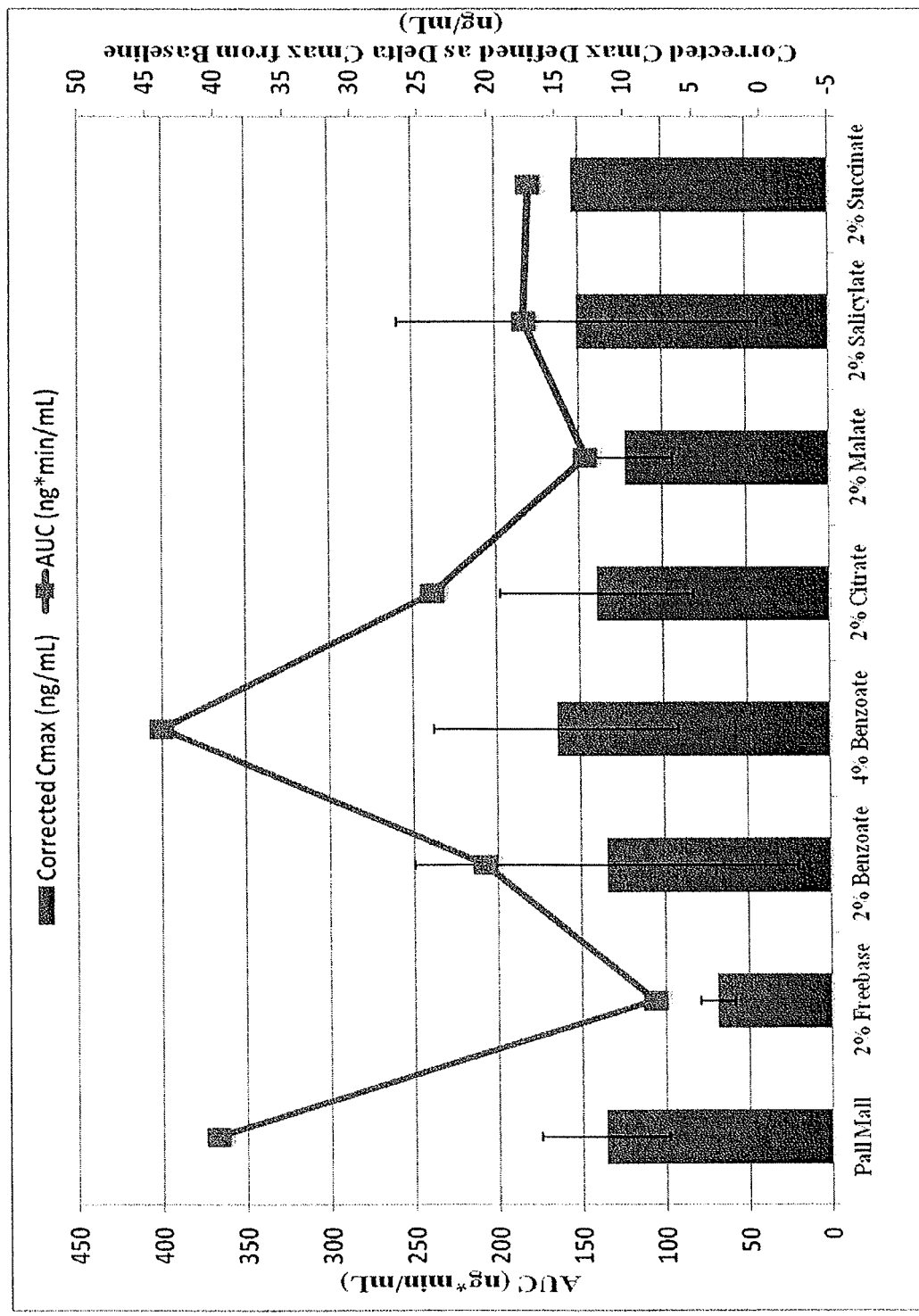
FIG. 6 illustrates the comparison of $C_{max}$ and AUC for eight test articles in a blood plasma study.

Comparison of $T_{max}$ and $C_{max}$ of the seven blends and reference cigarette are shown in FIG. 5. Comparison of $C_{max}$ and AUC of the seven blends and reference cigarette are shown in FIG. 6. Due to the time limit of the wash-period, baseline blood nicotine concentration (at t=−2 and t=0 min) was higher for samples consumed at a later time on the test day. The data in FIGS. 4-6 show corrected blood nicotine concentration values (i.e. apparent blood nicotine concentration at each time point minus baseline nicotine concentration of the same sample).

Rates of nicotine uptake in the blood of the users of each sample within the first 90 seconds are shown in Table 3.

TABLE 3

| Sample | Rate of nicotine uptake (ng/mL/min) |
|---|---|
| 2% Salicylate | 4.09 |
| 2% Benzoate | 3.78 |
| 2% Citrate | 3.20 |
| 2% Succinate | 1.40 |
| Pall Mall (reference) | 1.03 |
| 2% Malate | 0.73 |
| 2% Freebase | 0.05 |
| 4% Benzoate | 4.01 |

Although the $T_{max}$ and $C_{max}$ values are comparable between the tested blends and the reference cigarette (with the exception of the 2% free base blend), the rates of nicotine absorption within the first 90 seconds differed among the test articles. In particular, four blends (2% salicylate, 2% benzoate, 4% benzoate, and 2% citrate) showed markedly higher rates of absorption within the first 90 seconds compared to the other blends and with the reference cigarette. These four blends contain salts (salicylate, benzoate, and citrate) which performed well in the Satisfaction Study of Example 3. Moreover, 2% benzoate and 4% benzoate had comparable rates of absorption, suggesting that a lower concentration of nicotinic salt may not adversely impact the rate of absorption.

Example 9: Blood Plasma Testing

Blood plasma testing is conducted on 24 subjects (n=24). Eight test articles are used in this study: one reference cigarette and seven blends delivered to a user in an e-cigarette as an aerosol. The operating temperature of the e-cigarette is from about 150° C. to about 250° C., or from about 180° C. to about 220° C. The reference cigarette is Pall Mall (New Zealand). Seven blends are tested: 2% free base, 2% benzoate, 4% benzoate, 2% citrate, 2% malate, 2% salicylate, and 2% succinate. The seven blends are liquid formulations prepared according to protocols similar to that described infra and in Example 1.

All subjects are to consume 30-55 mg of the liquid formulation of each tested blend. Ten puffs are to be taken at 30 sec intervals starting at time=0 and continuing for 4.5 minutes. Blood plasma testing is to occur for at least 60 minutes from the first puff (t=0) Pharmacokinetic data (e.g., $C_{max}$, $T_{max}$, AUC) for nicotine in the plasma of users are obtained at various time periods during those 60 minutes, along with rates of nicotine absorption within the first 90 seconds for each test article.

Example 10: Blood Plasma Testing

Blood plasma testing is conducted on twenty-four subjects (n=24). Eleven test articles are used in this study: one reference cigarette and ten blends delivered to a user in an e-cigarette as an aerosol. The reference cigarette is Pall Mall (New Zealand). The operating temperature of the e-cigarette is from about 150° C. to about 250° C., or from about 180° C. to about 220° C. Ten blends are tested: 2% free base, 2% benzoate, 2% sorbate, 2% pyruvate, 2% laurate, 2% levulinate, 2% citrate, 2% malate, 2% salicylate, and 2% succinate. The ten blends are liquid formulations prepared according to protocols similar to that described infra and in Example 1.

All subjects are to consume 30-55 mg of the liquid formulation of each tested blend. Ten puffs are to be taken at 30 sec intervals starting at time=0 and continuing for 4.5 minutes. Blood plasma testing is to occur for at least 60 minutes from the first puff (t=0). Pharmacokinetic data (e.g., $C_{max}$, $T_{max}$, AUC) for nicotine in the plasma of users are obtained at various time periods during those 60 minutes, along with rates of nicotine absorption within the first 90 seconds for each test article.

Example 11: Blood Plasma Testing

Blood plasma testing is conducted on twenty-four subjects (n=24). Twenty-one test articles are used in this study: one reference cigarette and twenty blends delivered to a user in an e-cigarette as an aerosol. The reference cigarette is Pall Mall (New Zealand). The operating temperature of the e-cigarette is from about 150° C. to about 250° C., or from about 180° C. to about 220° C. Twenty blends are tested: 2% free base, 4% free base, 2% benzoate, 4% benzoate, 2% sorbate, 4% sorbate, 2% pyruvate, 4% pyruvate, 2% laurate, 4% laurate, 2% levulinate, 4% levulinate, 2% citrate, 4% citrate, 2% malate, 4% malate, 2% salicylate, 4% salicylate, 2% succinate, and 4% succinate. The twenty blends are liquid formulations prepared according to protocols similar to that described infra and in Example 1.

All subjects are to consume 30-55 mg of the liquid formulation of each tested blend. Ten puffs are to be taken at 30 sec intervals starting at time=0 and continuing for 4.5 minutes. Blood plasma testing is to occur for at least 60 minutes from the first puff (t=0). Pharmacokinetic data (e.g., $C_{max}$, $T_{max}$, AUC) for nicotine in the plasma of users are obtained at various time periods during those 60 minutes, along with rates of nicotine absorption within the first 90 seconds for each test article.

Example 12: Blood Plasma Testing

Blood plasma testing is conducted on twenty-four subjects (n=24). Twenty-one test articles are used in this study: one reference cigarette and twenty blends delivered to a user in an e-cigarette as an aerosol. The reference cigarette is Pall Mall (New Zealand). The operating temperature of the e-cigarette is from about 150° C. to about 250° C., or from about 180° C. to about 220° C. Twenty blends are tested: 2% free base, 1% free base, 2% benzoate, 1% benzoate, 2% sorbate, 1% sorbate, 2% pyruvate, 1% pyruvate, 2% laurate, 1% laurate, 2% levulinate, 1% levulinate, 2% citrate, 1% citrate, 2% malate, 1% malate, 2% salicylate, 1% salicylate, 2% succinate, and 1% succinate. The twenty blends are liquid formulations prepared according to protocols similar to that described infra and in Example 1.

All subjects are to consume 30-55 mg of the liquid formulation of each tested blend. Ten puffs are to be taken at 30 sec intervals starting at time=0 and continuing for 4.5 minutes. Blood plasma testing is to occur for at least 60 minutes from the first puff (t=0). Pharmacokinetic data (e.g., $C_{max}$, $T_{max}$, AUC) for nicotine in the plasma of users are obtained at various time periods during those 60 minutes, along with rates of nicotine absorption within the first 90 seconds for each test article.

Further understanding may be gained through contemplation of the numbered embodiments below.

1. A method of delivering nicotine to a user comprising operating an electronic cigarette to a user wherein the electronic cigarette comprises a nicotine salt formulation comprising a nicotine salt in a biologically acceptable liquid carrier wherein an acid used to form said nicotine salt is characterized by vapor pressure >20 mmHg at 200° C., and inhaling an aerosol generated from the nicotine salt formulation heated by the electronic cigarette.

2. A method of delivering nicotine to a user comprising operating an electronic cigarette to a user wherein the electronic cigarette comprises a nicotine salt formulation comprising a nicotine salt in a biologically acceptable liquid carrier wherein an acid used to form said nicotine salt is characterized by vapor pressure of about 20 to 200 mmHg at 200° C., and inhaling an aerosol generated from the nicotine salt formulation heated by the electronic cigarette.

3. A method of delivering nicotine to a user comprising operating an electronic cigarette wherein the electronic cigarette comprises a nicotine salt formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point, and inhaling an aerosol generated from the nicotine salt formulation heated by the electronic cigarette.

4. A method of delivering nicotine to a user comprising providing an electronic cigarette to a user wherein the electronic cigarette comprises a nicotine salt formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point, and inhaling an aerosol generated from the nicotine salt formulation heated by the electronic cigarette.

5. The method of any one of embodiments 1-3, wherein an operating temperature is from 150° C. to 250° C.

6. The method of any one of embodiments 1-3, wherein an operating temperature is from 180° C. to 220° C.

7. The method any one of embodiments 1-3, wherein an operating temperature is about 200° C.

8. The method of embodiment 4, wherein the operating temperature is from 150° C. to 250° C.

9. The method of embodiment 4, wherein the operating temperature is from 180° C. to 220° C.

10. The method of embodiment 4, wherein the operating temperature is about 200° C.

11. The method any one of embodiments 1-10, wherein the aerosol comprises condensate of the nicotine salt.

12. The method any one of embodiments 1-10, wherein the aerosol comprises condensate of freebase nicotine.

13. The method any one of embodiments 1-10, wherein the aerosol comprises condensate of freebase nicotine and condensate of the carrier.

14. The method any one of embodiments 1-10, wherein the aerosol comprises condensate of freebase nicotine and condensate of the acid.

15. The method any one of embodiments 1-14, wherein the aerosol comprises condensate in particle sizes from about 0.1 microns to about 5 microns.

16. The method any one of embodiments 1-14, wherein the aerosol comprises condensate in particle sizes from about 0.1 microns to about 1 or 2 microns.

17. The method any one of embodiments 1-14, wherein the aerosol comprises condensate in particle sizes from about 0.1 microns to about 0.7 microns.

18. The method any one of embodiments 1-14, wherein the aerosol comprises condensate in particle sizes from about 0.3 microns to about 0.4 microns.

19. The method any one of embodiments 1-18, wherein the acid is a carboxylic acid.

20. The method of any one of embodiments 1-18, wherein the acid used to form said nicotine salt is an organic acid.

21. The method of embodiment 20, wherein the organic acid is monocarboxylic acid, aromatic acid, or keto acid.

22. The method of embodiment 20, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

23. The method of any one of embodiments 1-18, wherein the acid used to form the nicotine salt is salicylic acid.

24. The method of any one of embodiments 1-18, wherein the acid used to form the nicotine salt is benzoic acid.

25. The method of any one of embodiments 1-18, wherein the acid used to form the nicotine salt is pyruvic acid.

26. The method of any one of embodiments 1-18, wherein the acid used to form the nicotine salt is sorbic acid.

27. The method of any one of embodiments 1-18, wherein the acid used to form the nicotine salt is lauric acid.

28. The method of any one of embodiments 1-18, wherein the acid used to form the nicotine salt is levulinic acid.

29. The method of any one of embodiments 1-18, wherein said nicotine salt comprises nicotine pyruvate.

30. The method of any one of embodiments 1-18, wherein said nicotine salt comprises nicotine salicylate.

31. The method of any one of embodiments 1-18, wherein said nicotine salt comprises nicotine sorbate.

32. The method of any one of embodiments 1-18, wherein said nicotine salt comprises nicotine laurate.

33. The method of any one of embodiments 1-18, wherein said nicotine salt comprises nicotine levulinate.

34. The method of any one of embodiments 1-18, wherein said nicotine salt comprises nicotine benzoate.

35. The method of any one of embodiments 1-34, wherein the liquid carrier comprises glycerol, propylene glycol, trimethylene glycol, water, ethanol or combinations thereof.

36. The method of any one of embodiments 1-34, wherein the liquid carrier comprises propylene glycol and vegetable glycerin.

37. The method of any one of embodiments 1-34, wherein the liquid carrier comprises 20% to 50% of propylene glycol and 80% to 50% of vegetable glycerin.

38. The method of any one of embodiments 1-34, wherein the liquid carrier comprises 30% propylene glycol and 70% vegetable glycerin.

39. The method of any one of embodiments 1-38, wherein the nicotine salt is in an amount that forms about 0.5% to about 20% nicotine in the inhalable aerosol.

40. The method of any one of embodiments 1-38, wherein the nicotine salt is in an amount that forms about 1% to about 20% nicotine in the inhalable aerosol.

41. The method of any one of embodiments 1-40, wherein the liquid formulation has a nicotine concentration of about 1% (w/w) to about 25% (w/w).

42. The method of any one of embodiments 1-40, wherein the liquid formulation has a nicotine concentration of about 1% (w/w) to about 20% (w/w).

43. The method of any one of embodiments 1-40, wherein the liquid formulation has a nicotine concentration of about 1% (w/w) to about 18% (w/w).

44. The method of any one of embodiments 1-40, wherein the liquid formulation has a nicotine concentration of about 1% (w/w) to about 15% (w/w).

45. The method of any one of embodiments 1-40, wherein the liquid formulation has a nicotine concentration of about 4% (w/w) to about 12% (w/w).

46. The method of any one of embodiments 1-40, wherein the liquid formulation has a nicotine concentration of about 4% (w/w).

47. The method of any one of embodiments 1-40, wherein the liquid formulation has a nicotine concentration of about 2% (w/w).

48. The method of any one of embodiments 1-47, wherein the formulation further comprises a flavorant.

49. The method of any one of embodiments 1-48, wherein the formulation is non-corrosive to an electronic cigarette.

50. The method of any one of embodiments 1-49, wherein the acid is stable at and below operating temperature or about 200° C.

51. The method of any one of embodiments 1-50, wherein the acid does not decompose at and below operating temperature or about 200° C.

52. The method of any one of embodiments 1-51, wherein the acid does not oxidize at and below operating temperature or about 200° C.

53. The method of any one of embodiments 1-52, wherein the formulation is non-corrosive to the electronic cigarette.

54. The method of any one of embodiments 1-53, wherein the formulation is non-toxic to a user of the electronic cigarette.

55. The method of any one of embodiments 1-54, wherein the formulation further comprises one or more additional nicotine salts in a biologically acceptable liquid carrier suitable for generating the inhalable aerosol upon heating.

56. The method of embodiment 55, wherein a second acid used to form the additional nicotine salt is selected from the group consisting of salicylic acid, sorbic acid, benzoic acid, pyruvic acid, lauric acid, and levulinic acid.

57. A method of delivering nicotine to the blood of a user, said method comprising providing an aerosol that is inhaled by the user from an electronic cigarette that comprises a nicotine salt formulation wherein providing the aerosol comprises the electronic cigarette heating the formulation thereby generating the aerosol, wherein the aerosol is effective in delivering a level of nicotine in the blood of the user that is at least 5 ng/mL at about 1.5 minutes after a first puff of ten puffs of the aerosol, each puff taken at 30 second intervals.

58. The method of embodiment 54, wherein the nicotine salt formulation comprises a nicotine salt in a biologically acceptable liquid carrier wherein an acid used to form said nicotine salt is characterized by vapor pressure >20 mmHg at 200° C.

59. The method of embodiment 54, wherein the nicotine salt formulation comprises a nicotine salt in a biologically acceptable liquid carrier wherein an acid used to form said nicotine salt is characterized by vapor pressure of about 20 to 200 mmHg at 200° C.

60. The method of embodiment 54, wherein the nicotine salt formulation comprises a nicotine salt in a biologically acceptable liquid carrier wherein an acid used to form said nicotine salt is further characterized by a melting point <160° C., a boiling point >160° C., and at least a 50-degree difference between the melting point and the boiling point.

61. The method of any one of embodiments 57-60, wherein the heating of the formulation is at a temperature from 150° C. to 250° C.

62. The method of any one of embodiments 57-60, wherein the heating of the formulation is at a temperature from 180° C. to 220° C.

63. The method of any one of embodiments 57-60, wherein the heating of the formulation is at a temperature of about 200° C.

64. The method of embodiment 54, wherein the nicotine salt formulation comprises a nicotine salt in a biologically acceptable liquid carrier wherein an acid used to form said nicotine salt is further characterized by a melting point at least 40 degrees lower than the operating temperature of the electronic cigarette, a boiling point no more than 40 degrees lower than the operating temperature of the electronic cigarette, and at least a 50-degree difference between the melting point and the boiling point; and the operating temperature is 200° C.

65. The method of any one of embodiments 57-64, wherein the Cmax is over 10 ng/mL on average.

66. The method of any one of embodiments 57-64, wherein the Cmax is over 11 ng/mL on average.

67. The method of any one of embodiments 57-64, wherein the Cmax is between 10 ng/mL and 16 ng/mL on average.

68. The method of any one of embodiments 57-64, wherein the Cmax is between 11 ng/mL and 15 ng/mL on average.

69. The method of any one of embodiments 57-64, wherein the Cmax is between 11 ng/mL and 14 ng/mL on average.

70. The method of any one of embodiments 57-69, wherein the Tmax under 10 minutes on average.

71. The method of any one of embodiments 57-69, wherein the Tmax is under 9 minutes on average.

72. The method of any one of embodiments 57-69, wherein the Tmax is under 8 minutes on average.

73. The method of any one of embodiments 57-69, wherein the Tmax is under 7 minutes on average.

74. The method of any one of embodiments 54-63, wherein the Tmax is from 3 minutes to 10 minutes on average.

75. The method of any one of embodiments 57-69, wherein the Tmax is from 3 minutes to 7.5 minutes on average.

76. The method of any one of embodiments 57-75, wherein the aerosol comprises condensate of the nicotine salt.

77. The method of any one of embodiments 57-75, wherein the aerosol comprises condensate of freebase nicotine.

78. The method of any one of embodiments 57-75, wherein the aerosol comprises condensate of freebase nicotine and condensate of the carrier.

79. The method of any one of embodiments 57-75, wherein the aerosol comprises condensate of freebase nicotine and condensate of the acid.

80. The method of any one of embodiments 57-79, wherein the aerosol comprises condensate in particle sizes from about 0.1 microns to about 5 microns.

81. The method of any one of embodiments 57-79, wherein the aerosol comprises condensate in particle sizes from about 0.1 microns to about 1 or 2 microns.

82. The method of any one of embodiments 57-79, wherein the aerosol comprises condensate in particle sizes from about 0.1 microns to about 0.7 microns.

83. The method of any one of embodiments 57-79, wherein the aerosol comprises condensate in particle sizes from about 0.3 microns to about 0.4 microns.

84. The method of any one of embodiments 57-83, wherein the acid is a carboxylic acid.

85. The method of any one of embodiments 57-83, wherein the acid used to form said nicotine salt is an organic acid.

86. The method of embodiment 85, wherein the organic acid is monocarboxylic acid, aromatic acid, or keto acid.

87. The method of embodiment 85, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

88. The method of any one of embodiments 57-83, wherein the acid used to form the nicotine salt is salicylic acid.

89. The method of any one of embodiments 57-83, wherein the acid used to form the nicotine salt is benzoic acid.

90. The method of any one of embodiments 57-83, wherein the acid used to form the nicotine salt is pyruvic acid.

91. The method of any one of embodiments 57-83, wherein the acid used to form the nicotine salt is sorbic acid.

92. The method of any one of embodiments 57-83, wherein the acid used to form the nicotine salt is lauric acid.

93. The method of any one of embodiments 57-83, wherein the acid used to form the nicotine salt is levulinic acid.

94. The method of any one of embodiments 57-83, wherein said nicotine salt comprises nicotine pyruvate.

95. The method of any one of embodiments 57-83, wherein said nicotine salt comprises nicotine salicylate.

96. The method of any one of embodiments 57-83, wherein said nicotine salt comprises nicotine sorbate.

97. The method of any one of embodiments 57-83, wherein said nicotine salt comprises nicotine laurate.

98. The method of any one of embodiments 57-83, wherein said nicotine salt comprises nicotine levulinate.

99. The method of any one of embodiments 57-83, wherein said nicotine salt comprises nicotine benzoate.

100. The method of any one of embodiments 57-99, wherein the liquid carrier comprises glycerol, propylene glycol, trimethylene glycol, water, ethanol or combinations thereof.

101. The method of any one of embodiments 57-99, wherein the liquid carrier comprises propylene glycol and vegetable glycerin.

102. The method of any one of embodiments 57-99, wherein the liquid carrier comprises 20% to 50% of propylene glycol and 80% to 50% of vegetable glycerin.

103. The method of any one of embodiments 57-99, wherein the liquid carrier comprises 30% propylene glycol and 70% vegetable glycerin.

104. The method of any one of embodiments 57-103, wherein the nicotine salt is in an amount that forms about 0.5% to about 20% nicotine in the inhalable aerosol.

105. The method of any one of embodiments 57-103, wherein the nicotine salt is in an amount that forms about 1% to about 20% nicotine in the inhalable aerosol.

106. The method of any one of embodiments 57-105, wherein the liquid formulation has a nicotine concentration of about 1% (w/w) to about 25% (w/w).

107. The method of any one of embodiments 57-105, wherein the liquid formulation has a nicotine concentration of about 1% (w/w) to about 20% (w/w).

108. The method of any one of embodiments 57-105, wherein the liquid formulation has a nicotine concentration of about 1% (w/w) to about 18% (w/w).

109. The method of any one of embodiments 57-105, wherein the liquid formulation has a nicotine concentration of about 1% (w/w) to about 15% (w/w).

110. The method of any one of embodiments 57-105, wherein the liquid formulation has a nicotine concentration of about 4% (w/w) to about 12% (w/w).

111. The method of any one of embodiments 57-105, wherein the liquid formulation has a nicotine concentration of about 4% (w/w).

112. The method of any one of embodiments 57-105, wherein the liquid formulation has a nicotine concentration of about 2% (w/w).

113. The method of any one of embodiments 57-112, wherein the formulation further comprises a flavorant.

114. The method of any one of embodiments 57-113, wherein the formulation is non-corrosive to an electronic cigarette.

115. The method of any one of embodiments 57-114, wherein the acid is stable at and below operating temperature or about 200° C.

116. The method of any one of embodiments 57-115, wherein the acid does not decompose at and below operating temperature or about 200° C.

117. The method of any one of embodiments 57-116, wherein the acid does not oxidize at and below operating temperature or about 200° C.

118. The method of any one of embodiments 57-117, wherein the formulation is non-corrosive to the electronic cigarette.

119. The method of any one of embodiments 57-118, wherein the formulation is non-toxic to a user of the electronic cigarette.

120. The method of any one of embodiments 57-119, wherein the formulation further comprises one or more additional nicotine salts in a biologically acceptable liquid carrier suitable for generating the inhalable aerosol upon heating.

121. The method of embodiment 120, wherein a second acid used to form the additional nicotine salt is selected from the group consisting of salicylic acid, sorbic acid, benzoic acid, pyruvic acid, lauric acid, and levulinic acid.

122. A nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is characterized by vapor pressure >20 mmHg at 200° C.

123. A nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is characterized by vapor pressure of about 20 to 200 mmHg at 200° C.

124. A nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

125. A nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

126. The nicotine salt liquid formulation in the electronic cigarette of any one of embodiments 122-124, wherein the electronic cigarette heats the nicotine salt formulation to an operating temperature from 150° C. to 250° C.

127. The nicotine salt liquid formulation in the electronic cigarette of any one of embodiments 122-124, wherein the electronic cigarette heats the nicotine salt formulation to an operating temperature from 180° C. to 220° C.

128. The nicotine salt liquid formulation in the electronic cigarette of any one of embodiments 122-124, wherein the electronic cigarette heats the nicotine salt formulation to an operating temperature of about 200° C.

129. The nicotine salt liquid formulation in the electronic cigarette of embodiment 125, wherein the operating temperature is from 150° C. to 250° C.

130. The nicotine salt liquid formulation in the electronic cigarette of embodiment 125, wherein the operating temperature is from 180° C. to 220° C.

131. The nicotine salt liquid formulation in the electronic cigarette of embodiment 125, wherein the operating temperature is about 200° C.

132. The nicotine salt liquid formulation in the electronic cigarette of any one of embodiments 122-131, wherein the acid is a carboxylic acid.

133. The nicotine salt liquid formulation in the electronic cigarette of any one of embodiments 122-131, wherein the acid used to form said nicotine salt is an organic acid.

134. The nicotine salt liquid formulation in the electronic cigarette of embodiment 133, wherein the organic acid is monocarboxylic acid, aromatic acid, or keto acid.

135. The nicotine salt liquid formulation in the electronic cigarette of embodiment 133, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

136. The nicotine salt liquid formulation in the electronic cigarette of any one of embodiments 122-131, wherein the acid used to form the nicotine salt is salicylic acid.

137. The nicotine salt liquid formulation in the electronic cigarette of any one of embodiments 122-131, wherein the acid used to form the nicotine salt is benzoic acid.

138. The nicotine salt liquid formulation in the electronic cigarette of any one of embodiments 122-131, wherein the acid used to form the nicotine salt is pyruvic acid.

139. The nicotine salt liquid formulation in the electronic cigarette of any one of embodiments 122-131, wherein the acid used to form the nicotine salt is sorbic acid.

140. The nicotine salt liquid formulation in the electronic cigarette of any one of embodiments 122-131, wherein the acid used to form the nicotine salt is lauric acid.

141. The nicotine salt liquid formulation in the electronic cigarette of any one of embodiments 122-131, wherein the acid used to form the nicotine salt is levulinic acid.

142. The nicotine salt liquid formulation in the electronic cigarette of any one of embodiments 122-131, wherein said nicotine salt comprises nicotine pyruvate.

143. The nicotine salt liquid formulation in the electronic cigarette of any one of embodiments 122-131, wherein said nicotine salt comprises nicotine salicylate.

144. The nicotine salt liquid formulation in the electronic cigarette of any one of embodiments 122-131, wherein said nicotine salt comprises nicotine sorbate.

145. The nicotine salt liquid formulation in the electronic cigarette of any one of embodiments 122-131, wherein said nicotine salt comprises nicotine laurate.

146. The nicotine salt liquid formulation in the electronic cigarette of any one of embodiments 122-131, wherein said nicotine salt comprises nicotine levulinate.

147. The nicotine salt liquid formulation in the electronic cigarette of any one of embodiments 122-131, wherein said nicotine salt comprises nicotine benzoate.

148. The nicotine salt liquid formulation in the electronic cigarette of any one of embodiments 122-147, wherein the liquid carrier comprises glycerol, propylene glycol, trimethylene glycol, water, ethanol or combinations thereof.

149. The nicotine salt liquid formulation in the electronic cigarette of any one of embodiments 122-147, wherein the liquid carrier comprises propylene glycol and vegetable glycerin.

150. The nicotine salt liquid formulation in the electronic cigarette of any one of embodiments 122-147, wherein the liquid carrier comprises 20% to 50% of propylene glycol and 80% to 50% of vegetable glycerin.

151. The nicotine salt liquid formulation in the electronic cigarette of any one of embodiments 122-147, wherein the liquid carrier comprises 30% propylene glycol and 70% vegetable glycerin.

152. The nicotine salt liquid formulation in the electronic cigarette of any one of embodiments 122-151, wherein the nicotine salt is in an amount that forms about 0.5% to about 20% nicotine in the inhalable aerosol.

153. The nicotine salt liquid formulation in the electronic cigarette of any one of embodiments 122-151, wherein the nicotine salt is in an amount that forms about 1% to about 20% nicotine in the inhalable aerosol.

154. The nicotine salt liquid formulation in the electronic cigarette of any one of embodiments 122-153, wherein the liquid formulation has a nicotine concentration of about 1% (w/w) to about 25% (w/w).

155. The nicotine salt liquid formulation in the electronic cigarette of any one of embodiments 122-153, wherein the liquid formulation has a nicotine concentration of about 1% (w/w) to about 20% (w/w).

156. The nicotine salt liquid formulation in the electronic cigarette of any one of embodiments 122-153, wherein the liquid formulation has a nicotine concentration of about 1% (w/w) to about 18% (w/w).

157. The nicotine salt liquid formulation in the electronic cigarette of any one of embodiments 122-153, wherein the liquid formulation has a nicotine concentration of about 1% (w/w) to about 15% (w/w).

158. The nicotine salt liquid formulation in the electronic cigarette of any one of embodiments 122-153, wherein the liquid formulation has a nicotine concentration of about 4% (w/w) to about 12% (w/w).

159. The nicotine salt liquid formulation in the electronic cigarette of any one of embodiments 122-153, wherein the liquid formulation has a nicotine concentration of about 4% (w/w).

160. The nicotine salt liquid formulation in the electronic cigarette of any one of embodiments 122-153, wherein the liquid formulation has a nicotine concentration of about 2% (w/w).

161. The nicotine salt liquid formulation in the electronic cigarette of any one of embodiments 122-160, wherein the formulation further comprises a flavorant.

162. The nicotine salt liquid formulation in the electronic cigarette of any one of embodiments 122-161, wherein the formulation is non-corrosive to an electronic cigarette.

163. The nicotine salt liquid formulation in the electronic cigarette of any one of embodiments 122-162, wherein the acid is stable at and below operating temperature or about 200° C.

164. The nicotine salt liquid formulation in the electronic cigarette of any one of embodiments 122-163, wherein the acid does not decompose at and below operating temperature or about 200° C.

165. The nicotine salt liquid formulation in the electronic cigarette of any one of embodiments 122-164, wherein the acid does not oxidize at and below operating temperature or about 200° C.

166. The nicotine salt liquid formulation in the electronic cigarette of any one of embodiments 122-165, wherein the formulation is non-corrosive to the electronic cigarette.

167. The nicotine salt liquid formulation in the electronic cigarette of any one of embodiments 122-166, wherein the formulation is non-toxic to a user of the electronic cigarette.

168. The nicotine salt liquid formulation in the electronic cigarette of any one of embodiments 122-167 further comprising one or more additional nicotine salts in a biologically acceptable liquid carrier suitable for generating the inhalable aerosol upon heating.

169. The nicotine salt liquid formulation in the electronic cigarette of embodiment 168, wherein a second acid used to form the additional nicotine salt is selected from the group consisting of salicylic acid, sorbic acid, benzoic acid, pyruvic acid, lauric acid, and levulinic acid.

170. A nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is characterized by vapor pressure >20 mmHg at 200° C.

171. A nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is characterized by vapor pressure of about 20 to 200 mmHg at 200° C.

172. A nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

173. A nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

174. The nicotine salt liquid formulation of any one of embodiments 170-172, wherein the electronic cigarette heats the nicotine salt formulation to an operating temperature from 150° C. to 250° C.

175. The nicotine salt liquid formulation of any one of embodiments 170-172, wherein the electronic cigarette heats the nicotine salt formulation to an operating temperature from 180° C. to 220° C.

176. The nicotine salt liquid formulation of any one of embodiments 170-172, wherein the electronic cigarette heats the nicotine salt formulation to an operating temperature of about 200° C.

177. The nicotine salt liquid formulation of embodiment 173, wherein the operating temperature is from 150° C. to 250° C.

178. The nicotine salt liquid formulation of embodiment 173, wherein the operating temperature is from 180° C. to 220° C.

179. The nicotine salt liquid formulation of embodiment 173, wherein the operating temperature is about 200° C.

180. The nicotine salt liquid formulation of any one of embodiments 170-179, wherein the acid is a carboxylic acid.

181. The nicotine salt liquid formulation of any one of embodiments 170-179, wherein the acid used to form said nicotine salt is an organic acid.

182. The nicotine salt liquid formulation of embodiment 181, wherein the organic acid is monocarboxylic acid, aromatic acid, or keto acid.

183. The nicotine salt liquid formulation of embodiment 181, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

184. The liquid formulation of any one of embodiments 170-179, wherein the acid used to form the nicotine salt is salicylic acid.

185. The nicotine salt liquid formulation of any one of embodiments 170-179, wherein the acid used to form the nicotine salt is benzoic acid.

186. The nicotine salt liquid formulation of any one of embodiments 170-179, wherein the acid used to form the nicotine salt is pyruvic acid.

187. The nicotine salt liquid formulation of any one of embodiments 170-179, wherein the acid used to form the nicotine salt is sorbic acid.

188. The nicotine salt liquid formulation of any one of embodiments 170-179, wherein the acid used to form the nicotine salt is lauric acid.

189. The nicotine salt liquid formulation of any one of embodiments 170-179, wherein the acid used to form the nicotine salt is levulinic acid.

190. The nicotine salt liquid formulation of any one of embodiments 170-179, wherein said nicotine salt comprises nicotine pyruvate.

191. The nicotine salt liquid formulation of any one of embodiments 170-179, wherein said nicotine salt comprises nicotine salicylate.

192. The nicotine salt liquid formulation of any one of embodiments 170-179, wherein said nicotine salt comprises nicotine sorbate.

193. The nicotine salt liquid formulation of any one of embodiments 170-179, wherein said nicotine salt comprises nicotine laurate.

194. The nicotine salt liquid formulation of any one of embodiments 170-179, wherein said nicotine salt comprises nicotine levulinate.

195. The nicotine salt liquid formulation of any one of embodiments 170-179, wherein said nicotine salt comprises nicotine benzoate.

196. The nicotine salt liquid formulation of any one of embodiments 170-195, wherein the liquid carrier comprises glycerol, propylene glycol, trimethylene glycol, water, ethanol or combinations thereof.

197. The nicotine salt liquid formulation of any one of embodiments 170-195, wherein the liquid carrier comprises propylene glycol and vegetable glycerin.

198. The nicotine salt liquid formulation of any one of embodiments 170-195, wherein the liquid carrier comprises 20% to 50% of propylene glycol and 80% to 50% of vegetable glycerin.

199. The nicotine salt liquid formulation of any one of embodiments 170-195, wherein the liquid carrier comprises 30% propylene glycol and 70% vegetable glycerin.

200. The nicotine salt liquid formulation of any one of embodiments 170-199, wherein the nicotine salt is in an amount that forms about 0.5% to about 20% nicotine in the inhalable aerosol.

201. The nicotine salt liquid formulation of any one of embodiments 170-199, wherein the nicotine salt is in an amount that forms about 1% to about 20% nicotine in the inhalable aerosol.

202. The nicotine salt liquid formulation of any one of embodiments 170-201, wherein the liquid formulation has a nicotine concentration of about 1% (w/w) to about 25% (w/w).

203. The nicotine salt liquid formulation of any one of embodiments 170-201, wherein the liquid formulation has a nicotine concentration of about 1% (w/w) to about 20% (w/w).

204. The nicotine salt liquid formulation of any one of embodiments 170-201, wherein the liquid formulation has a nicotine concentration of about 1% (w/w) to about 18% (w/w).

205. The nicotine salt liquid formulation of any one of embodiments 170-201, wherein the liquid formulation has a nicotine concentration of about 1% (w/w) to about 15% (w/w).

206. The nicotine salt liquid formulation of any one of embodiments 170-201, wherein the liquid formulation has a nicotine concentration of about 4% (w/w) to about 12% (w/w).

207. The nicotine salt liquid formulation of any one of embodiments 170-201, wherein the liquid formulation has a nicotine concentration of about 4% (w/w).

208. The nicotine salt liquid formulation of any one of embodiments 170-201, wherein the liquid formulation has a nicotine concentration of about 2% (w/w).

209. The nicotine salt liquid formulation of any one of embodiments 170-208, wherein the formulation further comprises a flavorant.

210. The nicotine salt liquid formulation of any one of embodiments 170-209, wherein the formulation is non-corrosive to an electronic cigarette.

211. The nicotine salt liquid formulation of any one of embodiments 170-210, wherein the acid is stable at and below operating temperature or about 200° C.

212. The nicotine salt liquid formulation of any one of embodiments 170-211, wherein the acid does not decompose at and below operating temperature or about 200° C.

213. The nicotine salt liquid formulation of any one of embodiments 170-212, wherein the acid does not oxidize at and below operating temperature or about 200° C.

214. The nicotine salt liquid formulation of any one of embodiments 170-213, wherein the formulation is non-corrosive to the electronic cigarette.

215. The nicotine salt liquid formulation of any one of embodiments 170-214, wherein the formulation is non-toxic to a user of the electronic cigarette.

216. The nicotine salt liquid formulation of any one of embodiments 170-215, further comprising one or more additional nicotine salts in a biologically acceptable liquid carrier suitable for generating the inhalable aerosol upon heating.

217. The nicotine salt liquid formulation of embodiment 216, wherein a second acid used to form the additional nicotine salt is selected from the group consisting of salicylic acid, sorbic acid, benzoic acid, pyruvic acid, lauric acid, and levulinic acid.

218. A nicotine salt liquid formulation for use in an electronic cigarette the nicotine salt liquid formulation comprising a nicotine salt in a biologically acceptable liquid carrier wherein an acid used to form said nicotine salt is characterized by vapor pressure >20 mmHg at 200° C.

219. A nicotine salt liquid formulation for use in an electronic cigarette the nicotine salt liquid formulation comprising a nicotine salt in a biologically acceptable liquid carrier wherein an acid used to form said nicotine salt is characterized by vapor pressure of about 20 to 200 mmHg at 200° C.

220. A nicotine salt liquid formulation for use in an electronic cigarette the nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

221. A nicotine salt liquid formulation for use in an electronic cigarette the nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

222. The nicotine salt liquid formulation of any one of embodiments 218-220, wherein the electronic cigarette heats the nicotine salt formulation to an operating temperature from 150° C. to 250° C.

223. The nicotine salt liquid formulation of any one of embodiments 218-220, wherein the electronic cigarette heats the nicotine salt formulation to an operating temperature from 180° C. to 220° C.

224. The nicotine salt liquid formulation of any one of embodiments 218-220, wherein the electronic cigarette heats the nicotine salt formulation to an operating temperature of about 200° C.

225. The nicotine salt liquid formulation of embodiment 221, wherein the operating temperature is from 150° C. to 250° C.

226. The nicotine salt liquid formulation of embodiment 221, wherein the operating temperature is from 180° C. to 220° C.

227. The nicotine salt liquid formulation of embodiment 221, wherein the operating temperature is about 200° C.

228. The nicotine salt liquid formulation of any one of embodiments 218-227, wherein the acid is a carboxylic acid.

229. The nicotine salt liquid formulation of any one of embodiments 218-227, wherein the acid used to form said nicotine salt is an organic acid.

230. The nicotine salt liquid formulation of embodiment 229, wherein the organic acid is monocarboxylic acid, aromatic acid, or keto acid.

231. The nicotine salt liquid formulation of embodiment 229, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

232. The liquid formulation of any one of embodiments 218-227, wherein the acid used to form the nicotine salt is salicylic acid.

233. The nicotine salt liquid formulation of any one of embodiments 218-227, wherein the acid used to form the nicotine salt is benzoic acid.

234. The nicotine salt liquid formulation of any one of embodiments 218-227, wherein the acid used to form the nicotine salt is pyruvic acid.

235. The nicotine salt liquid formulation of any one of embodiments 218-227, wherein the acid used to form the nicotine salt is sorbic acid.

236. The nicotine salt liquid formulation of any one of embodiments 218-227, wherein the acid used to form the nicotine salt is lauric acid.

237. The nicotine salt liquid formulation of any one of embodiments 218-227, wherein the acid used to form the nicotine salt is levulinic acid.

238. The nicotine salt liquid formulation of any one of embodiments 218-227, wherein said nicotine salt comprises nicotine pyruvate.

239. The nicotine salt liquid formulation of any one of embodiments 218-227, wherein said nicotine salt comprises nicotine salicylate.

240. The nicotine salt liquid formulation of any one of embodiments 218-227, wherein said nicotine salt comprises nicotine sorbate.

241. The nicotine salt liquid formulation of any one of embodiments 218-227, wherein said nicotine salt comprises nicotine laurate.

242. The nicotine salt liquid formulation of any one of embodiments 218-227, wherein said nicotine salt comprises nicotine levulinate.

243. The nicotine salt liquid formulation of any one of embodiments 218-227, wherein said nicotine salt comprises nicotine benzoate.

244. The nicotine salt liquid formulation of any one of embodiments 218-243, wherein the liquid carrier comprises glycerol, propylene glycol, trimethylene glycol, water, ethanol or combinations thereof.

245. The nicotine salt liquid formulation of any one of embodiments 218-243, wherein the liquid carrier comprises propylene glycol and vegetable glycerin.

246. The nicotine salt liquid formulation of any one of embodiments 218-243, wherein the liquid carrier comprises 20% to 50% of propylene glycol and 80% to 50% of vegetable glycerin.

247. The nicotine salt liquid formulation of any one of embodiments 218-243, wherein the liquid carrier comprises 30% propylene glycol and 70% vegetable glycerin.

248. The nicotine salt liquid formulation of any one of embodiments 218-247, wherein the nicotine salt is in an amount that forms about 0.5% to about 20% nicotine in the inhalable aerosol.

249. The nicotine salt liquid formulation of any one of embodiments 218-247, wherein the nicotine salt is in an amount that forms about 1% to about 20% nicotine in the inhalable aerosol.

250. The nicotine salt liquid formulation of any one of embodiments 218-247, wherein the liquid formulation has a nicotine concentration of about 1% (w/w) to about 25% (w/w).

251. The nicotine salt liquid formulation of any one of embodiments 218-247, wherein the liquid formulation has a nicotine concentration of about 1% (w/w) to about 20% (w/w).

252. The nicotine salt liquid formulation of any one of embodiments 218-247, wherein the liquid formulation has a nicotine concentration of about 1% (w/w) to about 18% (w/w).

253. The nicotine salt liquid formulation of any one of embodiments 218-247, wherein the liquid formulation has a nicotine concentration of about 1% (w/w) to about 15% (w/w).

254. The nicotine salt liquid formulation of any one of embodiments 218-247, wherein the liquid formulation has a nicotine concentration of about 4% (w/w) to about 12% (w/w).

255. The nicotine salt liquid formulation of any one of embodiments 218-247, wherein the liquid formulation has a nicotine concentration of about 4% (w/w).

256. The nicotine salt liquid formulation of any one of embodiments 218-247, wherein the liquid formulation has a nicotine concentration of about 2% (w/w).

257. The nicotine salt liquid formulation of any one of embodiments 218-256, wherein the formulation further comprises a flavorant.

258. The nicotine salt liquid formulation of any one of embodiments 218-257, wherein the formulation is non-corrosive to an electronic cigarette.

259. The nicotine salt liquid formulation of any one of embodiments 218-258, wherein the acid is stable at and below operating temperature or about 200° C.

260. The nicotine salt liquid formulation of any one of embodiments 218-259, wherein the acid does not decompose at and below operating temperature or about 200° C.

261. The nicotine salt liquid formulation of any one of embodiments 218-260, wherein the acid does not oxidize at and below operating temperature or about 200° C.

262. The nicotine salt liquid formulation of any one of embodiments 218-261, wherein the formulation is non-corrosive to the electronic cigarette.

263. The nicotine salt liquid formulation of any one of embodiments 218-262, wherein the formulation is non-toxic to a user of the electronic cigarette.

264. The nicotine salt liquid formulation of any one of embodiments 218-263, further comprising one or more additional nicotine salts in a biologically acceptable liquid carrier suitable for generating the inhalable aerosol upon heating.

265. The nicotine salt liquid formulation of embodiment 264, wherein a second acid used to form the additional nicotine salt is selected from the group consisting of salicylic acid, sorbic acid, benzoic acid, pyruvic acid, lauric acid, and levulinic acid.

266. Use of a nicotine salt formulation for delivery of nicotine to a user from an electronic cigarette wherein the nicotine salt formulation comprises a nicotine salt in a biologically acceptable liquid carrier wherein an acid used to form said nicotine salt is characterized by vapor pressure >20 mmHg at 200° C., and the nicotine salt formulation is heated by the electronic cigarette to generate an aerosol inhalable by the user.

267. Use of a nicotine salt formulation for delivery of nicotine to a user from an electronic cigarette wherein the nicotine salt formulation comprises a nicotine salt in a biologically acceptable liquid carrier wherein an acid used to form said nicotine salt is characterized by vapor pressure of about 20 to 200 mmHg at 200° C., and the nicotine salt formulation is heated by the electronic cigarette to generate an aerosol inhalable by the user.

268. Use of a nicotine salt formulation for delivery of nicotine to a user from an electronic cigarette wherein the nicotine salt formulation comprises a nicotine salt in a biologically acceptable liquid carrier wherein an acid used to form said nicotine salt is further characterized by a melting point <160° C., a boiling point >160° C., and at least a 50-degree difference between the melting point and the boiling point, and the nicotine salt formulation is heated by the electronic cigarette to generate an aerosol inhalable by the user.

269. Use of a nicotine salt formulation for delivery of nicotine to the blood of a user from an electronic cigarette, wherein the nicotine salt formulation in the electronic cigarette is heated to form an aerosol which delivers a level of nicotine in the blood of the user that is at least 5 ng/mL at about 1.5 minutes after a first puff of ten puffs of the aerosol, each puff taken at 30 second intervals.

270. Use of a nicotine salt formulation for delivery of nicotine to a user from an electronic cigarette wherein the nicotine salt formulation comprises a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point, and the nicotine salt formulation is heated by the electronic cigarette to generate an aerosol inhalable by the user.

271. The use of any one of embodiments 266-269, wherein the electronic cigarette heats the nicotine salt formulation to an operating temperature is from 150° C. to 250° C.

272. The use of any one of embodiments 266-269, wherein the electronic cigarette heats the nicotine salt formulation to an operating temperature is from 180° C. to 220° C.

273. The use of any one of embodiments 266-269, wherein the electronic cigarette heats the nicotine salt formulation to an operating temperature is about 200° C.

274. The use of embodiment 270, wherein the operating temperature is from 150° C. to 250° C.

275. The use of embodiment 270, wherein the operating temperature is from 180° C. to 220° C.

276. The use of embodiment 270, wherein the operating temperature is about 200° C.

277. The use of any one of embodiments 266-276, wherein the aerosol comprises condensate of the nicotine salt.

278. The use of any one of embodiments 266-276, wherein the aerosol comprises condensate of freebase nicotine.

279. The use of any one of embodiments 266-276, wherein the aerosol comprises condensate of freebase nicotine and condensate of the carrier.

280. The use of any one of embodiments 266-276, wherein the aerosol comprises condensate of freebase nicotine and condensate of the acid.

281. The use of any one of embodiments 266-280, wherein the aerosol comprises condensate in particle sizes from about 0.1 microns to about 5 microns.

282. The use of any one of embodiments 266-280, wherein the aerosol comprises condensate in particle sizes from about 0.1 microns to about 1 or 2 microns.

283. The use of any one of embodiments 266-280, wherein the aerosol comprises condensate in particle sizes from about 0.1 microns to about 0.7 microns.

284. The use of any one of embodiments 266-280, wherein the aerosol comprises condensate in particle sizes from about 0.3 microns to about 0.4 microns.

285. The use of any one of embodiments 266-284, wherein the acid is a carboxylic acid.

286. The use of any one of embodiments 266-284, wherein the acid used to form said nicotine salt is an organic acid.

287. The use of embodiment 286, wherein the organic acid is monocarboxylic acid, aromatic acid, or keto acid.

288. The use of embodiment 286, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

289. The use of any one of embodiments 266-284, wherein the acid used to form the nicotine salt is salicylic acid.

290. The use of any one of embodiments 266-284, wherein the acid used to form the nicotine salt is benzoic acid.

291. The use of any one of embodiments 266-284, wherein the acid used to form the nicotine salt is pyruvic acid.

292. The use of any one of embodiments 266-284, wherein the acid used to form the nicotine salt is sorbic acid.

293. The use of any one of embodiments 266-284, wherein the acid used to form the nicotine salt is lauric acid.

294. The use of any one of embodiments 266-284, wherein the acid used to form the nicotine salt is levulinic acid.

295. The use of any one of embodiments 266-284, wherein said nicotine salt comprises nicotine pyruvate.

296. The use of any one of embodiments 266-284, wherein said nicotine salt comprises nicotine salicylate.

297. The use of any one of embodiments 266-284, wherein said nicotine salt comprises nicotine sorbate.

298. The use of any one of embodiments 266-284, wherein said nicotine salt comprises nicotine laurate.

299. The use of any one of embodiments 266-284, wherein said nicotine salt comprises nicotine levulinate.

300. The use of any one of embodiments 266-284, wherein said nicotine salt comprises nicotine benzoate.

301. The use of any one of embodiments 266-300, wherein the liquid carrier comprises glycerol, propylene glycol, trimethylene glycol, water, ethanol or combinations thereof.

302. The use of any one of embodiments 266-300, wherein the liquid carrier comprises propylene glycol and vegetable glycerin.

303. The use of any one of embodiments 266-300, wherein the liquid carrier comprises 20% to 50% of propylene glycol and 80% to 50% of vegetable glycerin.

304. The use of any one of embodiments 266-300, wherein the liquid carrier comprises 30% propylene glycol and 70% vegetable glycerin.

305. The use of any one of embodiments 266-304, wherein the nicotine salt is in an amount that forms about 0.5% to about 20% nicotine in the inhalable aerosol.

306. The use of any one of embodiments 266-304, wherein the nicotine salt is in an amount that forms about 1% to about 20% nicotine in the inhalable aerosol.

307. The use of any one of embodiments 266-306, wherein the liquid formulation has a nicotine concentration of about 1% (w/w) to about 25% (w/w).

308. The use of any one of embodiments 266-306, wherein the liquid formulation has a nicotine concentration of about 1% (w/w) to about 20% (w/w).

309. The use of any one of embodiments 266-306, wherein the liquid formulation has a nicotine concentration of about 1% (w/w) to about 18% (w/w).

310. The use of any one of embodiments 266-306, wherein the liquid formulation has a nicotine concentration of about 1% (w/w) to about 15% (w/w).

311. The use of any one of embodiments 266-306, wherein the liquid formulation has a nicotine concentration of about 4% (w/w) to about 12% (w/w).

312. The use of any one of embodiments 266-306, wherein the liquid formulation has a nicotine concentration of about 4% (w/w).

313. The use of any one of embodiments 266-306, wherein the liquid formulation has a nicotine concentration of about 2% (w/w).

314. The use of any one of embodiments 266-313, wherein the formulation further comprises a flavorant.

315. The use of any one of embodiments 266-314, wherein the formulation is non-corrosive to an electronic cigarette.

316. The use of any one of embodiments 266-315, wherein the acid is stable at and below operating temperature or about 200° C.

317. The use of any one of embodiments 266-316, wherein the acid does not decompose at and below operating temperature or about 200° C.

318. The use of any one of embodiments 266-317, wherein the acid does not oxidize at and below operating temperature or about 200° C.

319. The use of any one of embodiments 266-318, wherein the formulation is non-corrosive to the electronic cigarette.

320. The use of any one of embodiments 266-319, wherein the formulation is non-toxic to a user of the electronic cigarette.

321. The use of any one of embodiments 266-320, wherein the formulation further comprises one or more additional nicotine salts in a biologically acceptable liquid carrier suitable for generating the inhalable aerosol upon heating.

322. The use of embodiment 321, wherein a second acid used to form the additional nicotine salt is selected from the group consisting of salicylic acid, sorbic acid, benzoic acid, pyruvic acid, lauric acid, and levulinic acid 323. A cartomizer for an electronic cigarette comprising:
a nicotine salt liquid formulation comprising a nicotine salt in a biologically acceptable liquid carrier wherein an acid used to form said nicotine salt is characterized by vapor pressure >20 mmHg at 200° C.;

an atomizer comprising a heating element in fluid communication with the nicotine salt liquid formulation; and
a fluid storage compartment that stores the nicotine salt liquid formulation.

324. A cartomizer for an electronic cigarette comprising:
a nicotine salt liquid formulation comprising a nicotine salt in a biologically acceptable liquid carrier wherein an acid used to form said nicotine salt is characterized by vapor pressure of about 20 to 200 mmHg at 200° C.;
an atomizer comprising a heating element in fluid communication with the nicotine salt liquid formulation; and
a fluid storage compartment that stores the nicotine salt liquid formulation.

325. A cartomizer for an electronic cigarette comprising:
a nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point;
an atomizer comprising a heating element in fluid communication with the nicotine salt liquid formulation; and
a fluid storage compartment that stores the nicotine salt liquid formulation.

326. A cartomizer for an electronic cigarette comprising:
a nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point;
an atomizer comprising a heating element in fluid communication with the nicotine salt liquid formulation; and
a fluid storage compartment that stores the nicotine salt liquid formulation.

327. The cartomizer of any one of embodiments 323-325, wherein the electronic cigarette heats the nicotine salt formulation to an operating temperature from 150° C. to 250° C.

328. The cartomizer of any one of embodiments 323-325, wherein the electronic cigarette heats the nicotine salt formulation to an operating temperature from 180° C. to 220° C.

329. The cartomizer of any one of embodiments 323-325, wherein the electronic cigarette heats the nicotine salt formulation to an operating temperature of about 200° C.

330. The cartomizer of embodiment 326, wherein the operating temperature is from 150° C. to 250° C.

331. The cartomizer of embodiment 326, wherein the operating temperature is from 180° C. to 220° C.

332. The cartomizer of embodiment 326, wherein the operating temperature is about 200° C.

333. The cartomizer of any one of embodiments 323-332, wherein the cartomizer further comprises a mouthpiece.

334. The cartomizer of any one of embodiments 323-333, wherein the acid is a carboxylic acid.

335. The cartomizer of any one of embodiments 323-333, wherein the acid used to form said nicotine salt is an organic acid.

336. The cartomizer of embodiment 335, wherein the organic acid is monocarboxylic acid, aromatic acid, or keto acid.

337. The cartomizer of embodiment 335, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

338. The cartomizer of any one of embodiments 323-333, wherein the acid used to form the nicotine salt is salicylic acid.

339. The cartomizer of any one of embodiments 323-333, wherein the acid used to form the nicotine salt is benzoic acid.

340. The cartomizer of any one of embodiments 323-333, wherein the acid used to form the nicotine salt is pyruvic acid.

341. The cartomizer of any one of embodiments 323-333, wherein the acid used to form the nicotine salt is sorbic acid.

342. The cartomizer of any one of embodiments 323-333, wherein the acid used to form the nicotine salt is lauric acid.

343. The cartomizer of any one of embodiments 323-333, wherein the acid used to form the nicotine salt is levulinic acid.

344. The cartomizer of any one of embodiments 323-333, wherein said nicotine salt comprises nicotine pyruvate.

345. The cartomizer of any one of embodiments 323-333, wherein said nicotine salt comprises nicotine salicylate.

346. The cartomizer of any one of embodiments 323-333, wherein said nicotine salt comprises nicotine sorbate.

347. The cartomizer of any one of embodiments 323-333, wherein said nicotine salt comprises nicotine laurate.

348. The cartomizer of any one of embodiments 323-333, wherein said nicotine salt comprises nicotine levulinate.

349. The cartomizer of any one of embodiments 323-333, wherein said nicotine salt comprises nicotine benzoate.

350. The cartomizer of any one of embodiments 323-349, wherein the liquid carrier comprises glycerol, propylene glycol, trimethylene glycol, water, ethanol or combinations thereof.

351. The cartomizer of any one of embodiments 323-349, wherein the liquid carrier comprises propylene glycol and vegetable glycerin.

352. The cartomizer of any one of embodiments 323-349, wherein the liquid carrier comprises 20% to 50% of propylene glycol and 80% to 50% of vegetable glycerin.

353. The cartomizer of any one of embodiments 323-349, wherein the liquid carrier comprises 30% propylene glycol and 70% vegetable glycerin.

354. The cartomizer of any one of embodiments 323-353, wherein the liquid formulation has a nicotine concentration of about 1% (w/w) to about 25% (w/w).

355. The cartomizer of any one of embodiments 323-353, wherein the liquid formulation has a nicotine concentration of about 1% (w/w) to about 20% (w/w).

356. The cartomizer of any one of embodiments 323-353, wherein the liquid formulation has a nicotine concentration of about 1% (w/w) to about 18% (w/w).

357. The cartomizer of any one of embodiments 323-353, wherein the liquid formulation has a nicotine concentration of about 1% (w/w) to about 15% (w/w).

358. The cartomizer of any one of embodiments 323-353, wherein the liquid formulation has a nicotine concentration of about 4% (w/w) to about 12% (w/w).

359. The cartomizer of any one of embodiments 323-353, wherein the liquid formulation has a nicotine concentration of about 4% (w/w).

360. The cartomizer of any one of embodiments 323-353, wherein the liquid formulation has a nicotine concentration of about 2% (w/w).

361. The cartomizer of any one of embodiments 323-360, wherein the electronic cigarette is configured to generate an aerosol inhalable by a user.

362. The cartomizer of embodiment 361, wherein the aerosol comprises condensate of the nicotine salt.

363. The cartomizer of embodiment 361, wherein the aerosol comprises condensate of freebase nicotine.

364. The cartomizer of embodiment 361, wherein the aerosol comprises condensate of freebase nicotine and condensate of the carrier.

365. The cartomizer of embodiment 361, wherein the aerosol comprises condensate of freebase nicotine and condensate of the acid.

366. The cartomizer of any one of embodiments 361-365, wherein the aerosol comprises condensate in particle sizes from about 0.1 microns to about 5 microns.

367. The cartomizer of any one of embodiments 361-365, wherein the aerosol comprises condensate in particle sizes from about 0.1 microns to about 1 or 2 microns.

368. The cartomizer of any one of embodiments 361-365, wherein the aerosol comprises condensate in particle sizes from about 0.1 microns to about 0.7 microns.

369. The cartomizer of any one of embodiments 361-365, wherein the aerosol comprises condensate in particle sizes from about 0.3 microns to about 0.4 microns.

370. The cartomizer of any one of embodiments 361-369, wherein the nicotine salt is in an amount that forms about 0.5% to about 20% nicotine in the inhalable aerosol.

371. The cartomizer of any one of embodiments 361-369, wherein the nicotine salt is in an amount that forms about 1% to about 20% nicotine in the inhalable aerosol.

372. The cartomizer of any one of embodiments 323-371, wherein the formulation further comprises a flavorant.

373. The cartomizer of any one of embodiments 323-372, wherein the formulation is non-corrosive to an electronic cigarette.

374. The cartomizer of any one of embodiments 323-373, wherein the acid is stable at and below operating temperature or about 200° C.

375. The cartomizer of any one of embodiments 323-374, wherein the acid does not decompose at and below operating temperature or about 200° C.

376. The cartomizer of any one of embodiments 323-375, wherein the acid does not oxidize at and below operating temperature or about 200° C.

377. The cartomizer of any one of embodiments 323-376, wherein the formulation is non-corrosive to the electronic cigarette.

378. The cartomizer of any one of embodiments 323-377, wherein the formulation is non-toxic to a user of the electronic cigarette.

379. The cartomizer of any one of embodiments 323-378, wherein the formulation further comprises one or more additional nicotine salts in a biologically acceptable liquid carrier suitable for generating the inhalable aerosol upon heating.

380. The cartomizer of embodiment 379, wherein a second acid used to form the additional nicotine salt is selected from the group consisting of salicylic acid, sorbic acid, benzoic acid, pyruvic acid, lauric acid, and levulinic acid.

381. An electronic cigarette for generating an inhalable aerosol comprising
a fluid storage compartment;
a heater; and
a nicotine salt liquid formulation in the fluid storage compartment, the liquid formulation comprising a nicotine salt in a biologically acceptable liquid carrier wherein an acid used to form said nicotine salt is characterized by vapor pressure >20 mmHg at 200° C.;
a battery; and
a mouthpiece.

382. An electronic cigarette for generating an inhalable aerosol comprising
a fluid storage compartment;
a heater; and
a nicotine salt liquid formulation in the fluid storage compartment, the liquid formulation comprising a nicotine salt in a biologically acceptable liquid carrier wherein an acid used to form said nicotine salt is characterized by vapor pressure of about 20 to 200 mmHg at 200° C.;
a battery; and
a mouthpiece.

383. An electronic cigarette for generating an inhalable aerosol comprising
a fluid storage compartment;
a heater; and
a nicotine salt liquid formulation in the fluid storage compartment, the liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point;
a battery; and
a mouthpiece.

384. An electronic cigarette for generating an inhalable aerosol comprising
a fluid storage compartment;
a heater; and
a nicotine salt liquid formulation in the fluid storage compartment, the liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point;
a battery; and
a mouthpiece.

385. The electronic cigarette of any one of embodiments 381-384, wherein the heater comprises a heater chamber, a fluid wick, and a resistive heating element in contact with the fluid wick.

386. The electronic cigarette of any one of embodiments 381-384, wherein the mouthpiece, the heater and the fluid storage compartment form a cartomizer separable from the battery.

387. The electronic cigarette of any one of embodiments 381-384, wherein the heater and the fluid storage compartment form a cartomizer separable from the battery and the mouthpiece.

388. The electronic cigarette of any one of embodiments 381-384, wherein the fluid storage compartment is separable from the heater, the battery and the mouthpiece.

389. The electronic cigarette of any one of embodiments 381-383, wherein the electronic cigarette heats the nicotine salt formulation to an operating temperature from 150° C. to 250° C.

390. The electronic cigarette of any one of embodiments 381-383, wherein the electronic cigarette heats the nicotine salt formulation to an operating temperature from 180° C. to 220° C.

391. The electronic cigarette of any one of embodiments 381-383, wherein the electronic cigarette heats the nicotine salt formulation to an operating temperature of about 200° C.

392. The electronic cigarette of embodiment 384, wherein the operating temperature is from 150° C. to 250° C.

393. The electronic cigarette of embodiment 384, wherein the operating temperature is from 180° C. to 220° C.

394. The electronic cigarette of embodiment 384, wherein the operating temperature is about 200° C.

395. The electronic cigarette of any one of embodiments 381-394, wherein the aerosol comprises condensate of the nicotine salt.

396. The electronic cigarette of any one of embodiments 381-394, wherein the aerosol comprises condensate of freebase nicotine.

397. The electronic cigarette of any one of embodiments 381-394, wherein the aerosol comprises condensate of freebase nicotine and condensate of the carrier.

398. The electronic cigarette of any one of embodiments 381-394, wherein the aerosol comprises condensate of freebase nicotine and condensate of the acid.

399. The electronic cigarette of any one of embodiments 381-398, wherein the aerosol comprises condensate in particle sizes from about 0.1 microns to about 5 microns.

400. The electronic cigarette of any one of embodiments 381-398, wherein the aerosol comprises condensate in particle sizes from about 0.1 microns to about 1 or 2 microns.

401. The electronic cigarette of any one of embodiments 381-398, wherein the aerosol comprises condensate in particle sizes from about 0.1 microns to about 0.7 microns.

402. The electronic cigarette of any one of embodiments 381-398, wherein the aerosol comprises condensate in particle sizes from about 0.3 microns to about 0.4 microns.

403. The electronic cigarette of any one of embodiments 381-402, wherein the acid is a carboxylic acid.

404. The electronic cigarette of any one of embodiments 381-402, wherein the acid used to form said nicotine salt is an organic acid.

405. The electronic cigarette of embodiment 404, wherein the organic acid is monocarboxylic acid, aromatic acid, or keto acid.

406. The electronic cigarette of embodiment 404, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

407. The electronic cigarette of any one of embodiments 381-402, wherein the acid used to form the nicotine salt is salicylic acid.

408. The electronic cigarette of any one of embodiments 381-402, wherein the acid used to form the nicotine salt is benzoic acid.

409. The electronic cigarette of any one of embodiments 381-402, wherein the acid used to form the nicotine salt is pyruvic acid.

410. The electronic cigarette of any one of embodiments 381-402, wherein the acid used to form the nicotine salt is sorbic acid.

411. The electronic cigarette of any one of embodiments 381-402, wherein the acid used to form the nicotine salt is lauric acid.

412. The electronic cigarette of any one of embodiments 381-402, wherein the acid used to form the nicotine salt is levulinic acid.

413. The electronic cigarette of any one of embodiments 381-402, wherein said nicotine salt comprises nicotine pyruvate.

414. The electronic cigarette of any one of embodiments 381-402, wherein said nicotine salt comprises nicotine salicylate.

415. The electronic cigarette of any one of embodiments 381-402, wherein said nicotine salt comprises nicotine sorbate.

416. The electronic cigarette of any one of embodiments 381-402, wherein said nicotine salt comprises nicotine laurate.

417. The electronic cigarette of any one of embodiments 381-402, wherein said nicotine salt comprises nicotine levulinate.

418. The electronic cigarette of any one of embodiments 381-402, wherein said nicotine salt comprises nicotine benzoate.

419. The electronic cigarette of any one of embodiments 381-419, wherein the liquid carrier comprises glycerol, propylene glycol, trimethylene glycol, water, ethanol or combinations thereof.

420. The electronic cigarette of any one of embodiments 381-419, wherein the liquid carrier comprises propylene glycol and vegetable glycerin.

421. The electronic cigarette of any one of embodiments 381-419, wherein the liquid carrier comprises 20% to 50% of propylene glycol and 80% to 50% of vegetable glycerin.

422. The electronic cigarette of any one of embodiments 381-419, wherein the liquid carrier comprises 30% propylene glycol and 70% vegetable glycerin.

423. The electronic cigarette of any one of embodiments 381-422, wherein the nicotine salt is in an amount that forms about 0.5% to about 20% nicotine in the inhalable aerosol.

424. The electronic cigarette of any one of embodiments 381-422, wherein the nicotine salt is in an amount that forms about 1% to about 20% nicotine in the inhalable aerosol.

425. The electronic cigarette of any one of embodiments 381-424, wherein the liquid formulation has a nicotine concentration of about 1% (w/w) to about 25% (w/w).

426. The electronic cigarette of any one of embodiments 381-424, wherein the liquid formulation has a nicotine concentration of about 1% (w/w) to about 20% (w/w).

427. The electronic cigarette of any one of embodiments 381-424, wherein the liquid formulation has a nicotine concentration of about 1% (w/w) to about 18% (w/w).

428. The electronic cigarette of any one of embodiments 381-424, wherein the liquid formulation has a nicotine concentration of about 1% (w/w) to about 15% (w/w).

429. The electronic cigarette of any one of embodiments 381-424, wherein the liquid formulation has a nicotine concentration of about 4% (w/w) to about 12% (w/w).

430. The electronic cigarette of any one of embodiments 381-424, wherein the liquid formulation has a nicotine concentration of about 4% (w/w).

431. The electronic cigarette of any one of embodiments 381-424, wherein the liquid formulation has a nicotine concentration of about 2% (w/w).

432. The electronic cigarette of any one of embodiments 381-431, wherein the formulation further comprises a flavorant.

433. The electronic cigarette of any one of embodiments 381-432, wherein the formulation is non-corrosive to an electronic cigarette.

434. The electronic cigarette of any one of embodiments 381-433, wherein the acid is stable at and below operating temperature or about 200° C.

435. The electronic cigarette of any one of embodiments 381-434, wherein the acid does not decompose at and below operating temperature or about 200° C.

436. The electronic cigarette of any one of embodiments 381-435, wherein the acid does not oxidize at and below operating temperature or about 200° C.

437. The electronic cigarette of any one of embodiments 381-436, wherein the formulation is non-corrosive to the electronic cigarette.

438. The electronic cigarette of any one of embodiments 381-437, wherein the formulation is non-toxic to a user of the electronic cigarette.

439. The electronic cigarette of any one of embodiments 381-438, wherein the formulation further comprises one or more additional nicotine salts in a biologically acceptable liquid carrier suitable for generating the inhalable aerosol upon heating.

440. The electronic cigarette of embodiment 439, wherein a second acid used to form the additional nicotine salt is selected from the group consisting of salicylic acid, sorbic acid, benzoic acid, pyruvic acid, lauric acid, and levulinic acid.

441. A cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure >20 mmHg at 200° C.

442. A cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure of about 20 to 200 mmHg at 200° C.

443. A cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

444. A cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

445. The cartridge of any one of embodiments 441-444, wherein the cartridge is separable from the electronic cigarette.

446. The cartridge of any one of embodiments 441-445, wherein the acid is a carboxylic acid.

447. The cartridge of any one of embodiments 441-445, wherein the acid used to form said nicotine salt is an organic acid.

448. The cartridge of embodiment 447, wherein the organic acid is monocarboxylic acid, aromatic acid, or keto acid.

449. The cartridge of embodiment 447, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

450. The cartridge of any one of embodiments 441-445, wherein the acid used to form the nicotine salt is salicylic acid.

451. The cartridge of any one of embodiments 441-445, wherein the acid used to form the nicotine salt is benzoic acid.

452. The cartridge of any one of embodiments 441-445, wherein the acid used to form the nicotine salt is pyruvic acid.

453. The cartridge of any one of embodiments 441-445, wherein the acid used to form the nicotine salt is sorbic acid.

454. The cartridge of any one of embodiments 441-445, wherein the acid used to form the nicotine salt is lauric acid.

455. The cartridge of any one of embodiments 441-445, wherein the acid used to form the nicotine salt is levulinic acid.

456. The cartridge of any one of embodiments 441-445, wherein said nicotine salt comprises nicotine pyruvate.

457. The cartridge of any one of embodiments 441-445, wherein said nicotine salt comprises nicotine salicylate.

458. The cartridge of any one of embodiments 441-445, wherein said nicotine salt comprises nicotine sorbate.

459. The cartridge of any one of embodiments 441-445, wherein said nicotine salt comprises nicotine laurate.

460. The cartridge of any one of embodiments 441-445, wherein said nicotine salt comprises nicotine levulinate.

461. The cartridge of any one of embodiments 441-445, wherein said nicotine salt comprises nicotine benzoate.

462. The cartridge of any one of embodiments 441-461, wherein the liquid carrier comprises glycerol, propylene glycol, trimethylene glycol, water, ethanol or combinations thereof.

463. The cartridge of any one of embodiments 441-461, wherein the liquid carrier comprises propylene glycol and vegetable glycerin.

464. The cartridge of any one of embodiments 441-461, wherein the liquid carrier comprises 20% to 50% of propylene glycol and 80% to 50% of vegetable glycerin.

465. The cartridge of any one of embodiments 441-461, wherein the liquid carrier comprises 30% propylene glycol and 70% vegetable glycerin.

466. The cartridge of any one of embodiments 441-465, wherein the liquid formulation has a nicotine concentration of about 1% (w/w) to about 25% (w/w).

467. The cartridge of any one of embodiments 441-465, wherein the liquid formulation has a nicotine concentration of about 1% (w/w) to about 20% (w/w).

468. The cartridge of any one of embodiments 441-465, wherein the liquid formulation has a nicotine concentration of about 1% (w/w) to about 18% (w/w).

469. The cartridge of any one of embodiments 441-465, wherein the liquid formulation has a nicotine concentration of about 1% (w/w) to about 15% (w/w).

470. The cartridge of any one of embodiments 441-465, wherein the liquid formulation has a nicotine concentration of about 4% (w/w) to about 12% (w/w).

471. The cartridge of any one of embodiments 441-465, wherein the liquid formulation has a nicotine concentration of about 4% (w/w).

472. The cartridge of any one of embodiments 441-465, wherein the liquid formulation has a nicotine concentration of about 2% (w/w).

473. The cartridge of any one of embodiments 441-472, wherein the formulation further comprises a flavorant.

474. The cartridge of any one of embodiments 441-473, wherein the formulation is non-corrosive to an electronic cigarette.

475. The cartridge of any one of embodiments 441-474, wherein the acid is stable at and below operating temperature or about 200° C.

476. The cartridge of any one of embodiments 441-475, wherein the acid does not decompose at and below operating temperature or about 200° C.

477. The cartridge of any one of embodiments 441-476, wherein the acid does not oxidize at and below operating temperature or about 200° C.

478. The cartridge of any one of embodiments 441-477, wherein the formulation is non-corrosive to the electronic cigarette.

479. The cartridge of any one of embodiments 441-478, wherein the formulation is non-toxic to a user of the electronic cigarette.

480. The cartridge of any one of embodiments 441-479, wherein the formulation further comprises one or more additional nicotine salts in a biologically acceptable liquid carrier suitable for generating the inhalable aerosol upon heating.

481. The cartridge of embodiment 480, wherein a second acid used to form the additional nicotine salt is selected from the group consisting of salicylic acid, sorbic acid, benzoic acid, pyruvic acid, lauric acid, and levulinic acid.

482. A kit comprising:
(a) an electronic cigarette for generating an inhalable aerosol comprising
  i. a device body comprising a cartridge receptacle;
  ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure >20 mmHg at 200° C.;
  iii. a heater;
  iv. a battery; and
  v. a mouthpiece; and
(b) instructions for using the electronic cigarette to generate an inhalable aerosol.

483. A kit comprising:
(a) an electronic cigarette for generating an inhalable aerosol comprising
  i. a device body comprising a cartridge receptacle;
  ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure of about 20 to 200 mmHg at 200° C.;
  iii. a heater;
  iv. a battery; and
  v. a mouthpiece; and
(b) instructions for using the electronic cigarette to generate an inhalable aerosol.

484. A kit comprising:
(a) an electronic cigarette for generating an inhalable aerosol comprising
  i. a device body comprising a cartridge receptacle;
  ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point;
  iii. a heater;
  iv. a battery; and
  v. a mouthpiece; and
(b) instructions for using the electronic cigarette to generate an inhalable aerosol.

485. A kit comprising:
(a) an electronic cigarette for generating an inhalable aerosol comprising
  i. a device body comprising a cartridge receptacle;
  ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point;
  iii. a heater;
  iv. a battery; and
  v. a mouthpiece; and
(b) instructions for using the electronic cigarette to generate an inhalable aerosol.

486. The kit of any one of embodiments 482-485, wherein the acid is a carboxylic acid.

487. The kit of any one of embodiments 482-485, wherein the acid used to form said nicotine salt is an organic acid.

488. The kit of embodiment 487, wherein the organic acid is monocarboxylic acid, aromatic acid, or keto acid.

489. The kit of embodiment 487, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

490. The kit of any one of embodiments 482-485, wherein the acid used to form the nicotine salt is salicylic acid.

491. The kit of any one of embodiments 482-485, wherein the acid used to form the nicotine salt is benzoic acid.

492. The kit of any one of embodiments 482-485, wherein the acid used to form the nicotine salt is pyruvic acid.

493. The kit of any one of embodiments 482-485, wherein the acid used to form the nicotine salt is sorbic acid.

494. The kit of any one of embodiments 482-485, wherein the acid used to form the nicotine salt is lauric acid.

495. The kit of any one of embodiments 482-485, wherein the acid used to form the nicotine salt is levulinic acid.

496. The kit of any one of embodiments 482-485, wherein said nicotine salt comprises nicotine pyruvate.

497. The kit of any one of embodiments 482-485, wherein said nicotine salt comprises nicotine salicylate.

498. The kit of any one of embodiments 482-485, wherein said nicotine salt comprises nicotine sorbate.

499. The kit of any one of embodiments 482-485, wherein said nicotine salt comprises nicotine laurate.

500. The kit of any one of embodiments 482-485, wherein said nicotine salt comprises nicotine levulinate.

501. The kit of any one of embodiments 482-485, wherein said nicotine salt comprises nicotine benzoate.

502. The kit of any one of embodiments 482-501, wherein the liquid carrier comprises glycerol, propylene glycol, trimethylene glycol, water, ethanol or combinations thereof.

503. The kit of any one of embodiments 482-501, wherein the liquid carrier comprises propylene glycol and vegetable glycerin.

504. The kit of any one of embodiments 482-501, wherein the liquid carrier comprises 20% to 50% of propylene glycol and 80% to 50% of vegetable glycerin.

505. The kit of any one of embodiments 482-501, wherein the liquid carrier comprises 30% propylene glycol and 70% vegetable glycerin.

506. The kit of any one of embodiments 482-505, wherein the liquid formulation has a nicotine concentration of about 1% (w/w) to about 25% (w/w).

507. The kit of any one of embodiments 482-505, wherein the liquid formulation has a nicotine concentration of about 1% (w/w) to about 20% (w/w).

508. The kit of any one of embodiments 482-505, wherein the liquid formulation has a nicotine concentration of about 1% (w/w) to about 18% (w/w).

509. The kit of any one of embodiments 482-505, wherein the liquid formulation has a nicotine concentration of about 1% (w/w) to about 15% (w/w).

510. The kit of any one of embodiments 482-505, wherein the liquid formulation has a nicotine concentration of about 4% (w/w) to about 12% (w/w).

511. The kit of any one of embodiments 482-505, wherein the liquid formulation has a nicotine concentration of about 4% (w/w).

512. The kit of any one of embodiments 482-505, wherein the liquid formulation has a nicotine concentration of about 2% (w/w).

513. The kit of any one of embodiments 482-512, wherein the formulation further comprises a flavorant.

514. The kit of any one of embodiments 482-513, wherein the formulation is non-corrosive to an electronic cigarette.

515. The kit of any one of embodiments 482-514, wherein the acid is stable at and below operating temperature or about 200° C.

516. The kit of any one of embodiments 482-515, wherein the acid does not decompose at and below operating temperature or about 200° C.

517. The kit of any one of embodiments 482-516, wherein the acid does not oxidize at and below operating temperature or about 200° C.

518. The kit of any one of embodiments 482-517, wherein the formulation is non-corrosive to the electronic cigarette.

519. The kit of any one of embodiments 482-518, wherein the formulation is non-toxic to a user of the electronic cigarette.

520. The kit of any one of embodiments 482-519, wherein the formulation further comprises one or more additional nicotine salts in a biologically acceptable liquid carrier suitable for generating the inhalable aerosol upon heating.

521. The kit of embodiment 520, wherein a second acid used to form the additional nicotine salt is selected from the group consisting of salicylic acid, sorbic acid, benzoic acid, pyruvic acid, lauric acid, and levulinic acid.

522. A cartridge comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure >20 mmHg at 200° C.

523. A cartridge comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure of about 20 to 200 mmHg at 200° C.

524. A cartridge comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

525. A cartridge comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

526. The cartridge of any one of embodiments 523-526, wherein the cartridge can be connected to an electronic cigarette.

527. The cartridge of any one of embodiments 523-527, wherein the acid is a carboxylic acid.

528. The cartridge of any one of embodiments 523-527, wherein the acid used to form said nicotine salt is an organic acid.

529. The cartridge of embodiment 529, wherein the organic acid is monocarboxylic acid, aromatic acid, or keto acid.

530. The cartridge of embodiment 529, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

531. The cartridge of any one of embodiments 523-527, wherein the acid used to form the nicotine salt is salicylic acid.

532. The cartridge of any one of embodiments 523-527, wherein the acid used to form the nicotine salt is benzoic acid.

533. The cartridge of any one of embodiments 523-527, wherein the acid used to form the nicotine salt is pyruvic acid.

534. The cartridge of any one of embodiments 523-527, wherein the acid used to form the nicotine salt is sorbic acid.

535. The cartridge of any one of embodiments 523-527, wherein the acid used to form the nicotine salt is lauric acid.

536. The cartridge of any one of embodiments 523-527, wherein the acid used to form the nicotine salt is levulinic acid.

537. The cartridge of any one of embodiments 523-527, wherein said nicotine salt comprises nicotine pyruvate.

538. The cartridge of any one of embodiments 523-527, wherein said nicotine salt comprises nicotine salicylate.

539. The cartridge of any one of embodiments 523-527, wherein said nicotine salt comprises nicotine sorbate.

540. The cartridge of any one of embodiments 523-527, wherein said nicotine salt comprises nicotine laurate.

541. The cartridge of any one of embodiments 523-527, wherein said nicotine salt comprises nicotine levulinate.

542. The cartridge of any one of embodiments 523-527, wherein said nicotine salt comprises nicotine benzoate.

543. The cartridge of any one of embodiments 523-543, wherein the liquid carrier comprises glycerol, propylene glycol, trimethylene glycol, water, ethanol or combinations thereof.

544. The cartridge of any one of embodiments 523-543, wherein the liquid carrier comprises propylene glycol and vegetable glycerin.

545. The cartridge of any one of embodiments 523-543, wherein the liquid carrier comprises 20% to 50% of propylene glycol and 80% to 50% of vegetable glycerin.

546. The cartridge of any one of embodiments 523-543, wherein the liquid carrier comprises 30% propylene glycol and 70% vegetable glycerin.

547. The cartridge of any one of embodiments 523-547, wherein the liquid formulation has a nicotine concentration of about 1% (w/w) to about 25% (w/w).

548. The cartridge of any one of embodiments 523-547, wherein the liquid formulation has a nicotine concentration of about 1% (w/w) to about 20% (w/w).

549. The cartridge of any one of embodiments 523-547, wherein the liquid formulation has a nicotine concentration of about 1% (w/w) to about 18% (w/w).

550. The cartridge of any one of embodiments 523-547, wherein the liquid formulation has a nicotine concentration of about 1% (w/w) to about 15% (w/w).

551. The cartridge of any one of embodiments 523-547, wherein the liquid formulation has a nicotine concentration of about 4% (w/w) to about 12% (w/w).

552. The cartridge of any one of embodiments 523-547, wherein the liquid formulation has a nicotine concentration of about 4% (w/w).

553. The cartridge of any one of embodiments 523-547, wherein the liquid formulation has a nicotine concentration of about 2% (w/w).

554. The cartridge of any one of embodiments 523-553, wherein the formulation further comprises a flavorant.

555. The cartridge of any one of embodiments 523-554, wherein the formulation is non-corrosive to an electronic cigarette.

556. The cartridge of any one of embodiments 523-555, wherein the acid is stable at and below operating temperature or about 200° C.

557. The cartridge of any one of embodiments 523-556, wherein the acid does not decompose at and below operating temperature or about 200° C.

558. The cartridge of any one of embodiments 523-557, wherein the acid does not oxidize at and below operating temperature or about 200° C.

559. The cartridge of any one of embodiments 523-558, wherein the formulation is non-corrosive to the electronic cigarette.

560. The cartridge of any one of embodiments 523-559, wherein the formulation is non-toxic to a user of the electronic cigarette.

561. The cartridge of any one of embodiments 523-560, wherein the formulation further comprises one or more additional nicotine salts in a biologically acceptable liquid carrier suitable for generating the inhalable aerosol upon heating.

562. The cartridge of embodiment 561, wherein a second acid used to form the additional nicotine salt is selected from the group consisting of salicylic acid, sorbic acid, benzoic acid, pyruvic acid, lauric acid, and levulinic acid.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following embodiments define the scope of the invention and that methods and structures within the scope of these embodiments and their equivalents be covered thereby.

What is claimed is:

1. An electronic cigarette comprising a cartridge, wherein the cartridge comprises a nicotine salt liquid formulation, wherein:
    (a) the nicotine salt liquid formulation comprises a salt of nicotine and an organic acid in a liquid carrier, wherein the organic acid is benzoic acid or lactic acid;
    (b) the salt is present in an amount that forms a nicotine concentration of 0.5% (w/w) to 20% (w/w) in the nicotine salt liquid formulation;
    (c) the liquid carrier comprises glycerol and propylene glycol; and
    (d) the nicotine salt liquid formulation generates an inhalable aerosol upon heating in the electronic cigarette.

2. The electronic cigarette of claim 1, wherein the liquid carrier further comprises water.

3. The electronic cigarette of claim 1, wherein the salt is present in an amount that forms a nicotine concentration of 1% (w/w) to 18% (w/w) in the nicotine salt liquid formulation.

4. The electronic cigarette of claim 1, wherein the salt is present in an amount that forms a nicotine concentration of 3% (w/w) to 15% (w/w) in the nicotine salt liquid formulation.

5. The electronic cigarette of claim 1, wherein the salt is present in an amount that forms a nicotine concentration of 4% (w/w) to 12% (w/w) in the nicotine salt liquid formulation.

6. The electronic cigarette of claim 1, wherein the nicotine salt liquid formulation further comprises a flavorant.

7. The electronic cigarette of claim 1, wherein the nicotine salt liquid formulation further comprises one or more additional organic acids.

8. The electronic cigarette of claim 1, wherein the cartridge is configured to serve as a mouthpiece and a reservoir, wherein the reservoir holds the nicotine salt liquid formulation.

9. The electronic cigarette of claim 1, wherein the organic acid is benzoic acid.

10. The electronic cigarette of claim 1, wherein the organic acid is lactic acid.

11. A method of providing nicotine to a user, the method comprising:
   (a) heating a nicotine salt liquid formulation in an electronic cigarette to produce an inhalable aerosol, and
   (b) inhalation of the aerosol by the user;
   wherein:
   (i) the nicotine salt liquid formulation comprises a salt of nicotine and benzoic acid in a liquid carrier;
   (ii) the salt is present in an amount that forms a nicotine concentration of 0.5% (w/w) to 20% (w/w) in the nicotine salt liquid formulation; and
   (iii) the liquid carrier comprises glycerol and propylene glycol.

12. The method of claim 11, wherein the liquid carrier further comprises water.

13. The method of claim 11, wherein the salt is present in an amount that forms a nicotine concentration of 1% (w/w) to 20% (w/w) in the nicotine salt liquid formulation.

14. The method of claim 11, wherein the salt is present in an amount that forms a nicotine concentration of 1% (w/w) to 18% (w/w) in the nicotine salt liquid formulation.

15. The method of claim 11, wherein the salt is present in an amount that forms a nicotine concentration of 3% (w/w) to 15% (w/w) in the nicotine salt liquid formulation.

16. The method of claim 11, wherein the salt is present in an amount that forms a nicotine concentration of 4% (w/w) to 12% (w/w) in the nicotine salt liquid formulation.

17. The method of claim 11, wherein the nicotine salt liquid formulation further comprises a flavorant.

18. The method of claim 11, wherein the nicotine salt liquid formulation further comprises one or more additional organic acids.

19. The method of claim 11, wherein the electronic cigarette comprises a cartridge, and the cartridge is configured to serve as a mouthpiece and a reservoir, wherein the reservoir holds the nicotine salt liquid formulation.

* * * * *